(12) United States Patent
Putnam et al.

(10) Patent No.: US 7,901,630 B2
(45) Date of Patent: *Mar. 8, 2011

(54) DIFFRACTION GRATING-BASED ENCODED MICROPARTICLE ASSAY STICK

(75) Inventors: Martin A. Putnam, Cheshire, CT (US); John A. Moon, Wallingford, CT (US); Tuo Li, East Lyme, CT (US)

(73) Assignee: Illumina, Inc., San Diego, CA (US)

( * ) Notice: Subject to any disclaimer, the term of this patent is extended or adjusted under 35 U.S.C. 154(b) by 1195 days.

This patent is subject to a terminal disclaimer.

(21) Appl. No.: 11/226,914

(22) Filed: Sep. 13, 2005

(65) Prior Publication Data

US 2006/0072177 A1 Apr. 6, 2006

Related U.S. Application Data

(63) Continuation-in-part of application No. 10/661,234, filed on Sep. 12, 2003, now Pat. No. 7,106,513, which is a continuation-in-part of application No. 10/645,689, filed on Aug. 20, 2003, now abandoned, which is a continuation-in-part of application No. 10/661,031, filed on Sep. 12, 2003, now Pat. No. 7,349,158, which is a continuation-in-part of application No. 10/645,686, filed on Aug. 20, 2003, now abandoned, which is a continuation-in-part of application No. 10/661,082, filed on Sep. 12, 2003, now Pat. No. 7,126,755, which is a continuation-in-part of application No. 10/661,115, filed on Sep. 12, 2003, now abandoned.

(60) Provisional application No. 60/610,059, filed on Sep. 13, 2004, provisional application No. 60/654,716, filed on Feb. 17, 2005, provisional application No. 60/410,541, filed on Sep. 12, 2002, provisional application No. 60/405,087, filed on Aug. 20, 2002.

(51) Int. Cl.
*G01N 33/00* (2006.01)
*G01N 33/556* (2006.01)
*G03H 1/00* (2006.01)
*C12M 1/34* (2006.01)
*C12M 3/00* (2006.01)

(52) U.S. Cl. ............. 422/73; 436/521; 359/2; 435/287.2
(58) Field of Classification Search ............... 435/287.2; 422/173, 50, 58, 73; 436/164, 523, 518, 436/521
See application file for complete search history.

(56) References Cited

U.S. PATENT DOCUMENTS 3,074,634 A 1/1963 Gamo
(Continued)

FOREIGN PATENT DOCUMENTS

CH 598661 A 5/1978
(Continued)

OTHER PUBLICATIONS

"Electronically Scanned Confocal Imaging System"; IBM Technical Disclosure Bulletin; vol. 36; No. 06B; Jun. 1993; pp. 261-262.
(Continued)

*Primary Examiner* — Samuel P Siefke
*Assistant Examiner* — Bryan T Kilpatrick
(74) *Attorney, Agent, or Firm* — The Small Patent Law Group; Dean Small; Jason P. Gross

(57) ABSTRACT

An assay stick 7 includes a transparent reaction vessel or tube 14 having one or more microbeads 8 disposed therein. The microbeads 8 have a plurality of unique identification digital codes based on a diffraction grating 12 disposed therein that are detected when illuminated by incident light 24. The incident light 24 may be directed transversely onto the side or onto an end of the tube 14 with a narrow band (single wavelength) or multiple wavelength source, in which case the code is represented by a spatial distribution of light or a wavelength spectrum, respectively. The assay stick 7 may be reused or disposed upon completion of the assay. Alternatively, the beads may be attached to a strip or planar surface. The encoded beads can also provide traceability, quality-control, and authenticity of each bead 8 to its source and/or to the chemistry on each bead 8. Also, the low sample volume of the assay stick allows for faster reactions and better sensitivity.

20 Claims, 26 Drawing Sheets

U.S. PATENT DOCUMENTS

| | | |
|---|---|---|
| 3,600,223 A | 8/1971 | Glick |
| 3,614,193 A | 10/1971 | Beiser |
| 3,791,788 A | 2/1974 | Taylor |
| 3,891,302 A | 6/1975 | Dabby et al. |
| 3,916,182 A | 10/1975 | Dabby et al. |
| 3,928,253 A | 12/1975 | Thornton et al. |
| 3,968,476 A | 7/1976 | McMahon |
| 4,011,435 A | 3/1977 | Phelps |
| 4,023,010 A | 5/1977 | Horst et al. |
| 4,053,228 A | 10/1977 | Schiller |
| 4,053,433 A | 10/1977 | Lee |
| 4,112,037 A | 9/1978 | Parker et al. |
| 4,131,337 A | 12/1978 | Moraw et al. |
| 4,168,146 A | 9/1979 | Grubb et al. |
| 4,301,139 A | 11/1981 | Feingers et al. |
| 4,386,274 A | 5/1983 | Altshuler |
| 4,400,616 A | 8/1983 | Chevillat et al. |
| 4,445,229 A | 4/1984 | Tasto et al. |
| 4,447,546 A | 5/1984 | Hirschfeld |
| 4,537,504 A | 8/1985 | Baltes et al. |
| 4,560,881 A | 12/1985 | Briggs |
| 4,562,157 A | 12/1985 | Lowe et al. |
| 4,647,544 A | 3/1987 | Nicoli et al. |
| 4,678,752 A | 7/1987 | Thorne et al. |
| 4,685,480 A | 8/1987 | Eck |
| 4,690,907 A | 9/1987 | Hibino et al. |
| 4,701,754 A | 10/1987 | Provonchee |
| 4,716,121 A | 12/1987 | Block et al. |
| 4,725,110 A | 2/1988 | Glenn et al. |
| 4,740,468 A | 4/1988 | Weng et al. |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A | 9/1988 | Carveth et al. |
| 4,807,950 A | 2/1989 | Glenn et al. |
| 4,815,027 A | 3/1989 | Tokumitsu |
| 4,816,659 A | 3/1989 | Bianco et al. |
| 4,822,746 A | 4/1989 | Walt |
| 4,841,140 A | 6/1989 | Sullivan et al. |
| 4,843,631 A | 6/1989 | Steinpichler |
| 4,877,747 A | 10/1989 | Stewart |
| 4,880,752 A | 11/1989 | Keck et al. |
| 4,882,288 A | 11/1989 | North et al. |
| 4,921,805 A | 5/1990 | Gebeyehu et al. |
| 4,931,384 A | 6/1990 | Layton et al. |
| 4,937,048 A | 6/1990 | Sakai et al. |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason et al. |
| 5,028,545 A | 7/1991 | Soini |
| 5,030,558 A | 7/1991 | Litman et al. |
| 5,033,826 A | 7/1991 | Kolner |
| 5,048,139 A | 9/1991 | Matsumi |
| 5,065,008 A | 11/1991 | Hakamata et al. |
| 5,067,155 A | 11/1991 | Bianco et al. |
| 5,081,012 A | 1/1992 | Flanagan et al. |
| 5,089,387 A | 2/1992 | Tsay et al. |
| 5,090,807 A | 2/1992 | Tai |
| 5,091,636 A | 2/1992 | Takada et al. |
| 5,095,194 A | 3/1992 | Barbanell |
| 5,100,238 A | 3/1992 | Nailor et al. |
| 5,104,209 A | 4/1992 | Hill et al. |
| 5,105,305 A | 4/1992 | Betzig et al. |
| 5,114,864 A | 5/1992 | Walt |
| 5,115,121 A | 5/1992 | Bianco et al. |
| 5,118,608 A | 6/1992 | Layton et al. |
| 5,129,974 A | 7/1992 | Aurenius |
| 5,138,468 A | 8/1992 | Barbanell |
| 5,141,848 A | 8/1992 | Donovan et al. |
| 5,143,853 A | 9/1992 | Walt |
| 5,144,461 A | 9/1992 | Horan |
| 5,160,701 A | 11/1992 | Brown, III et al. |
| 5,166,813 A | 11/1992 | Metz |
| 5,192,980 A | 3/1993 | Dixon et al. |
| 5,196,350 A | 3/1993 | Backman et al. |
| 5,200,794 A | 4/1993 | Nishiguma et al. |
| 5,218,594 A | 6/1993 | Tanno |
| 5,239,178 A | 8/1993 | Derndinger et al. |
| 5,244,636 A | 9/1993 | Walt et al. |
| 5,283,777 A | 2/1994 | Tanno et al. |
| 5,291,006 A | 3/1994 | Nishiguma et al. |
| 5,291,027 A | 3/1994 | Kita et al. |
| 5,300,764 A | 4/1994 | Hoshino et al. |
| 5,307,332 A | 4/1994 | Tinet |
| 5,310,686 A | 5/1994 | Sawyers et al. |
| 5,329,352 A | 7/1994 | Jacobsen |
| 5,342,790 A | 8/1994 | Levine et al. |
| 5,349,442 A | 9/1994 | Deason et al. |
| 5,352,582 A | 10/1994 | Lichtenwalter et al. |
| 5,364,797 A | 11/1994 | Olson et al. |
| 5,367,588 A | 11/1994 | Hill et al. |
| 5,372,783 A | 12/1994 | Lackie |
| 5,374,816 A | 12/1994 | Bianco |
| 5,374,818 A | 12/1994 | Bianco et al. |
| 5,388,173 A | 2/1995 | Glenn |
| 5,394,234 A | 2/1995 | Bianco et al. |
| 5,395,558 A | 3/1995 | Tsai |
| 5,410,147 A | 4/1995 | Riza |
| 5,426,297 A | 6/1995 | Dunphy et al. |
| 5,432,329 A | 7/1995 | O'Boyle et al. |
| 5,442,433 A | 8/1995 | Hoshino et al. |
| 5,448,659 A | 9/1995 | Tsutsui et al. |
| 5,451,528 A | 9/1995 | Raymoure et al. |
| 5,455,178 A | 10/1995 | Fattinger |
| 5,461,475 A | 10/1995 | Lerner et al. |
| 5,465,176 A | 11/1995 | Bianco et al. |
| 5,468,649 A | 11/1995 | Shah et al. |
| 5,472,515 A | 12/1995 | Roberts |
| 5,506,674 A | 4/1996 | Inoue et al. |
| 5,514,785 A | 5/1996 | Van Ness et al. |
| 5,528,045 A | 6/1996 | Hoffman et al. |
| 5,547,849 A | 8/1996 | Baer et al. |
| 5,559,613 A | 9/1996 | Deveaud-Pledran et al. |
| 5,585,639 A | 12/1996 | Dorsel et al. |
| 5,587,832 A | 12/1996 | Krause |
| 5,607,188 A | 3/1997 | Bahns et al. |
| 5,610,287 A | 3/1997 | Nikiforov et al. |
| 5,620,853 A | 4/1997 | Smethers et al. |
| 5,621,515 A | 4/1997 | Hoshino |
| 5,624,850 A | 4/1997 | Kumar et al. |
| 5,625,472 A | 4/1997 | Mizrahi et al. |
| 5,627,040 A | 5/1997 | Bierre et al. |
| 5,627,663 A | 5/1997 | Horan et al. |
| 5,633,724 A | 5/1997 | King et al. |
| 5,633,790 A | 5/1997 | Gritter et al. |
| 5,633,975 A | 5/1997 | Gary et al. |
| 5,667,976 A | 9/1997 | Van Ness et al. |
| 5,671,308 A | 9/1997 | Inoue et al. |
| 5,682,244 A | 10/1997 | Barlow et al. |
| 5,712,912 A | 1/1998 | Tomko et al. |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins et al. |
| 5,745,617 A | 4/1998 | Starodubov et al. |
| 5,759,778 A | 6/1998 | Li et al. |
| 5,760,961 A | 6/1998 | Tompkin et al. |
| 5,766,956 A | 6/1998 | Groger et al. |
| 5,771,251 A | 6/1998 | Kringlebotn et al. |
| 5,776,694 A | 7/1998 | Sheiness et al. |
| 5,793,502 A | 8/1998 | Bianco et al. |
| 5,798,273 A | 8/1998 | Shuler et al. |
| 5,799,231 A | 8/1998 | Gates et al. |
| 5,801,857 A | 9/1998 | Heckenkamp et al. |
| 5,804,384 A | 9/1998 | Muller et al. |
| 5,812,272 A | 9/1998 | King et al. |
| 5,824,472 A | 10/1998 | Betlach et al. |
| 5,824,478 A | 10/1998 | Muller |
| 5,824,557 A | 10/1998 | Burke et al. |
| 5,830,622 A | 11/1998 | Canning et al. |
| 5,831,698 A | 11/1998 | Depp et al. |
| 5,837,475 A | 11/1998 | Dorsal et al. |
| 5,837,552 A | 11/1998 | Cotton et al. |
| 5,841,555 A | 11/1998 | Bianco et al. |

| | | | | | | |
|---|---|---|---|---|---|---|
| 5,846,737 | A | 12/1998 | Kang | 6,313,771 B1 | 11/2001 | Munroe et al. |
| 5,861,113 | A | 1/1999 | Choquette et al. | 6,314,220 B1 | 11/2001 | Mossberg et al. |
| 5,874,187 | A | 2/1999 | Colvin et al. | 6,319,668 B1 | 11/2001 | Nova et al. |
| 5,881,197 | A | 3/1999 | Dong et al. | 6,321,007 B1 | 11/2001 | Sanders |
| 5,895,750 | A | 4/1999 | Mushahwar et al. | 6,322,932 B1 | 11/2001 | Colvin et al. |
| 5,922,550 | A | 7/1999 | Everhart et al. | 6,328,209 B1 | 12/2001 | O'Boyle |
| 5,922,617 | A | 7/1999 | Wang et al. | 6,329,963 B1 | 12/2001 | Chiabrera et al. |
| 5,925,562 | A | 7/1999 | Nova et al. | 6,331,273 B1 | 12/2001 | Nova et al. |
| 5,925,878 | A | 7/1999 | Challener | 6,335,824 B1 | 1/2002 | Overbeck |
| 5,945,679 | A | 8/1999 | Dorsel et al. | 6,340,588 B1 | 1/2002 | Nova et al. |
| 5,972,542 | A | 10/1999 | Starodubov | 6,344,298 B1 | 2/2002 | Starodubov et al. |
| 5,976,896 | A | 11/1999 | Kumar et al. | 6,352,854 B1 | 3/2002 | Nova et al. |
| 5,981,166 | A | 11/1999 | Mandecki | 6,355,198 B1 | 3/2002 | Kim et al. |
| 5,986,838 | A | 11/1999 | Thomas, III | 6,355,432 B1 | 3/2002 | Fodor et al. |
| 5,989,923 | A | 11/1999 | Lowe et al. | 6,356,681 B1 | 3/2002 | Chen et al. |
| 5,992,742 | A | 11/1999 | Sullivan | 6,359,734 B1 | 3/2002 | Staub et al. |
| 5,998,796 | A | 12/1999 | Liu et al. | 6,361,958 B1 | 3/2002 | Shieh et al. |
| 6,001,510 | A | 12/1999 | Meng et al. | 6,363,097 B1 | 3/2002 | Linke et al. |
| 6,005,691 | A | 12/1999 | Grot et al. | 6,371,370 B2 | 4/2002 | Sadler et al. |
| 6,017,754 | A | 1/2000 | Chesnut et al. | 6,372,428 B1 | 4/2002 | Nova et al. |
| 6,025,129 | A | 2/2000 | Nova et al. | 6,383,754 B1 | 5/2002 | Kaufman et al. |
| 6,025,283 | A | 2/2000 | Roberts | 6,391,562 B2 | 5/2002 | Kambara et al. |
| 6,027,694 | A | 2/2000 | Boulton et al. | 6,395,558 B1 | 5/2002 | Duveneck et al. |
| 6,030,581 | A | 2/2000 | Virtanen | 6,399,295 B1 | 6/2002 | Kaylor et al. |
| 6,035,082 | A | 3/2000 | Murphy et al. | 6,399,935 B1 | 6/2002 | Jovin et al. |
| 6,035,083 | A | 3/2000 | Brennan et al. | 6,403,320 B1 | 6/2002 | Read et al. |
| 6,036,807 | A | 3/2000 | Brongers | 6,406,841 B1 | 6/2002 | Lee et al. |
| 6,043,880 | A | 3/2000 | Andrews et al. | 6,406,848 B1 | 6/2002 | Bridgham et al. |
| 6,046,925 | A | 4/2000 | Tsien et al. | 6,416,714 B1 | 7/2002 | Nova et al. |
| 6,049,727 | A | 4/2000 | Crothall | 6,416,952 B1 | 7/2002 | Pirrung et al. |
| 6,057,107 | A | 5/2000 | Fulton | 6,417,010 B1 | 7/2002 | Cargill et al. |
| 6,060,256 | A | 5/2000 | Everhart et al. | 6,424,056 B1 | 7/2002 | Irvin |
| 6,067,167 | A | 5/2000 | Atkinson et al. | 6,428,707 B1 | 8/2002 | Berg et al. |
| 6,067,392 | A | 5/2000 | Wakami et al. | 6,428,957 B1 | 8/2002 | Delenstarr |
| 6,078,048 | A | 6/2000 | Stevens et al. | 6,429,022 B1 | 8/2002 | Kunz et al. |
| 6,084,995 | A | 7/2000 | Clements et al. | 6,433,849 B1 | 8/2002 | Lowe |
| 6,087,186 | A | 7/2000 | Cargill et al. | 6,436,651 B1 | 8/2002 | Everhart et al. |
| 6,088,503 | A | 7/2000 | Chandler et al. | 6,440,667 B1 | 8/2002 | Fodor et al. |
| 6,096,496 | A | 8/2000 | Frankel et al. | 6,456,762 B1 | 9/2002 | Nishiki et al. |
| 6,096,596 | A | 8/2000 | Gonzalez | 6,462,770 B1 | 10/2002 | Cline et al. |
| 6,097,485 | A | 8/2000 | Lievan | 6,489,606 B1 | 12/2002 | Kersey et al. |
| 6,103,535 | A | 8/2000 | Pilevar et al. | 6,496,287 B1 | 12/2002 | Seiberle et al. |
| 6,118,127 | A | 9/2000 | Liu et al. | 6,506,342 B1 | 1/2003 | Frankel |
| 6,128,077 | A | 10/2000 | Jovin et al. | 6,514,767 B1 | 2/2003 | Natan |
| 6,137,931 | A | 10/2000 | Ishikawa et al. | 6,515,753 B2 | 2/2003 | Maher et al. |
| 6,143,247 | A | 11/2000 | Sheppard, Jr. et al. | 6,522,406 B1 | 2/2003 | Rovira et al. |
| 6,156,501 | A | 12/2000 | McGall et al. | 6,524,793 B1 | 2/2003 | Chandler et al. |
| 6,159,748 | A | 12/2000 | Hechinger | 6,533,183 B2 | 3/2003 | Aasmul et al. |
| 6,160,240 | A | 12/2000 | Momma et al. | 6,542,673 B1 | 4/2003 | Holter et al. |
| 6,160,656 | A | 12/2000 | Mossberg et al. | 6,544,739 B1 | 4/2003 | Fodor et al. |
| 6,164,548 | A | 12/2000 | Curiel | 6,545,758 B1 | 4/2003 | Sandstrom |
| 6,165,592 | A | 12/2000 | Berger et al. | 6,552,809 B1 | 4/2003 | Bergeron |
| 6,165,648 | A | 12/2000 | Colvin et al. | 6,560,017 B1 | 5/2003 | Bianco |
| 6,174,648 | B1 | 1/2001 | Terao et al. | 6,565,770 B1 | 5/2003 | Mayer et al. |
| 6,194,563 | B1 | 2/2001 | Cruickshank | 6,573,523 B1 | 6/2003 | Long |
| 6,204,068 | B1 | 3/2001 | Soini et al. | 6,576,424 B2 | 6/2003 | Fodor et al. |
| 6,204,969 | B1 | 3/2001 | Jang | 6,578,712 B2 | 6/2003 | Lawandy |
| 6,214,560 | B1 | 4/2001 | Yguerabide et al. | 6,592,036 B2 | 7/2003 | Sadler et al. |
| 6,218,194 | B1 | 4/2001 | Lyndin et al. | 6,594,421 B1 | 7/2003 | Johnson et al. |
| 6,221,579 | B1 | 4/2001 | Everhart et al. | 6,609,728 B1 | 8/2003 | Voerman et al. |
| 6,229,635 | B1 | 5/2001 | Wulf | 6,613,581 B1 | 9/2003 | Wada et al. |
| 6,229,827 | B1 | 5/2001 | Fernald et al. | 6,618,342 B1 | 9/2003 | Johnson et al. |
| 6,229,941 | B1 | 5/2001 | Yoon et al. | 6,622,916 B1 | 9/2003 | Bianco |
| 6,242,056 | B1 | 6/2001 | Spencer et al. | 6,628,439 B2 | 9/2003 | Shiozawa et al. |
| 6,259,450 | B1 | 7/2001 | Chiabrera et al. | 6,632,655 B1 | 10/2003 | Mehta et al. |
| 6,262,846 | B1 | 7/2001 | Nakai | 6,635,470 B1 | 10/2003 | Vann |
| 6,268,128 | B1 | 7/2001 | Collins et al. | 6,635,863 B1 | 10/2003 | Nihommori et al. |
| 6,277,628 | B1 | 8/2001 | Johann et al. | 6,646,243 B2 | 11/2003 | Pirrung et al. |
| 6,284,437 | B1 | 9/2001 | Kashyap | 6,657,758 B1 | 12/2003 | Garner |
| 6,284,459 | B1 | 9/2001 | Nova et al. | 6,660,147 B1 | 12/2003 | Woudenberg et al. |
| 6,285,806 | B1 | 9/2001 | Kersey et al. | 6,678,429 B2 | 1/2004 | Mossberg et al. |
| 6,288,220 | B1 | 9/2001 | Kambara et al. | 6,689,316 B1 | 2/2004 | Blyth et al. |
| 6,292,282 | B1 | 9/2001 | Mossberg et al. | 6,692,031 B2 | 2/2004 | McGrew |
| 6,292,319 | B1 | 9/2001 | Thomas, III | 6,692,912 B1 | 2/2004 | Boles et al. |
| 6,301,047 | B1 | 10/2001 | Hoshino et al. | 6,708,618 B1 | 3/2004 | Tsai |
| 6,304,263 | B1 | 10/2001 | Chiabrera et al. | 6,750,941 B2 | 6/2004 | Satoh et al. |
| 6,306,587 | B1 | 10/2001 | Royer et al. | 6,794,658 B2 | 9/2004 | MacAulay |
| 6,309,601 | B1 | 10/2001 | Juncosa et al. | 6,806,954 B2 | 10/2004 | Sandstrom |
| 6,312,961 | B1 | 11/2001 | Voirin et al. | 6,858,184 B2 | 2/2005 | Pelrine |

| | | |
|---|---|---|
| 6,874,639 B2 | 4/2005 | Lawandy |
| 6,881,789 B2 | 4/2005 | Bossé |
| 6,892,001 B2 | 5/2005 | Ohta et al. |
| 6,905,885 B2 | 6/2005 | Colston et al. |
| 6,908,737 B2 | 6/2005 | Ravkin et al. |
| 6,919,009 B2 | 7/2005 | Stonas |
| 6,972,883 B2 | 12/2005 | Fujii et al. |
| 6,982,996 B1 | 1/2006 | Putnam et al. |
| 7,014,815 B1 | 3/2006 | Worthington et al. |
| 7,045,049 B1 | 5/2006 | Natan |
| 7,065,032 B2 | 6/2006 | Horimai |
| 7,080,857 B2 | 7/2006 | Patton |
| 7,092,160 B2 | 8/2006 | Putnam et al. |
| 7,106,513 B2 | 9/2006 | Moon et al. |
| 7,122,384 B2 | 10/2006 | Prober |
| 7,126,755 B2 | 10/2006 | Moon et al. |
| 7,164,533 B2 | 1/2007 | Moon |
| 7,190,522 B2 | 3/2007 | Moon |
| 7,215,628 B2 | 5/2007 | Horimai |
| 7,225,082 B1 | 5/2007 | Natan |
| 7,321,541 B2 | 1/2008 | Horimai |
| 7,349,158 B2 * | 3/2008 | Moon et al. ............. 359/569 |
| 7,375,890 B2 * | 5/2008 | Putnam et al. ............ 359/566 |
| 7,399,643 B2 * | 7/2008 | Moon et al. ............. 436/521 |
| 7,433,123 B2 | 10/2008 | Putnam et al. |
| 7,441,703 B2 | 10/2008 | Moon |
| 7,508,608 B2 | 3/2009 | Kersey |
| 7,602,952 B2 | 10/2009 | Kersey |
| 7,604,173 B2 | 10/2009 | Kersey |
| 7,619,819 B2 | 11/2009 | Moon |
| 7,791,802 B2 | 9/2010 | Putnam et al. |
| 7,796,333 B2 | 9/2010 | Kersey et al. |
| 2001/0007775 A1 | 7/2001 | Seul et al. |
| 2001/0020375 A1 | 9/2001 | Novack et al. |
| 2001/0029049 A1 | 10/2001 | Walt |
| 2002/0000471 A1 | 1/2002 | Aasmul et al. |
| 2002/0006664 A1 | 1/2002 | Sabatini |
| 2002/0018430 A1 | 2/2002 | Heckenkamp et al. |
| 2002/0022273 A1 | 2/2002 | Empedocles et al. |
| 2002/0025534 A1 | 2/2002 | Goh et al. |
| 2002/0031783 A1 | 3/2002 | Empedocles |
| 2002/0034747 A1 | 3/2002 | Bruchez et al. |
| 2002/0039728 A1 | 4/2002 | Kain |
| 2002/0039732 A1 | 4/2002 | Bruchez et al. |
| 2002/0074513 A1 | 6/2002 | Abel et al. |
| 2002/0084329 A1 | 7/2002 | Kaye et al. |
| 2002/0090650 A1 | 7/2002 | Empedocles et al. |
| 2002/0094528 A1 | 7/2002 | Salafsky |
| 2002/0097658 A1 | 7/2002 | Worthington et al. |
| 2002/0155490 A1 | 10/2002 | Skinner et al. |
| 2002/0174918 A1 | 11/2002 | Fujimura et al. |
| 2002/0197456 A1 | 12/2002 | Pope |
| 2003/0008323 A1 | 1/2003 | Ravkin et al. |
| 2003/0021003 A1 | 1/2003 | Ono et al. |
| 2003/0032203 A1 | 2/2003 | Sabatini et al. |
| 2003/0077038 A1 | 4/2003 | Murashima et al. |
| 2003/0082568 A1 | 5/2003 | Phan |
| 2003/0082587 A1 | 5/2003 | Seul et al. |
| 2003/0129654 A1 | 7/2003 | Ravkin et al. |
| 2003/0138208 A1 | 7/2003 | Pawlak et al. |
| 2003/0142704 A1 | 7/2003 | Lawandy |
| 2003/0142713 A1 | 7/2003 | Lawandy |
| 2003/0153006 A1 | 8/2003 | Washizu et al. |
| 2003/0162296 A1 | 8/2003 | Lawandy |
| 2003/0184730 A1 | 10/2003 | Price |
| 2003/0203390 A1 | 10/2003 | Kaye et al. |
| 2003/0228610 A1 | 12/2003 | Seul |
| 2004/0027968 A1 | 2/2004 | Horimai |
| 2004/0047030 A1 | 3/2004 | MacAulay |
| 2004/0062178 A1 | 4/2004 | Horimai |
| 2004/0075907 A1 | 4/2004 | Moon et al. |
| 2004/0100636 A1 | 5/2004 | Somekh et al. |
| 2004/0100892 A1 | 5/2004 | Horimai |
| 2004/0125370 A1 | 7/2004 | Montagu |
| 2004/0125424 A1 | 7/2004 | Moon et al. |
| 2004/0126875 A1 | 7/2004 | Putnam et al. |
| 2004/0132205 A1 | 7/2004 | Moon et al. |
| 2004/0156471 A1 | 8/2004 | Sakata |
| 2004/0170356 A1 | 9/2004 | Iazikov et al. |
| 2004/0175842 A1 | 9/2004 | Roitman et al. |
| 2004/0209376 A1 | 10/2004 | Natan et al. |
| 2004/0233485 A1 | 11/2004 | Moon et al. |
| 2004/0263923 A1 | 12/2004 | Moon et al. |
| 2005/0042764 A1 | 2/2005 | Sailor et al. |
| 2005/0056587 A1 | 3/2005 | Allen |
| 2005/0220408 A1 | 10/2005 | Putnam |
| 2005/0227252 A1 | 10/2005 | Moon et al. |
| 2005/0270603 A1 | 12/2005 | Putnam et al. |
| 2006/0023310 A1 | 2/2006 | Putnam et al. |
| 2006/0028727 A1 | 2/2006 | Moon et al. |
| 2006/0050544 A1 | 3/2006 | Horimai |
| 2006/0057729 A1 | 3/2006 | Moon et al. |
| 2006/0063271 A1 | 3/2006 | Putnam et al. |
| 2006/0067179 A1 | 3/2006 | Matsumoto |
| 2006/0071075 A1 | 4/2006 | Moon et al. |
| 2006/0072177 A1 | 4/2006 | Putnam et al. |
| 2006/0118630 A1 | 6/2006 | Kersey et al. |
| 2006/0119913 A1 | 6/2006 | Moon |
| 2006/0132877 A1 | 6/2006 | Kersey |
| 2006/0134324 A1 | 6/2006 | Putnam et al. |
| 2006/0139635 A1 | 6/2006 | Kersey et al. |
| 2006/0140074 A1 | 6/2006 | Horimai |
| 2006/0160208 A1 | 7/2006 | Putnam et al. |
| 2007/0121181 A1 | 5/2007 | Moon et al. |
| 2007/0236789 A1 | 10/2007 | Moon |
| 2008/0085565 A1 | 4/2008 | Moon |
| 2008/0129990 A1 | 6/2008 | Moon |
| 2008/0165656 A1 | 7/2008 | Moon et al. |
| 2008/0170664 A1 | 7/2008 | Kalman |
| 2008/0192311 A1 | 8/2008 | Horimai |
| 2009/0034078 A1 | 2/2009 | Putnam |
| 2009/0040885 A1 | 2/2009 | Horimai |
| 2009/0073520 A1 | 3/2009 | Kersey |
| 2009/0194589 A1 | 8/2009 | Moon et al. |
| 2010/0025482 A1 | 2/2010 | Moon |
| 2010/0072278 A1 | 3/2010 | Putnam |
| 2010/0099574 A1 | 4/2010 | Moon |

FOREIGN PATENT DOCUMENTS

| | | |
|---|---|---|
| DE | 2416652 | 10/1975 |
| EP | 0 395 300 | 10/1990 |
| EP | 0 485 803 | 5/1992 |
| EP | 0 508 257 | 10/1992 |
| EP | 0 723 149 | 7/1996 |
| EP | 0 798 573 A1 | 10/1997 |
| EP | 0 911 667 A1 | 4/1999 |
| EP | 0 916 981 | 5/1999 |
| EP | 0 972 817 A1 | 1/2000 |
| EP | 1 182 054 A2 | 2/2002 |
| EP | 1 219 979 A1 | 7/2002 |
| GB | 2 118 189 | 10/1983 |
| GB | 2 129 551 | 5/1984 |
| GB | 2 138 821 | 10/1984 |
| GB | 2 299 235 | 9/1996 |
| GB | 2 306 484 | 5/1997 |
| GB | 2 319 838 | 6/1998 |
| GB | 2 372 100 | 8/2002 |
| JP | 58143254 | 8/1983 |
| JP | 58143254 A | 8/1983 |
| JP | 08102544 | 4/1986 |
| JP | 01047950 | 2/1989 |
| JP | 05307119 | 11/1993 |
| JP | 06333102 | 2/1994 |
| JP | 06333102 | 12/1994 |
| JP | 08102544 | 4/1996 |
| JP | 08272923 | 10/1996 |
| JP | 10160705 | 6/1998 |
| JP | 10166075 | 6/1998 |
| JP | 11-119029 | 4/1999 |
| JP | 11119029 | 4/1999 |
| JP | 2000-035521 | 2/2000 |
| JP | 00249706 | 9/2000 |
| JP | 2000249706 | 9/2000 |
| JP | 200191715 | 4/2001 |
| JP | 2002182022 | 2/2002 |
| JP | 2002513166 | 5/2002 |
| JP | 22182022 | 6/2002 |
| JP | 200300467 A | 1/2003 |

| | | |
|---|---|---|
| JP | 2003004671 | 8/2003 |
| WO | WO 91/06496 | 5/1991 |
| WO | WO 93/09668 | 5/1993 |
| WO | WO 94/28119 | 12/1994 |
| WO | WO 96/24061 | 8/1996 |
| WO | WO 96/36436 A1 | 11/1996 |
| WO | WO 97/12680 | 4/1997 |
| WO | WO 97/015690 | 5/1997 |
| WO | WO 97/17258 | 5/1997 |
| WO | WO 97/31282 | 8/1997 |
| WO | WO 97/34171 | 9/1997 |
| WO | WO 98/04740 | 2/1998 |
| WO | WO 98/24549 | 6/1998 |
| WO | WO 99/02266 | 1/1999 |
| WO | WO 99/09042 | 2/1999 |
| WO | WO 99/32654 | 7/1999 |
| WO | WO 99/42209 | 8/1999 |
| WO | WO 00/08443 | 2/2000 |
| WO | WO 00/16893 A2 | 3/2000 |
| WO | WO 00/19262 | 6/2000 |
| WO | WO 00/37914 | 6/2000 |
| WO | WO 00/37969 | 6/2000 |
| WO | WO 00/39617 | 7/2000 |
| WO | WO 00/61198 | 10/2000 |
| WO | WO 00/63419 | 10/2000 |
| WO | WO 01/58583 A1 | 8/2001 |
| WO | WO 01/71322 A2 | 9/2001 |
| WO | WO 01/78889 A2 | 10/2001 |
| WO | WO 01/90225 | 11/2001 |
| WO | WO 02/059306 A2 | 8/2002 |
| WO | WO 02/059603 | 8/2002 |
| WO | WO 03/061983 | 7/2003 |
| WO | WO 2004/019276 A1 | 3/2004 |
| WO | WO 2004/024328 | 3/2004 |
| WO | WO 2004/025561 | 3/2004 |
| WO | WO 2004/025562 | 3/2004 |
| WO | WO 2004/025563 A1 | 3/2004 |
| WO | WO 2004/034012 | 4/2004 |
| WO | WO 2004/066210 | 8/2004 |
| WO | WO 2005/026729 A3 | 3/2005 |
| WO | WO 2005/027031 A2 | 3/2005 |
| WO | WO 2005/029047 A2 | 3/2005 |
| WO | WO 2005/033681 A1 | 4/2005 |
| WO | WO 2005/050207 A3 | 6/2005 |
| WO | WO 2005/079544 A2 | 9/2005 |
| WO | WO 2006/020363 A2 | 2/2006 |
| WO | WO 2006/055735 A2 | 5/2006 |
| WO | WO 2006/055736 A1 | 5/2006 |
| WO | WO 2006/076053 A1 | 7/2006 |

PUBLICATIONS

Hideki Kambara; Recent Progress in fluorescent DNA Analyzers and Methods; Current Topics in Analytical checmistry; vol. 1, (1998) pp. 21-36.

G. Kakarantzas et al.;"Transmission Filters Based on periodically Micro-tapered Fibre"; CLE0/2000/Friday Morning; 8:45 a.m.; pp. 574-575.

Michael C. Needels et al.; "Generation and Screening of an Oligonucleotide-Encoded Synthetic Peptide Library"; Proc Natl. Acad. Sci. USA, vol. 90;pp. 10700-10704, Nov. 1993.

W.R. Rigby; "An Anodizing Process for the Production of Inorganic Microfiltration Membranes"; 2436Transactions of the Institute of Metal Finishing;68(Aug. 1990),Part 3 p. 95-98.

U.S. 6,780,301, 08/2004, Natan (withdrawn).

Burstein Technology, Inc.; "Angel Strategies Tombstone"; 1 pg.

Vander Lugt; "Design Relationships for Holographic Memories"; Applied Optics, vol. 12, No. 7, Jul. 1973; pp. 1675-1685.

Andrew Marshall; "DNA Chips: Array of Possibilities"; Nature Biotechnology vol. 16 Jan. 1998; pp. 27-31.

Thomas Laurell; "Enhanced Enzyme Activity in Silicon Integrated Enzyme Reactors Utilizing Porous Silicon as the Coupling Matrix"; Sensor & Actuators B 31 (1996); pp. 161-166.

Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.

Masato Mitsuhashi; "Gene Manipulation on Plastic Plates"; Nature, vol. 357, Jun. 11, 1992; pp. 519-520.

"Ben Beune Patent Licensing Director of Philips IP&S"; Replication & Duplication—News & Technology; Jan.-Feb. 2002; pp. 1-2.

"Compact Disc Arrayer"; V&P Scientific; Nov. 17, 2003; pp. 1-4.

De Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.

Fonjallaz et al., "Interferometric Side Diffraction Technique for the Characterisation of Fiber Gratings"; 1999 OSA Conference, Sep. 23-25; 3 pgs.

Kashyap R.; "Fiber Bragg Gratings"; Academic Press, Ch. 9; pp. 430-433.

Kogelnik H; "Coupled Wave Theory for Thick Hologram Gratings"; The Bell System Technical Journal, 48(9):2909-2947 (1969).

Krug P., "Measurement of Index Modulation Along an Optical Fiber Bragg Grating"; Optics Letters, 20(17):1767-1769.

Leith et al., "Holographic Data Storage in Three-Dimensional Media"; Applied Optics, vol. 5, No. 8, Aug. 1966; 21 pgs.

Shelia R. Nicerwarner-Peña, "Submicrometer Metallic Barcodes"; Science, vol. 294; Oct. 5, 2001; 5 pgs.

Ivan Oransky; "Sequencing on Compact Disc? Microgenomics of Breast Cancer; Better Binding Site Prediction"; vol. 17 / Issue 13 / 35 / Jun. 30, 2003; 13 pgs.

Mark O. Worthington; "Curriculum Vitae"; Jan. 5, 2004; 4 pgs.

Yoshinobu Kohara; "DNA Probes on Beads Arrayed in a Capillary, 'Bead-Array',Exhibited High Hybridization Performance"; Nucleic Acids Research, 2002, vol. 30, No. 16 e87; 7 pgs.

Jain KK, Nanodiagnostics: application of nanotechnology in molecular diagnostics, Expert Review of Molecular Diagnostics 3(2):153-161 (2003), XP008038849.

Othonos, X. Lee; Superimposed Multiple Bragg Gratings, Nov. 10, 1994, vol. 30, No. 23.

Po Ki Yuen, Microbarcode Sorting Device; Science & Technology, Corning Incorparated, Corning, New York 14831-0007, USA.

International Search Report and Preliminary Examination Report for International Application No. PCT/US2003/26315.

International Search Report and Written Opinion for International Application No. PCT/US2003/26316.

International Search Report for International Application No. PCT/US2003/28862.

International Search Report for International Application No. PCT/US2003/28874.

International Search Report for International Application No. PCT/US2003/28875.

International Search Report for International Application No. PCT/US2003/28887.

International Search Report for International Application No. PCT/US2003/28890.

International Search Report and Preliminary Examinatoin for International Application No. PCT/US2003/29164.

International Search Report for International Application No. PCT/US2003/29244.

International Search Report and Written Opinion for International Application No. PCT/US2004/01685.

International Search Report and Written Opinion for International Application No. PCT/US2004/30037.

International Search Report and Written Opinion for International Application No. PCT/US2004/30038.

International Search Report and Written Opinion for International Application No. PCT/US2004/30300.

International Search Report and Written Opinion for International Application No. PCT/US2004/32084.

International Search Report and Written Opinion for International Application No. PCT/US2004/38416.

International Search Report and Written Opinion for International Application No. PCT/US2005/05743.

International Search Report and Written Opinion for International Application No. PCT/US2005/05745.

International Search Report and Written Opinion for International Application No. PCT/US2005/26289.

International Search Report and Written Opinion for International Application No. PCT/US2005/33694.

International Search Report and Written Opinion for International Application No. PCT/US2005/41730.

International Search Report and Written Opinion for International Application No. PCT/US2005/41731.

"Introduction to Flow Cytometry: A Learning Guide," BD Biosciences, San Jose, CA, Apr. 2000.

Material Safety Data Sheet Aquaclean 900; Aquabond Technologies (ABT); 1 pg.

Introduction to Flow Cytometry: A Learning Guide, BD Biosciences, San Jose, CA, Apr. 2000.

Lide, David R.; "CRC Handbook of Chemistry and Physics"; 71st Edition; 1990-1991; CRC Press, Inc.; 10 pgs.

Patil, Pradeep et al; "Porous Polystyrene Beads as Carriers for Self-Emulsifying System Containing Loratadine"; Submitted: Jun. 7, 2005; Accepted: Sep. 15, 2005; Published: Mar. 24, 2006; AAPS PharmSciTech 2006; 7 (1) Article 28 (http://www.aapspharmscitech.org); 7 pgs.

* cited by examiner

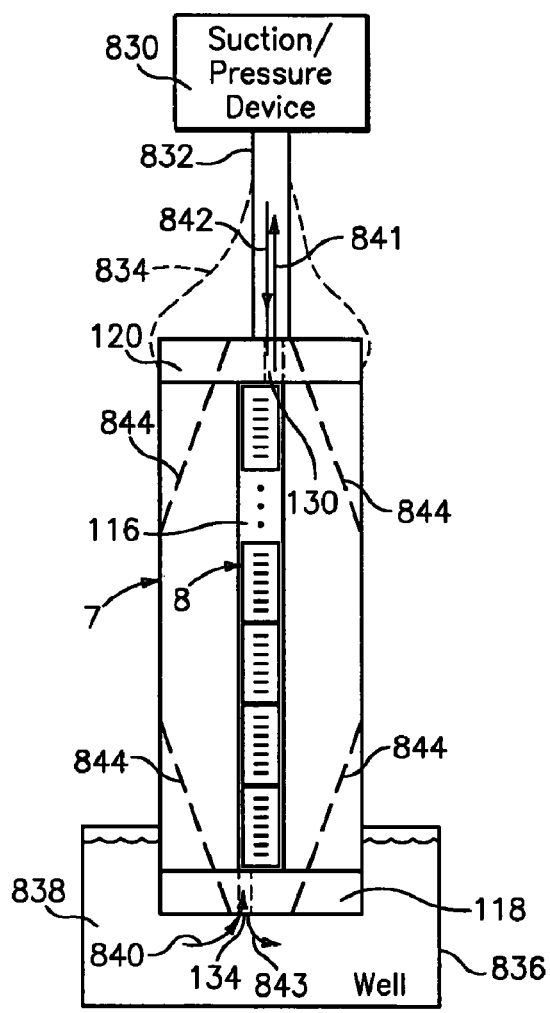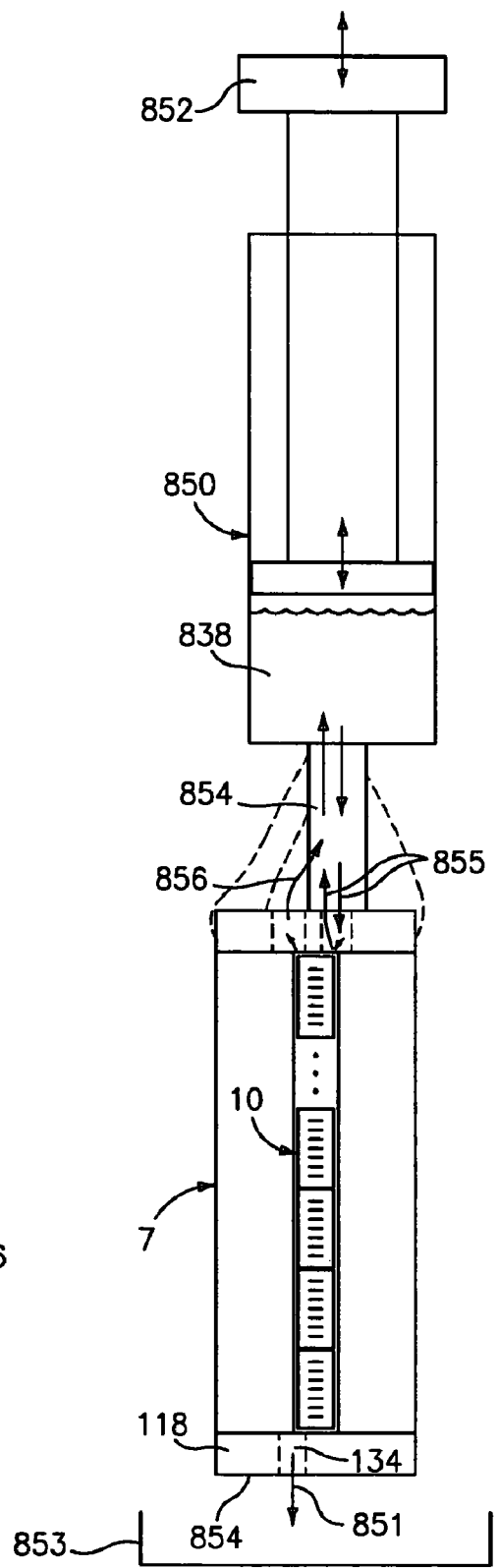
FIG. 2
FIG. 3

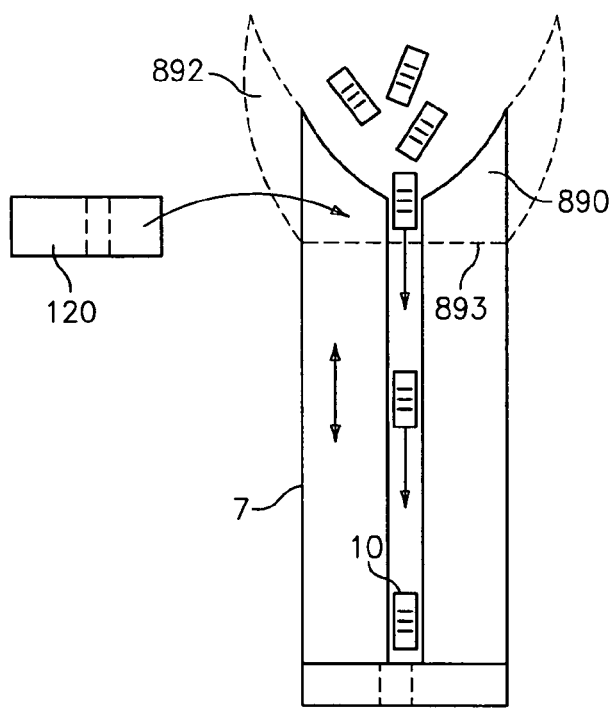
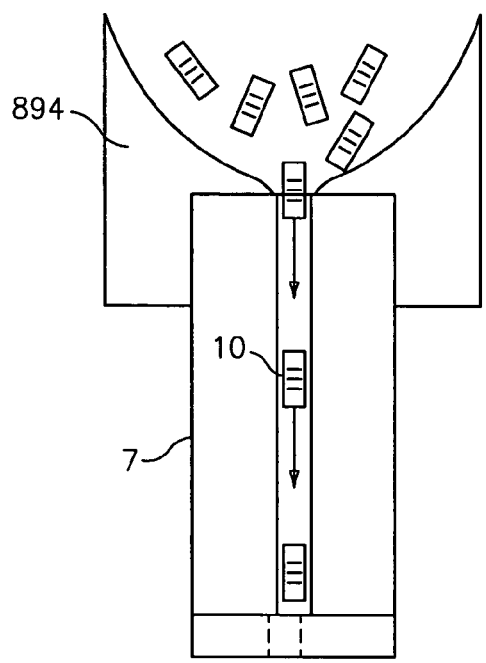
FIG. 14
FIG. 15
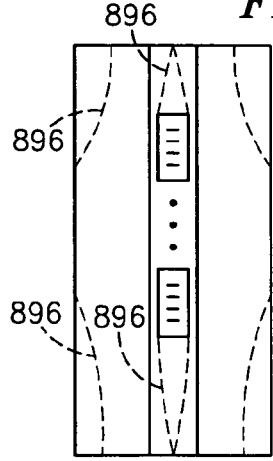
FIG. 16
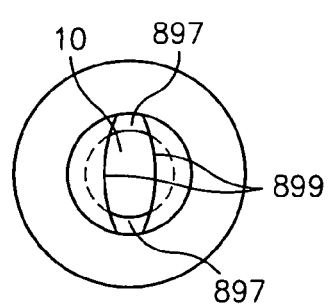
FIG. 17
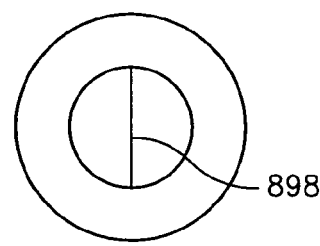
FIG. 18
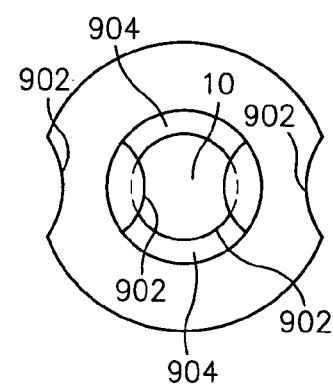
FIG. 20
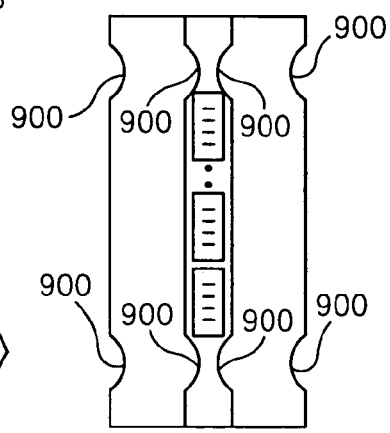
FIG. 19

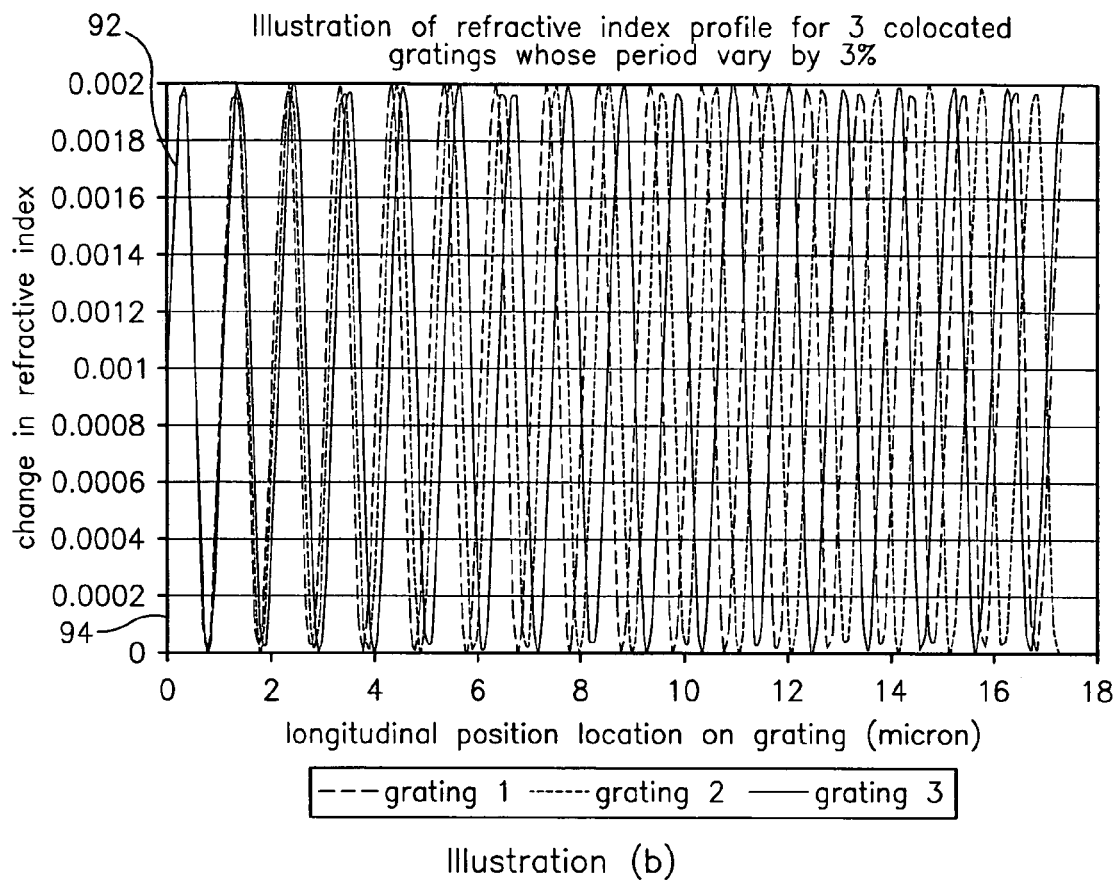
Illustration (b)
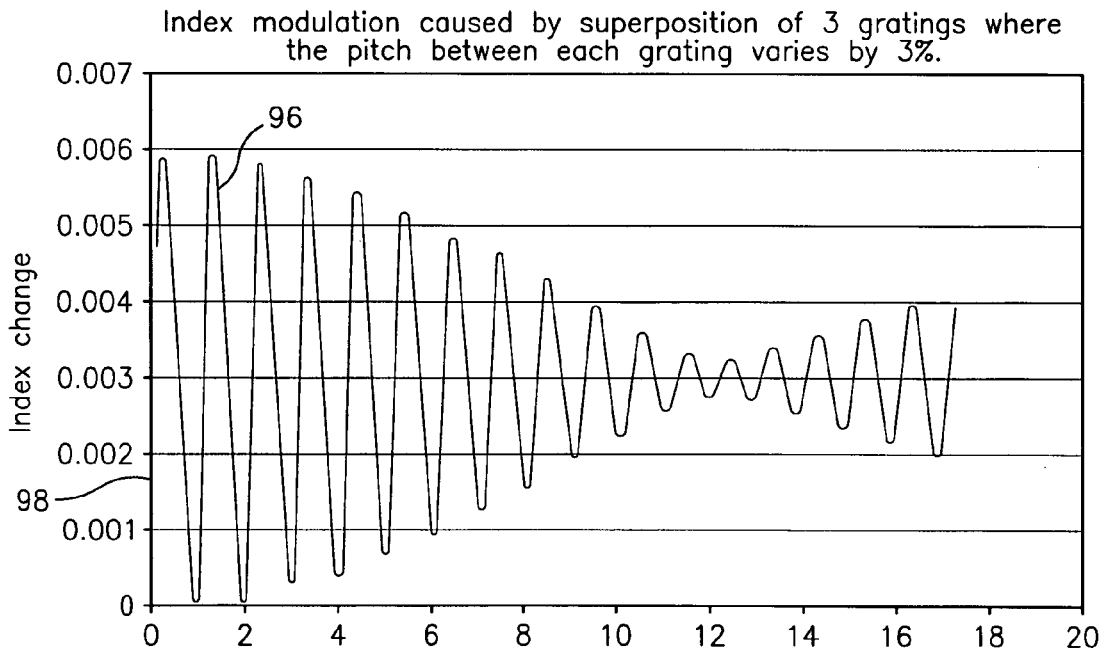
Illustration (d)
FIG. 31

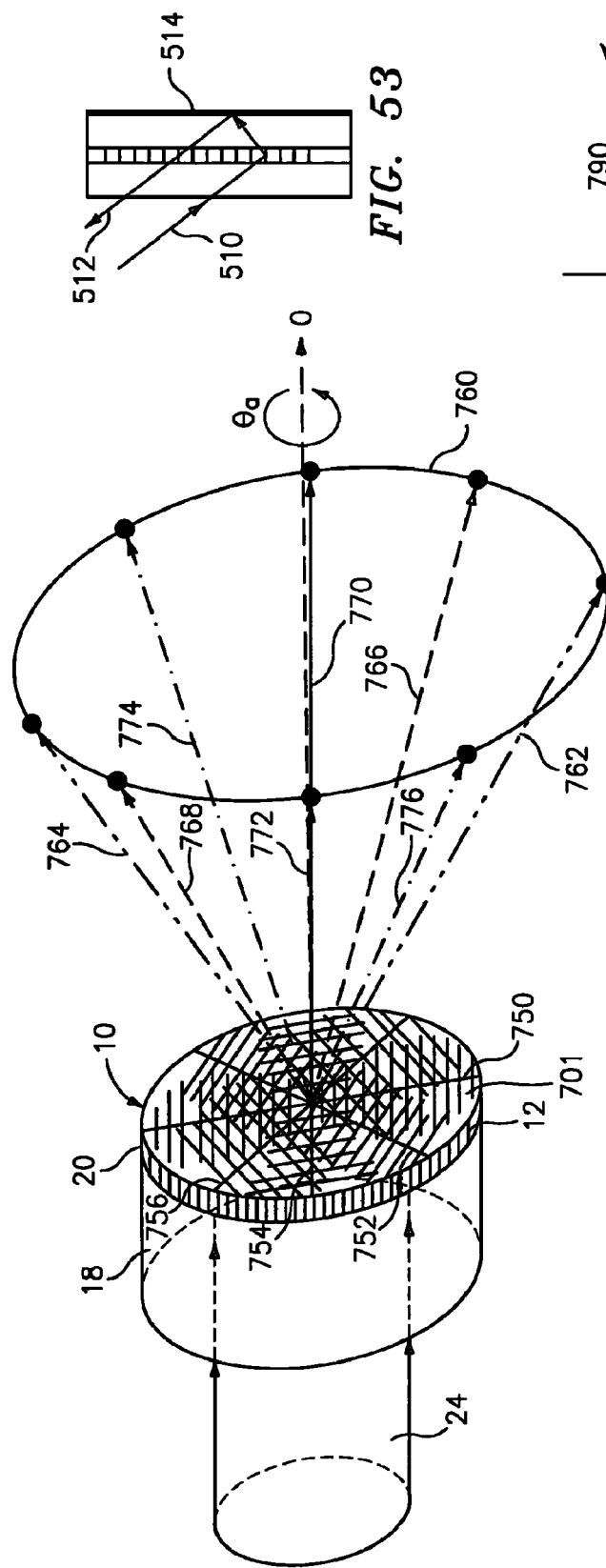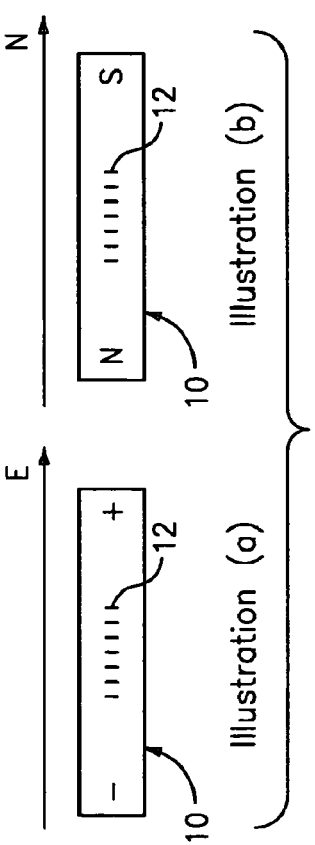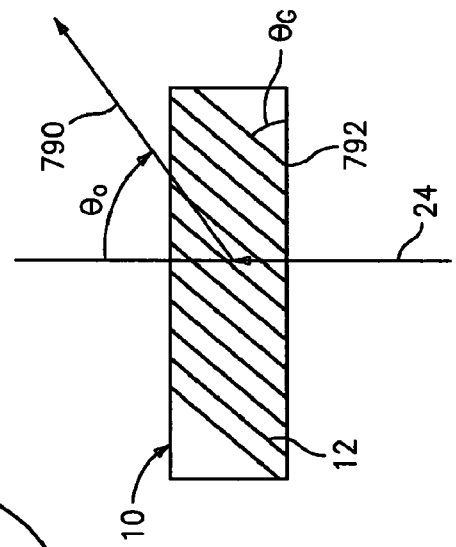

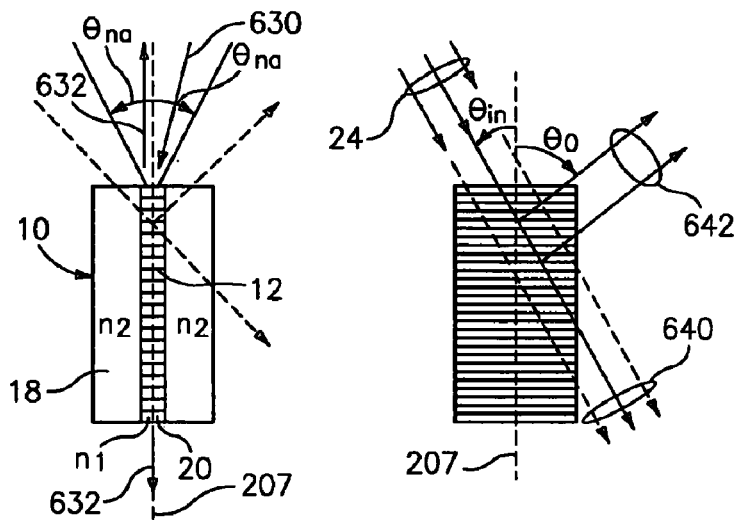
*FIG. 40*                *FIG. 41*
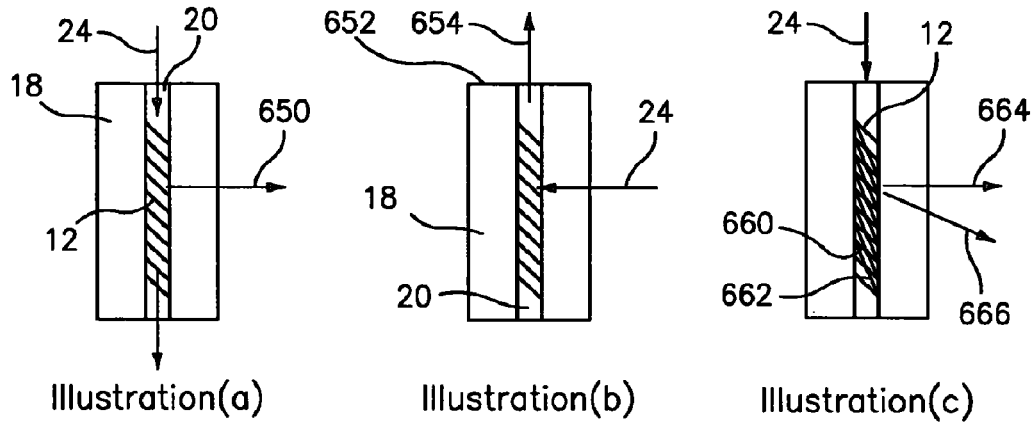
Illustration(a)    Illustration(b)    Illustration(c)
*FIG. 42*
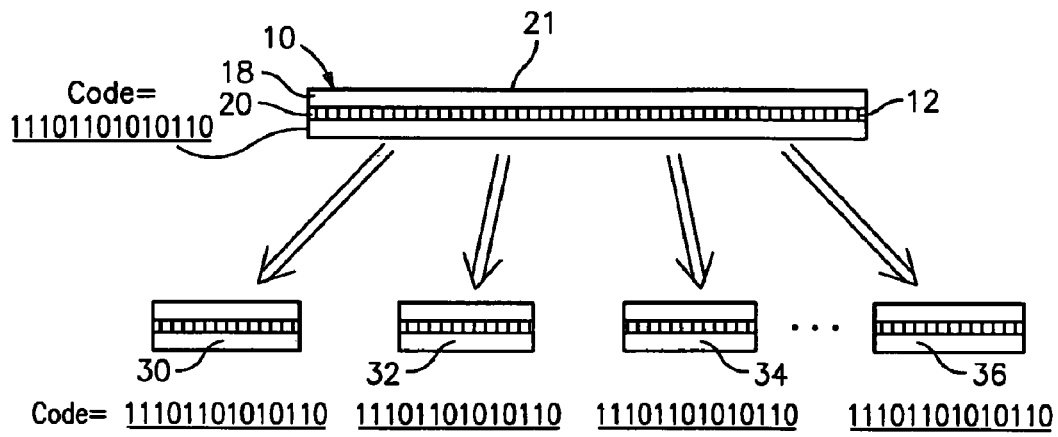
*FIG. 44*

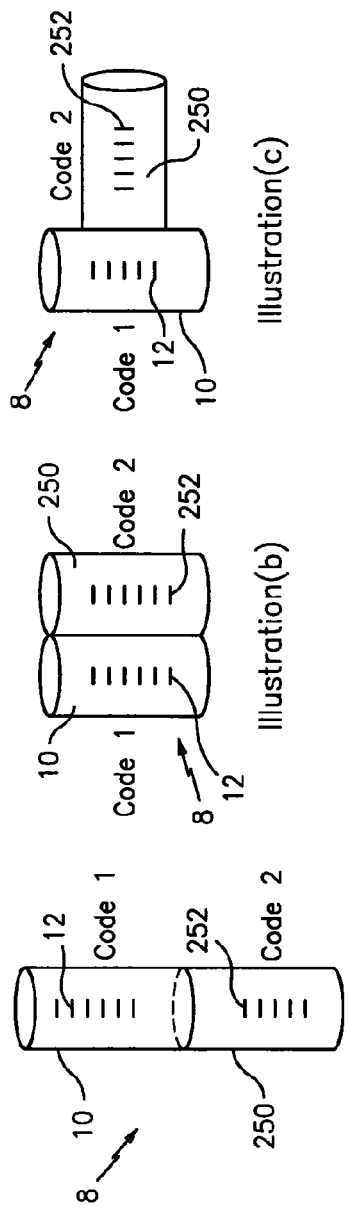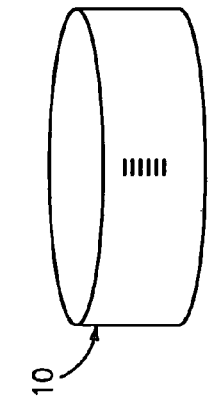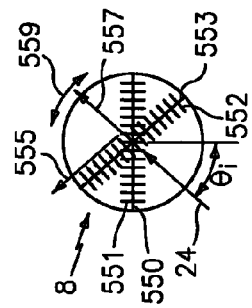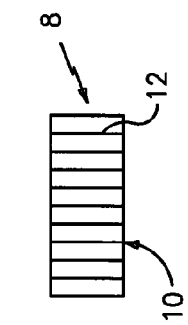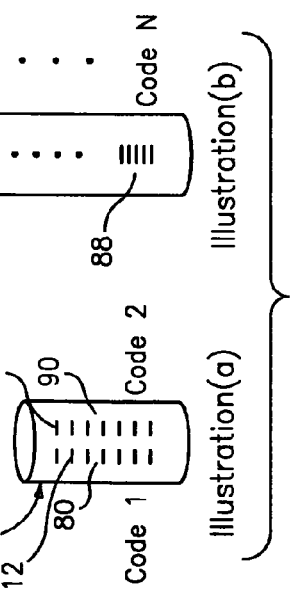

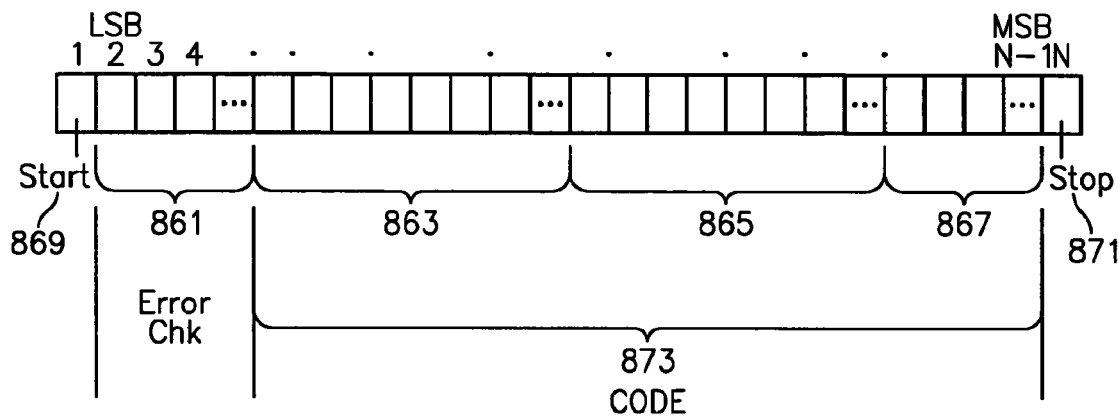
*FIG. 55*
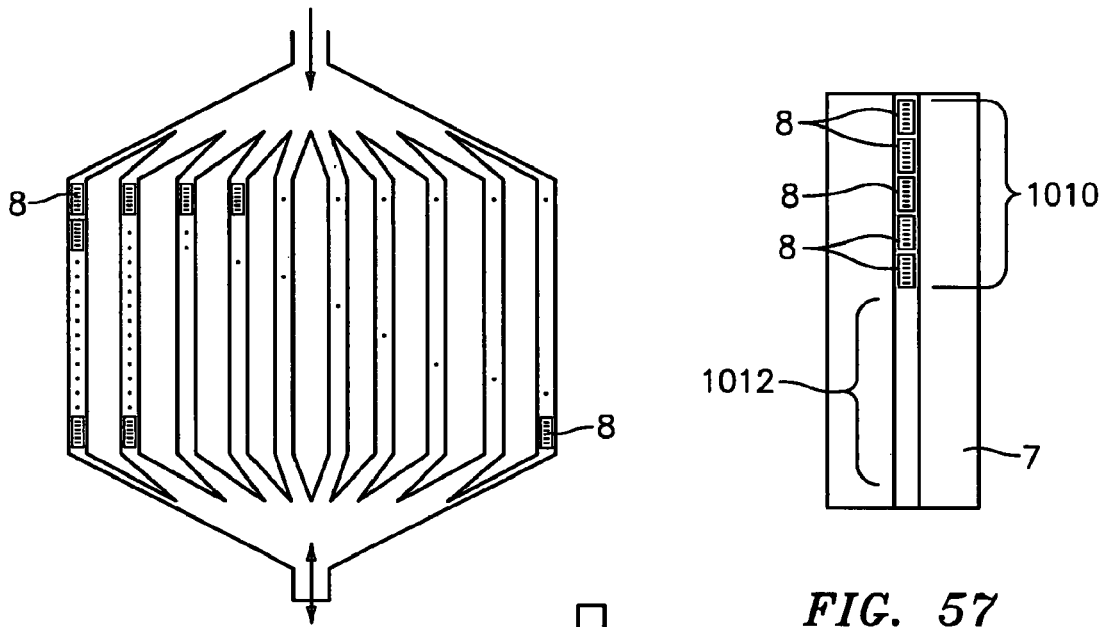
*FIG. 56*
*FIG. 57*
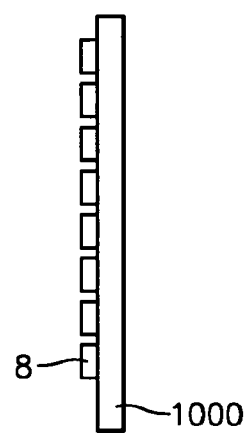
*FIG. 58*

DIFFRACTION GRATING-BASED ENCODED MICROPARTICLE ASSAY STICK

CROSS REFERENCES TO RELATED APPLICATIONS

The present application claims the benefit of: U.S. Provisional Application Ser. No. 60/610,059, filed Sep. 13, 2004, entitled "Assay Stick"; and Ser. No. 60/654,716, filed Feb. 17, 2005, entitled "Diffraction Grating Based Encoded Microparticle Assay Stick". The present application is a continuation-in-part of U.S. patent application Ser. No. 10/661,234 (the '234 application), filed Sep. 12, 2003, now U.S. Pat. No. 7,106,513 entitled "Diffraction Grating-Based Optical Identification Element", which claims the benefit of U.S. Provisional Application No. 60/410,541 (the '541 application), filed Sep. 12, 2002, and is a continuation-in-part of U.S. application Ser. No. 10/645,689 (the '689 application), filed Aug. 20, 2003 now abandoned. The '689 application claims the benefit of the '541 application and U.S. Provisional Application No. 60/405,087 (the '087 application), filed Aug. 20, 2002. The present application is also a continuation-in-part of U.S. patent application Ser. No. 10/661,031 (the '031 application), filed Sep. 12, 2003, now U.S. Pat. No. 7,349,158 entitled "Diffraction Grating-Based Encoded Micro-particles for Multiplexed Experiments". The '031 application claims the benefit of the '541 application and is a continuation-in-part of U.S. application Ser. No. 10/645,686 (the '686 application), filed Aug. 20, 2003 now abandoned. The '686 application claims the benefit of the '541 application and the '087 application. The present application is also a continuation-in-part of U.S. patent application Ser. No. 10/661,082 (the '082 application), filed Sep. 12, 2003, now U.S. Pat. No. 7,126,755 entitled "Method and Apparatus for Labeling Using Diffraction Grating based Encoded Optical Identification Elements". The '082 application claims the benefit of the '541 application and is a continuation-in-part of the '686 application and also the '689 application. The present application is also a continuation-in-part of U.S. patent application Ser. No. 10/661,115, filed Sep. 12, 2003 now abandoned, entitled "Assay Stick", which claims the benefit of the '541 application and is a continuation-in-part of the '686 application and the '689 application. U.S. Application Nos. 60/610,059; 60/654,716; Ser. Nos. 10/661,234; 10/661,031; 10/661,082; and 10/661,115 are incorporated herein by reference in their entirety.

The following cases contain subject matter related to that disclosed herein and are all incorporated herein by reference in their entirety: U.S. patent application Ser. No. 10/661,836, filed Sep. 12, 2003, entitled "Method And Apparatus For Aligning Microbeads In Order To Interrogate The Same"; Ser. No. 11/063,665, filed Feb. 22, 2005, entitled "Multi-well Plate with Alignment Grooves for Encoded Microparticles"; Ser. No. 10/661,254 filed Sep. 12, 2003, entitled "Chemical Synthesis Using Diffraction Grating-Based Encoded Optical Elements"; U.S. patent application Ser. No. 10/661,116, filed Sep. 12, 2003, entitled "Method Of Manufacturing Of A Diffraction Grating-Based Identification Element"; and U.S. patent application Ser. No. 10/763,995, filed Jan. 22, 2004, entitled, "Hybrid Random Bead/Chip Based Microarray"; and U.S. patent application, Ser. No. 10/956,791, filed Oct. 1, 2004, entitled "Optical Reader for Diffraction Grating-Based Encoded Optical Identification Elements".

TECHNICAL FIELD

This invention relates to assays, and more particularly to multiplexed chemical assays that use beads or micro-particles.

BACKGROUND ART

A common class of experiments, known as a multiplexed assay or multiplexed experiment, comprises mixing (or reacting) a labeled target analyte or sample (which may have known or unknown properties or sequences) with a set of "probe" or reference substances (which also may have known or unknown properties or sequences). Multiplexing allows many properties of the target analyte to be probed or evaluated simultaneously (i.e., in parallel). For example, in a gene expression assay, the "target" analyte, usually an unknown sequence of DNA, is labeled with a fluorescent molecule to form the labeled analyte.

In a known DNA/genomic sequencing assay, each probe consists of known DNA sequences of a predetermined length, which are attached to a labeled (or encoded) bead or to a known location on a substrate.

When the labeled target analyte is mixed with the probes, segments of the DNA sequence of the labeled target analyte will selectively bind to complementary segments of the DNA sequence of the known probe. The known probes are then spatially separated and examined for fluorescence. The beads that fluoresce indicate that the DNA sequence strands of the target analyte have attached or hybridized to the complementary DNA on that bead. The DNA sequences in the target analyte can then be determined by knowing the complementary DNA (or cDNA) sequence of each known probe to which the labeled target is attached. In addition the level of fluorescence is indicative of how many of the target molecules hybridized to the probe molecules for a given bead.

Generally, the probes are either spatially separated or otherwise labeled to identify the probe, and ultimately the "target" analyte, using one of two approaches. The first approach separates the probes in a predetermined grid, where the probe's identity is linked to its position on the grid. One example of this is a "chip" format, where DNA is attached to a 2-D substrate or microarray, where oligomer DNA sequences are selectively attached (either by spotting or grown) onto small sections or spots on the surface of the substrate in a predetermined spatial order and location on a substrate (usually a planar substrate, such as a glass microscope slide).

A second or "bead based" approach, for identifying the probe allows the probes to mix without any specific spatial position, which is often called the "random bead assay" approach. In this approach the probes are attached to a bead instead of a larger substrate so they are free to move (usually in a liquid medium). This approach has an advantage in that the analyte reaction can be performed in a liquid/solution by conventional wet-chemistry techniques, which gives the probes a better opportunity to interact with the analyte. However, this approach requires that each bead or probe be individually identifiable.

Additional Background on Multiplexing Platforms

In addition, it is also noted that multiplexed biomarker assays are commonly performed in microarray formats. The instrumentation, processing, and readout of microarrays for protein expression are complex. Microarrays are easily subject to contamination, and require extreme care and highly skilled technicians for successful operation. Furthermore, most microarrays are based on a microscope slide format that is not conducive to automation during the sample hybridization and wash steps. Finally, protein microarrays are notoriously difficult to manufacture by mechanical spotting and printing methods. There is a critical need to develop simpler device approaches that both reduce the cost of readout equipment and consumables, and are amenable to automation commonly available in centralized diagnostic labs.

One of the keys to the commercial success of any multiplexed protein measurement technology is manufacturability. Bead-based assays were developed, in part, to circumvent the fundamentally undesirable process of spotting antibodies onto a planar microarray surface. In the case of multiplex microparticle assays, probes are attached to microparticle surfaces in large batches using wet chemistry techniques, thus producing high test-to-test uniformity. The fundamental technology problem that needs to be addressed in bead-based assays is identifying the particle type once the particle batches are mixed for multiplexed readout.

There are many known methods and substrate types that can be used for tagging or otherwise uniquely identifying individual beads with attached probes. Known methods include using polystyrene latex spheres that are colored or fluorescent labeled. Other methods include using small plastic cans with a conventional bar code applied, or a small container includes a solid support material and a radio-frequency tag. In particular, there have been a large number of particle encoding technologies proposed in the literature [1A-4A], but few show commercial promise, particularly for diagnostic applications. Encoding technologies based on quantum dots [1A], fluorescent glass particles [2A], a variety of spatial bar-coding approaches [3A], and radio-frequency tagging [4A] have been attempted. To date, none of these techniques have become commercially successful due to limitations in readout speed, cost, and manufacturability. See [1A] Hongxia Xu, Michael Y. Sha, Edith Y. Wong, Janet Uphoff, Yanzhang Xu, Joseph A. Treadway, Anh Truong, Eamonn O'Brien, Steven Asquith, Michael Stubbins, Nigel K. Spurr, Eric H. Lai and Walt Mahoney (2003) Multiplexed SNP genotyping using the Qbead™ system: a quantum dot-encoded microsphere-based assay, Nucleic Acids Res. 31(8):e43; [2A] Dejneka, Matthew J., Alexander Streltsov, Santona Pal, Anthony G. Frutos, Christy L. Powell, Kevin Yost, Po Ki Yuen, Uwe Müller, and Joydeep Lahiri, Rare earth-doped glass microbarcodes (2003) Proc. NAS 100: 389-393; [3A] Finkel, Nancy H., Xinhui Lou, Cuiying Wang, and Lin He, Barcoding the Microworld, Anal. Chem. (2004) 76, 352A-359A; and [4A] Miller, K., Downsizing DNA Assays (2002) The Scientist, 16(1) 52, which are all hereby incorporated by reference in their entirety. See also the following reference is also incorporated by references in its entirety: including [5A] Gunderson K L, Kruglyak S, Graige M S, Garcia F, Kermani B G, Zhao C, Che D, Dickinson T, Wickham E, Bierle J, Doucet D, Milewski M, Yang R, Siegmund C, Haas J, Zhou L, Oliphant A, Fan J B, Barnard S, Chee M S, Decoding randomly ordered DNA arrays. Genome Res. 2004 May; 14(5): 870-7.

A common issue in performing multiplexed assays is to conserve the amount of volume of the target analyte (or sample) thereby minimizing the amount of preparation or reagents used in preparation of the analyte (e.g., enzymes to create PCR amplification, labeled nucleotides, etc.) required to perform the assay. This is due to the high cost of reagents and/or limited available quantity of the sample (e.g., animal cells). In addition, assays performed in a laboratory environment are often not well suited for use in a clinical or point-of-care application environment. It is also desirable to minimize the amount of preparation steps/reagents used to prepare the analyte, to reduce the possible errors introduced by sample preparation steps.

Accordingly, it would be desirable to have an assay platform that conserves the amount of target analyte (or reagent) used and/or is convenient for use in a clinical or point-of-care application environment.

Rather, arraying the beads onto a surface and pre-identifying them during manufacturing is an attractive alternative because it eliminates the need for the instrument to identify particles based on anything other than spatial location. Pre-arraying particles overcomes the printing cost and problems inherent to antibody microarrays and avoids some of the problems with flow cytometry.

For such a randomly assembled bead array system to be practical for protein biomarker measurements should be characterized by (1) An economical encoding mechanism that does not interfere with fluorescence readout or surface chemistry and (2) an integrated and disposable microfluidic hybridization chamber for introduction of samples and reagents. This type of system should have the benefits of:

Random self assembly and rapid, robust decoding for inexpensive, reliable manufacturing Small sample volumes and high sensitivity through the use of microfluidics Simple sample handling, washing, and that can be easily automated Inexpensive optical readout instrumentation

SUMMARY OF THE INVENTION

Objects of the present invention include provision of an assay platform that conserves the amount of target analyte (or reagent) used and/or is convenient for use in a clinical or point of care environment.

According to the present invention, an assay stick, comprised: a reaction vessel; a plurality of microbeads disposed within said reaction vessel; each of said microbeads having at least one diffraction grating disposed therein, said grating having at least one refractive index pitch superimposed at a common location; said grating providing an output optical signal when illuminated by an incident light signal; and said optical output signal being indicative of a code in said substrate.

The present invention provides a stick assay platform that minimizes the amount of target analyte (or reagent) that is needed to run the assay by stacking microbeads in a glass column reaction vessel such that minimal volume is used to wet the beads. The beads may be chemically coated or functionalized with the probe material before or after being placed in the assay stick.

Alternatively, the invention may be inside or made part of a syringe or pipette tip or other lab or clinical instrument that flows fluids and/or obtains fluid samples. The assay stick may be disposed of after the experiment/assay is completed or reused to run the same assay with the same stick to further validate or confirm the assay results. Alternatively, the stick may be sterilized and reused for another assay if desired. The sticks do not require the user to handle, count, separate, align or sort individual tiny microbeads, e.g., less than about 150 microns in diameter (other bead sizes may be used). The sticks are easy to handle and use to perform an assay and read the results. As a result, the invention may be used in a clinical or point-of-care setting as well as in a research environment.

Also, the assay stick of the present invention allows for traceability of each bead in the assay stick. Accordingly, each bead can have a batch code, lot number, date code, functionalization date, location, vendor code, and/or any other information desired or required for traceability, identification, and/or authenticity. In addition this information may be encrypted for covert applications to avoid counterfeiting of assay sticks.

The invention may be used in any assay or multiplexed experiment. The assay stick 7 may be reused or disposed upon completion of the assay. The present invention may be used with any known combinatorial chemistry or biochemistry assay process, and are especially adaptable to assays having solid phase immobilization. The invention may be used in many areas such as drug discovery, functionalized substrates, biology, proteomics, combinatorial chemistry, agrichemistry, biothreat, and any assays or multiplexed experiments. Examples of common assays are SNP (single nucleotide polymorphism) detection, DNA/genomic sequence analysis, genotyping, gene expression assays, proteomics assay, peptide assays, antigen/antibody assays (immunoassay), ligand/receptor assays, DNA analysis/tracking/sorting/tagging, as well as tagging of molecules, biological particles, cell identification and sorting, matrix support materials, receptor binding assays, scintillation proximity assays, radioactive or nonradioactive proximity assays, and other assays, high throughput drug/genome screening, and/or massively parallel assay applications. The analyte can be labeled, detected or identified with any technique capable of being used in an assay with arrays or beads, including but not limited to fluorescent, luminescent, phosphorescent, quantum dot, light scattering colloidal particles, radioactive isotopes, mass spectroscopy, NMR (nuclear magnetic resonance), EPR (electro paramagnetic resonance), ESR (electron spin resonance), IR (infrared), FTIR (Fourier transform infra red), Raman spectroscopy, or other magenetic, vibrational, electromagnetic, or optical labeling or detection techniques. The invention provides uniquely identifiable beads with reaction supports by active coatings for reaction tracking to perform multiplexed experiments. The invention may also be used in any chemical and/or biochemical purification, isolation, or filtering-type process where bead or bead-like solid supports may be used (e.g., chromatographic techniques, such as affinity column purification). In that case, the above techniques for labeling, detection or identification may be used.

Further, the invention may be used as a library storage medium. The beads in the stick may have predetermined code, or may have random codes. Also, the stick may be used to test a class of compounds, e.g., typical antibodies/antibiotics. Also the beads in the stick may be partially or totally identical for redundancy purposes or for other purposes.

The invention may be used to maximize bead surface area to sample volume ratio by providing a reaction vessel that has a very small free volume. Because the sample volume required for an assay is potentially very small, the need to perform sample amplification or buffering may be eliminated or significantly reduced. For example, in a DNA assay, the reduced sample volume required to perform an assay using the assay stick of the present invention may be sufficient to avoid having to perform a known PCR (polymerized chain reaction) step or other amplification or buffering step commonly performed in assays that require more sample or reagent volume.

In addition the stick format allows one to read the same bead multiple times at multiple orientations thus increasing the single noise ratio. In addition, one or multiple sticks may be used at one time in a "macrostick", or a plurality of assay sticks. Further, the invention facilitates ease of further processing needed for hybridization or other experimentation, e.g., heating, cooling, reading, mixing, agitation, etc. If heating is required the stick will easily allow for this. Also, the beads may not be coded but may be put in a predetermined order or mapped. Also, instead of beads, the inside of the tube or capillary diameter may be spotted or grown with cells or molecules if desired. Also, instead of a capillary tube, the beads may be attached to a strip or support and used as a test strip.

The cylindrical geometry of the microbeads and inner diameter of the tube provides efficient use the available sample material to extract information, usually in the form of a fluorescence measurement.

In many instances, the sample used in an assay is in the form of PCR products and consequently the volume of the material is quite limited, e.g., on the order of 5 to 200 micro liters or less. Increasing the volume of the sample by addition of buffer only serves to dilute the sample, which reduces the fluorescent signal. To achieve the largest signal, one needs to attach as much material to the substrate as possible. The problem is stated best as follows: for a given concentration one needs to cover (and interrogate) the largest possible area with least volume of sample material. A convenient figure of merit, which should be maximized, is the ratio, R=Bead Area/Sample Volume. The most ideal geometrical configuration for achieving this with more than one bead is cylinders placed in a tube. With the present invention, one can coat beads with only as much material as required to make a mono-layer on the surface of the bead.

The present invention shows improved sensitivity for several reasons:

(1) The turbulent flow over arrayed particles breaks surface boundary layers and enhances reaction kinetics;

(2) Because only small volumes are needed to cover the surface of the beads, analyte concentrations can be kept high without dilution; and (3) Only a few particles of each type need be present, minimizing capture surface which concentrates the signals into a smaller area.

The foregoing and other objects, features and advantages of the present invention will become more apparent in light of the following detailed description of exemplary embodiments thereof.

BRIEF DESCRIPTION OF THE DRAWINGS

FIGS. 2-24 show alternative embodiments or applications of an assay stick, in accordance with the present invention.

FIG. 36 is a perspective view showing azimuthal multiplexing of a thin grating for an optical identification element, in accordance with the present invention.

FIG. 37 is side view of a blazed grating for an optical identification element, in accordance with the present invention.

FIGS. 40-41 are side views of an optical identification element where light is incident on an end face, in accordance with the present invention.

FIG. 42, illustrations (a)-(c) are side views of an optical identification element having a blazed grating, in accordance with the present invention.

FIG. 43 is a side view of an optical identification element having a coating, in accordance with the present invention.

FIG. 44 is a side view of whole and partitioned optical identification element, in accordance with the present invention.

FIG. 45 is a side view of an optical identification element having a grating across an entire dimension, in accordance with the present invention.

FIG. 46, illustrations (a)-(c), are perspective views of alternative embodiments for an optical identification element, in accordance with the present invention.

FIG. 47, illustrations (a)-(b), are perspective views of an optical identification element having multiple grating locations, in accordance with the present invention.

FIG. 48, is a perspective view of an alternative embodiment for an optical identification element, in accordance with the present invention.

FIG. 49 is a view an optical identification element having a plurality of gratings located rotationally around the optical identification element, in accordance with the present invention.

FIG. 53 is a side view an optical identification element having a reflective coating thereon, in accordance with the present invention.

FIG. 54 illustrations (a)-(b) are side views of an optical identification element polarized along an electric or magnetic field, in accordance with the present invention.

FIG. 55 shows a bit format for a code in an optical identification element, in accordance with the present invention.

FIG. 56 shows a diagram of a plurality of parallel microfluidic channels, in accordance with the present invention.

FIG. 57 shows a diagram of a plurality beads that do not completely fill a reaction chamber, in accordance with the present invention.

FIG. 58 shows a diagram of a plurality of beads attached to a planar surface as a test strip, in accordance with the present invention.

BEST MODE FOR CARRYING OUT THE INVENTION

Figure 1:
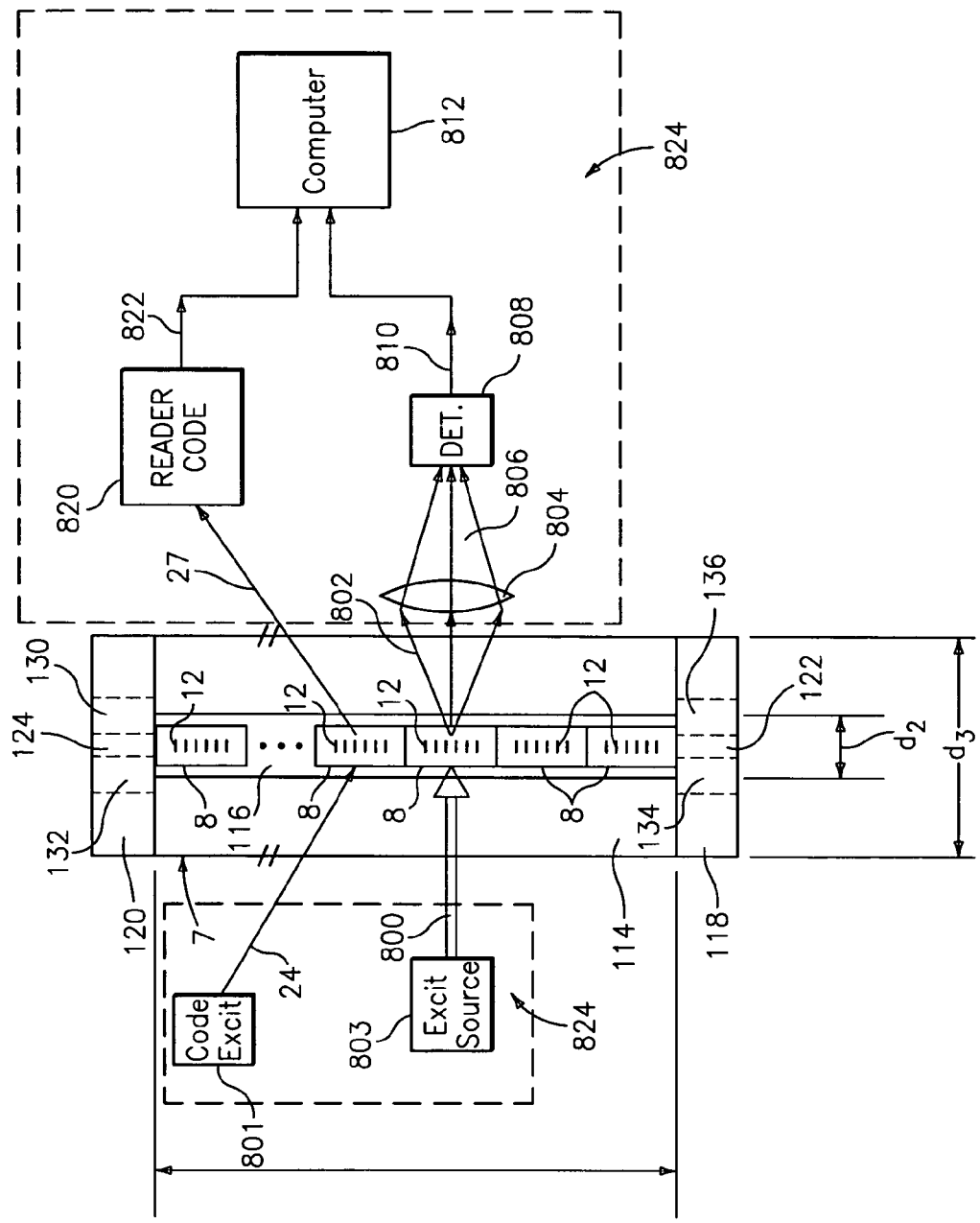
FIG. 1 is a side view of an assay stick, and a code reader, in accordance with the present invention.

Referring to FIG. 1, a diffraction grating-based encoded microparticle (or microbead) assay stick 7 includes a transparent reaction vessel or tube 14 having at least one longitudinal hole or cavity 116 along its length and having one or more microbeads 8 disposed therein. Each of the microbeads 8 have a uniquely identifiable digital code based on a multi-pitched diffraction grating 12 disposed therein, similar to the optical identification elements described in Copending U.S. patent application, Ser. No. 10/661,234, filed 12 Sep. 2003, which is incorporated by reference herein in its entirety.

The tube 114 has an inner diameter d2, which is slightly larger, e.g., about 0.5-50 microns, than the outer diameter of the beads 8. Other diameters d2 may be used if desired, depending on the amount of solution volume desired for the assay. The cavity 116 has a length L that is substantially as long as the number of microbeads 8 in the tube 114 times the length of each bead 8. The tube 114 has an outer diameter d3 of about 5 mm, but may be any diameter that is suitable for the application or experiment being performed.

The tube 114 has end caps 118,120 with fluid access holes or port holes 122,124, disposed therein. The diameters of the port holes 122,124, are sized and positioned to prevent the beads 8 from falling out of the tube 114 and to allow the desired amount of fluid to flow along the inside of the tube 114. The port holes 122,124 may be centered under in the chamber 116 or off-center as indicated by the port holes 130,132,134,136 (discussed more hereinafter).

When the tube 114 has a cylindrical shape, the beads 8 may also have a cylindrical shape to minimize assay fluid volume requirements if desired. However, the microbeads 8 may have any desired shape and may have a different shape from the shape of the tube 114.

The codes in the microbeads 8 are detected when illuminated by incident light 24 which produces a diffracted or output light signal 27 to a reader 820, which includes the optics and electronics necessary to read the codes in each bead 8, as described in the aforementioned copending patent application, and described more hereinafter. The reader 820 provides a signal on a line 822 indicative of the code in each of the bead 8. The incident light 24 may be directed transversely from the side of the tube 114 (or from an end or any other angle) with a narrow band (single wavelength) and/or multiple wavelength source, in which case the code is represented by a spatial distribution of light and/or a wavelength spectrum, respectively, as described hereinafter and in the aforementioned copending patent application. Other illumination, readout techniques, types of gratings, geometries, materials, etc. may be used for the microbeads 8, as discussed hereinafter and in the aforementioned patent application.

For assays that use fluorescent molecule markers to label or tag chemicals, an optical excitation signal 800 is incident on the microbeads 8 through the tube 114 and a fluorescent optical output signal 802 emanates from the beads 8 that have the fluorescent molecule attached. The fluorescent optical output signal 802 passes through a lens 804, which provides focused light 802 to a known optical fluorescence detector 808. Instead of or in addition to the lens 802, other imaging optics may be used to provide the desired characteristics of the optical image/signal onto the fluorescence detector 808. The detector 808 provides an output signal on a line 810 indicative of the amount of fluorescence on a given bead 8, which can then be interpreted to determine what type of chemical is attached to the bead 10.

The tube 114 is made of glass or plastic or any material that is transparent to the code reading incident beam 24 and code reading output light beams 27 as well as the fluorescent excitation beam 800 and the output fluorescent optical signal 802, and is properly suited for the desired application or experiment, e.g., temperature range, harsh chemicals, or other application specific requirements.

The code signal 822 from the bead code reader 820 and the fluorescent signal 810 from the fluorescence detector are provided to a known computer 812. The computer reads the code associated with each bead and determines the chemical probe that was attached thereto from a predetermined table that correlates a predetermined relationship between the bead code and the attached probed. In addition, the computer 812 and reads the fluorescence associated with each bead and determines the sample or analyte that is attached to the bead from a predetermined table that correlates a predetermined relationship between the fluorescence tag and the analyte attached thereto. The computer 812 then determines information about the analyte and/or the probe as well as about the bonding of the analyte to the probe, and provides such information on a display, printout, storage medium or other interface to an operator, scientist or database for review and/or analysis. The sources 801, 803 the code reader 820, the fluorescence optics 804 and detector 808 and the computer 812 may all be part of an assay stick reader 824.

Alternatively, instead of having the code excitation source 801 and the fluorescence excitation source 803, the reader 24 may have only one source beam which provides both the reflected optical signal 27 for determining the code and the fluorescence signal 802 for reading the tagged analyte attached to the beads 8.

The microbeads 8 may be coated with the desired probe compound, chemical, or molecule prior to being placed in the tube 14. Alternatively, the beads 8 may be coated with the probe after being placed in the tube 14. As discussed hereinbefore, the probe material may be an Oligo, cDNA, polymer, or any other desired probe compound, chemical, cell, or molecule for performing an assay.

Referring to FIG. 2, to use in an experiment or assay, one end of the assay stick 7 is attached to a suction/pressure device 830 by a tube 832. The tube 832 provides suction and/or pressure to the port hole 130. The tube 830 may be attached to end of the stick 7 by an attachment device 834, such as an elastic sock or other device that holds the tube 832 in place against the stick 7. The other end of the stick 7 is inserted into a well 836 having fluid 838, e.g., the analyte and/or the probe chemicals. The suction device 830 provides sufficient suction to suck up the fluid 838 into the cavity 116 as indicated by the 840,841. The suction device 830 may also provide pressure as indicated by the lines 842,843 to the stick 7 to agitate the fluid to facilitate a reaction between the probe and the analyte or to prepare the beads with a probe chemical. One or both ends of the stick 7 may be tapered as indicated by dashed lines 844 to facilitate insertion into the well 836 and/or attachment to the suction/pressure tube 832 or for other reasons.

The beads 8 may remain in the tube 14 until the assay stick 7 is discarded or may be reused with different or other chemicals or rerun the same experiment if desired.

Referring to FIG. 3, alternatively, a syringe 850 having the fluid 838 may be attached to the stick 7. In this case, a plunger 852 is used to drive the fluid 838 into the stick 7 through a syringe tip 854, similar to the tube 832. The tip is attached to the stick 7 similar to the way the tube 832 is attached to the stick 7. In this case the syringe provides both the fluid and the suction/pressure force and the lower end 854 of the stick 7 is closed. The fluid 838 may enter and exit along the same side of the beads 8, as indicated by lines 855. Alternatively, the fluid 838 may enter along one side of the beads and exit through the other side of the beads 8, as indicated by lines 856. In that case, the tube 854 may be a bi-directional fluid flow tube. Alternatively, the end 854 may be open and the fluid 838 may be cycled through the stick 7 into a catch container 853 as indicated by a line 851.

Figure 4:
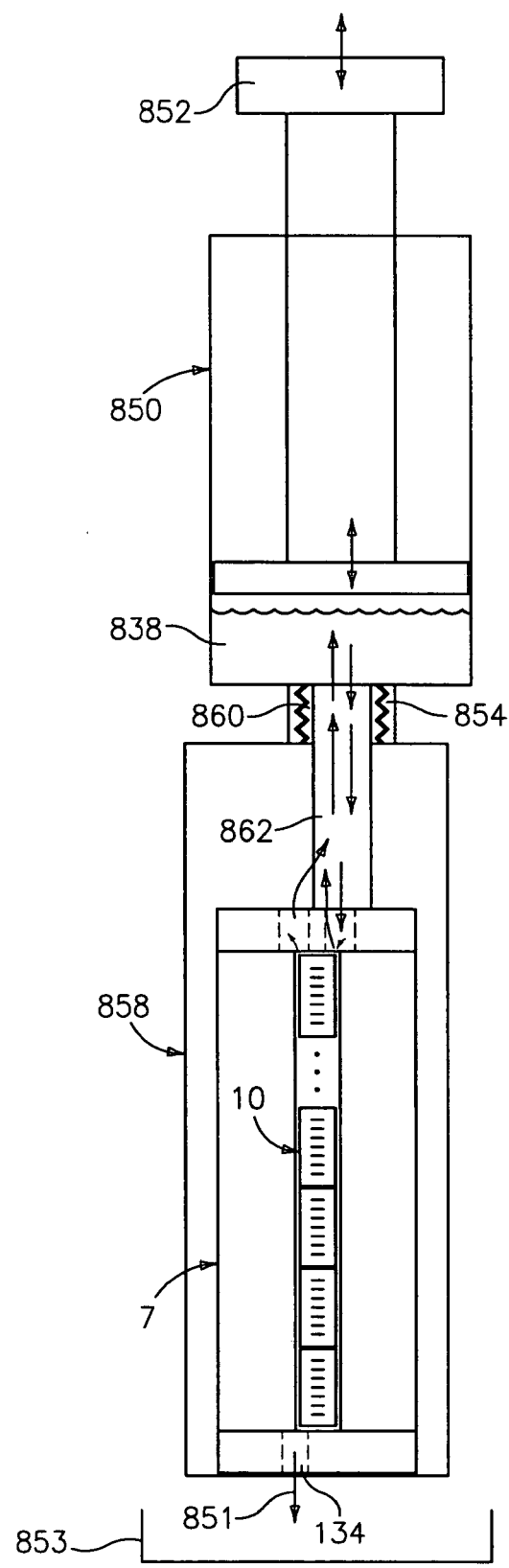

Referring to FIG. 4, the stick 7 may be contained within an assay stick housing 858 which has a threaded neck 860 that screw attaches to the tip 854 of the syringe 850 which has mating threads. The stick housing 858 has an internal tube 862 that attaches the threaded neck 860 to the assay stick 7 to provide a path for the fluid 838 to flow into the stick 7, similar to the tube 832 in FIG. 2.

Figure 5:
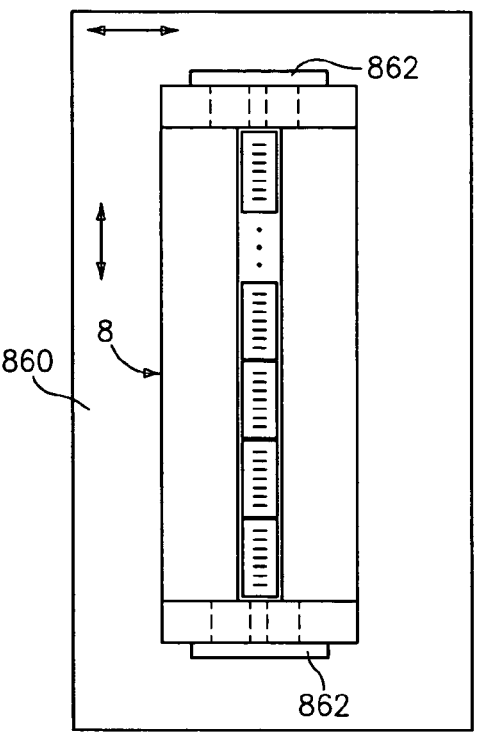
Figure 6:
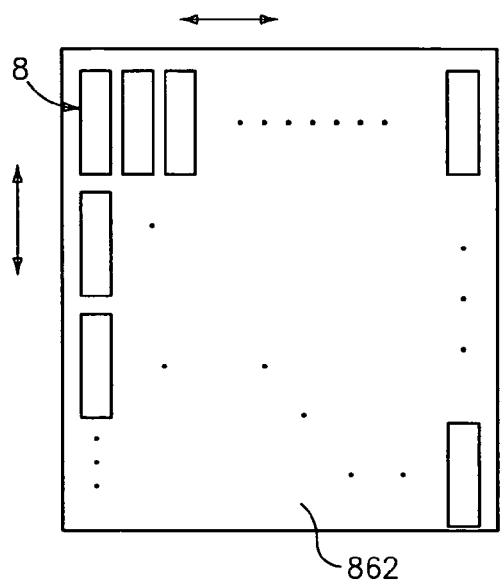
Figure 7:
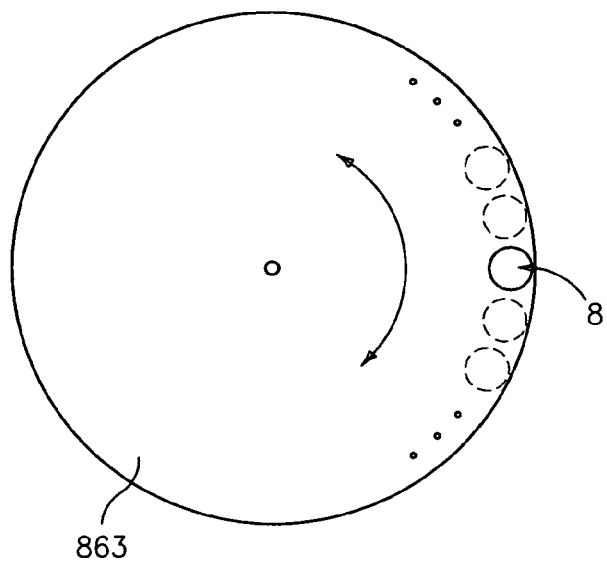

Referring to FIGS. 5,6,7, in addition to or instead of the syringe or suction/pressure device being used to agitate the chemicals to facilitate the assay reaction between the probe and the analyte, the stick 7 may be placed on a shaker device 860. In that case, plugs 862 may be used to seal off each end of the stick 7 during the shaking process. The shaker 860 may house a plurality of sticks 7 and may be an X-Y type shaker 862 (FIG. 6) or a spinning shaker 863 (FIG. 7).

Figure 8:
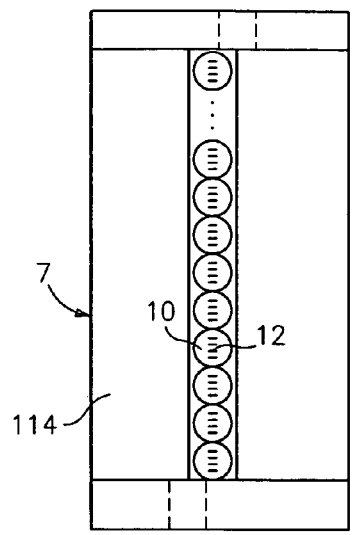
Figure 9:
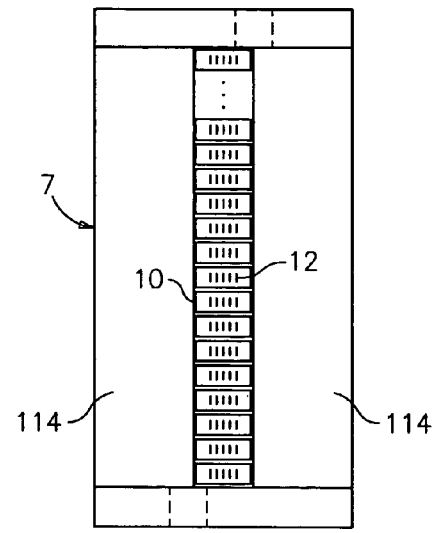

Referring to FIGS. 8 and 9, instead of stacking the beads 8 end-to-end, the beads 8 may be stacked side-to-side as shown in FIG. 9, or if the beads 8 have a circular side view with grating along the side view, they may be stacked as shown in FIG. 8.

Figure 10:
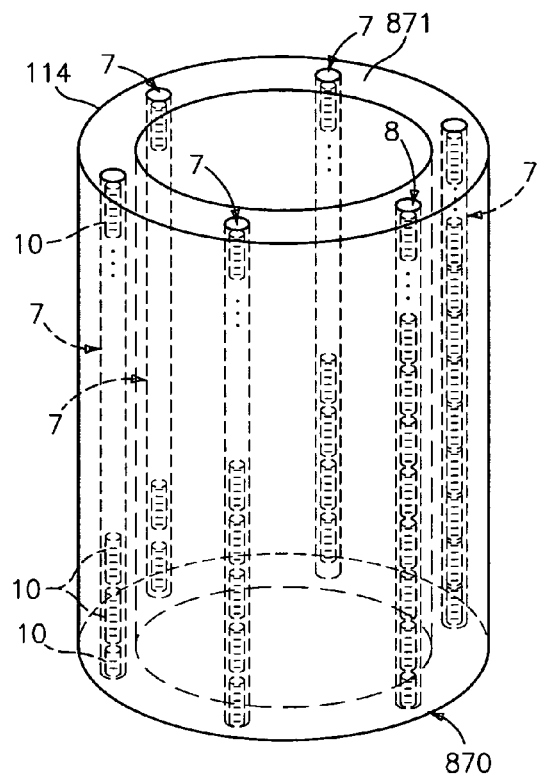
Figure 11:
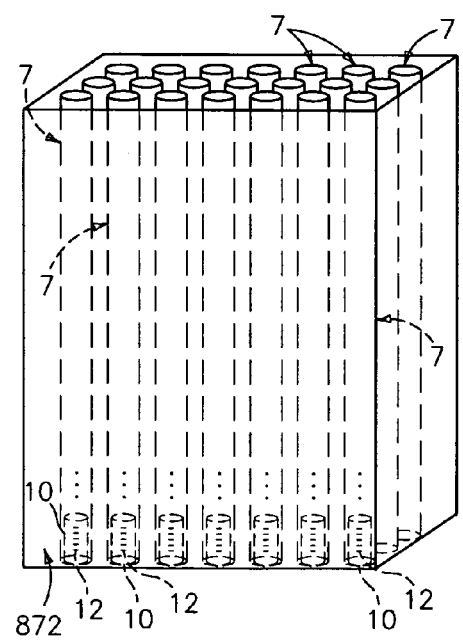

Referring to FIGS. 10 and 11, a plurality of assay sticks 7 may be placed inside a housing, or created in a cylindrical housing 870 (FIG. 10) or a rectangular or square housing 872 (FIG. 11), to create larger multi-stick or "macrostick". In that case, the assay with the macrostick may be run similar to that discussed hereinbefore, except that multiple sticks 7 can be performing an assay at one time, which can provide for a higher level of multiplexing. Also, for FIGS. 10 and 11, the holes may be drilled in a solid substrate or tubes may be placed in a housing to form the multiple sticks 870. Also, there may be a hole 871 inside the housing 870. To facilitate optical reading or for other reasons, the inner diameter of the hole 871 may be coated with a reflective coating and the beads read from the outside or the excitation or reading beams can be provided from inside the housing 870.

Figure 12:
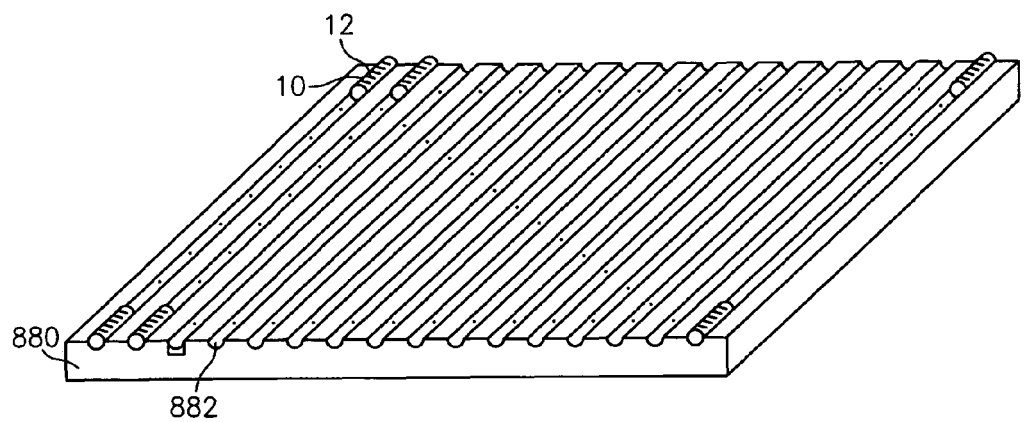
Figure 13:
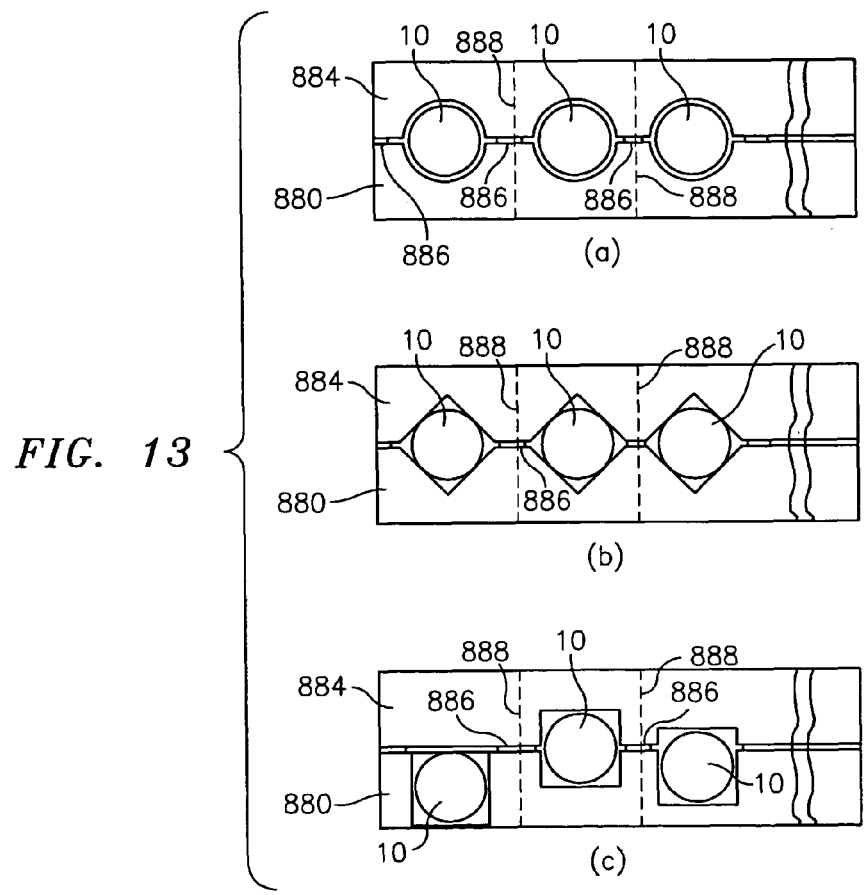

Referring to FIGS. 12 and 13, the sticks 7 may be made from a sandwich approach where the beads 10 are placed on a lower plate 880 having grooves 882 located therein or thereon. Then an upper plate 884 (FIG. 13) is placed on top of the lower plate 880. The two plates 880,884 are then glued, fused or otherwise attached in the regions 886 between the grooves 882. The shape of the grooves may be any shape that will hold the beads 10 within the chamber, e.g., rounded (FIG. 13, illustration (a), triangular (FIG. 13, illustration (b)), square (FIG. 13, illustration (c)), or other shapes. If desired, the combined plates may then be cut along lines 888 between the grooves 882 to create individual sticks 7 or groups of sticks 7, depending on the application and/or experiment. The above sandwich approach may be used for any of the embodiments of the present invention.

Accordingly, the sample material or analyte is injected into one end and spread across the beads 8 by sucking the sample material back and forth across the beads 8 or agitated by spinning or shaking. The stick 7 is then placed into the reader 824, which has the ability to read both the code and the fluorescence signal as discussed hereinbefore.

Alternatively, the sticks 7 may be made from the tubes 114 that are filled with the beads 8. In that case, to facilitate the loading of the beads into the tube 114, at least one end of the tube 114 may have a flared or funneled section 890. The section 890 may have the same diameter as the rest of the tube 114 or have a larger diameter as indicated by dashed lines 892. After the loading process the funneled section 890 may be removed along a line 893 and the end cap 120 attached to the tube 114.

Referring to FIG. 15, a funneled collar 894 may be placed on the tube 114 for loading and then may be removed after the loading process and the end cap 120 attached to the tube 114.

Referring to FIGS. 16, 17, 18, instead of the end caps 118,120 discussed hereinbefore with FIG. 1, one or both ends of the tube 114 may be heated and collapsed as indicated by dashed lines 896. The collapse may be partial as shown in FIG. 17 as shown by lines 899 or completely closed as shown by a line 898 in FIG. 18. If a partial collapse is used, the un-collapsed portion may provide a port hole in a region 897 for the injection of fluids discussed hereinbefore.

Referring to FIGS. 19, 20, instead of the end caps 118,120 discussed hereinbefore with FIG. 1, one or both ends of the tube 114 may be heated and crimped as indicated by dashed lines 900. The crimp may be partial as shown in FIG. 20 as shown by lines 902 or crimped completely circumferentially around the tube 114. If a partial crimp is used, the un-crimped portion may provide a port hole in a region 904 for the injection of fluids discussed hereinbefore.

Figure 21:
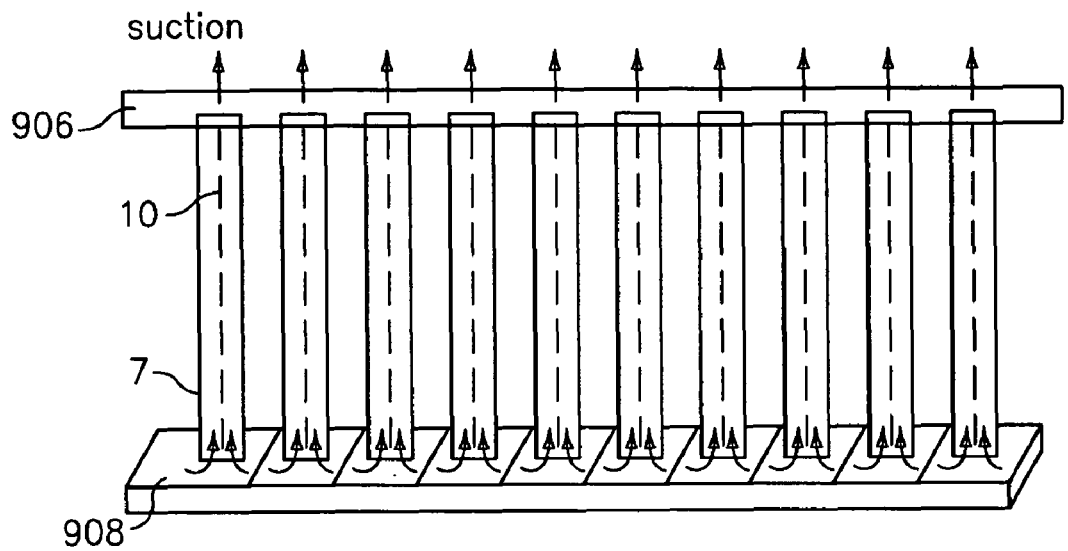

Referring to FIG. 21 a plurality of separate assay sticks 7 may be used simultaneously. In that case a suction device 906, similar to the syringe 850 or device 830 may be used for the assay. The sticks 7 may be used with a plurality of wells 908, such as a known multi-well micro-titer plate, where each stick extracts a sample from a separate well or from groups of wells.

Figure 22:
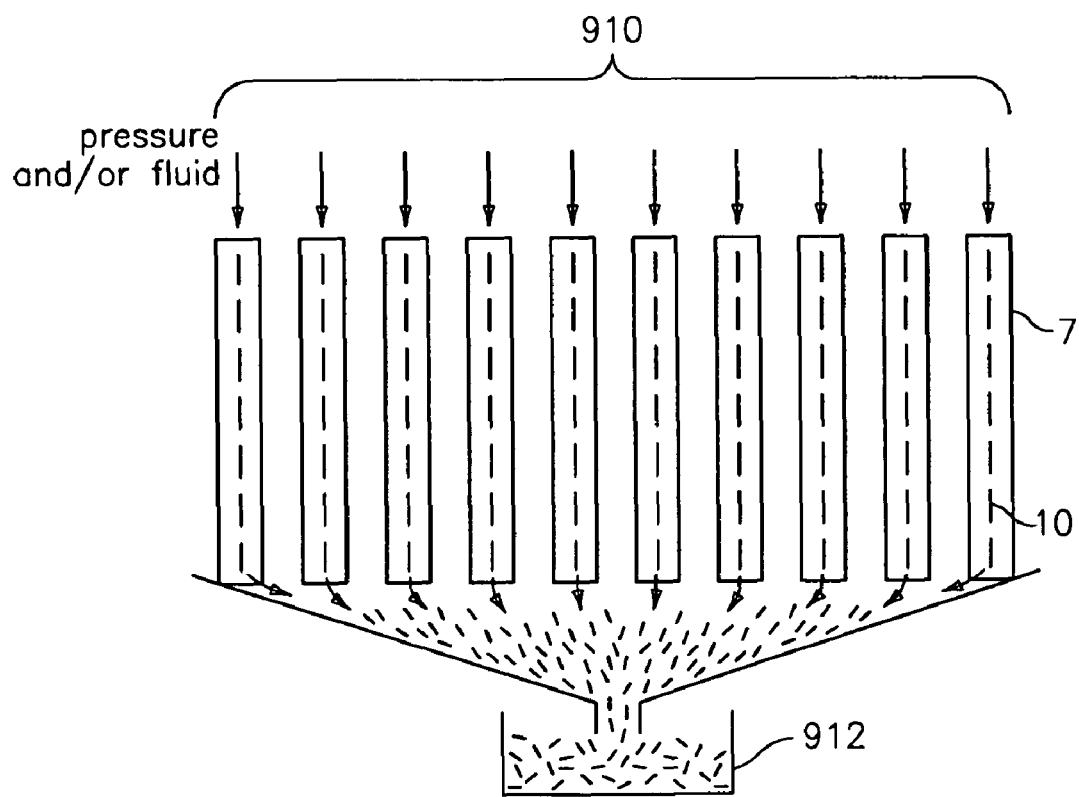

Referring to FIG. 22, instead of having the beads 8 remain in the stick 7 after being used, the beads may be removed from the sticks by applying pressure and or washing fluid as indicated by lines 910 to a container 912. An optional funnel may be used if needed to allow the beads to be collected in the container 912. In that case, the sticks 7 may be used to attach probe chemicals to beads 8 and/or perform a partial or complete assay or experiment where access to individual beads 8 is needed or desired when complete.

Figure 24:
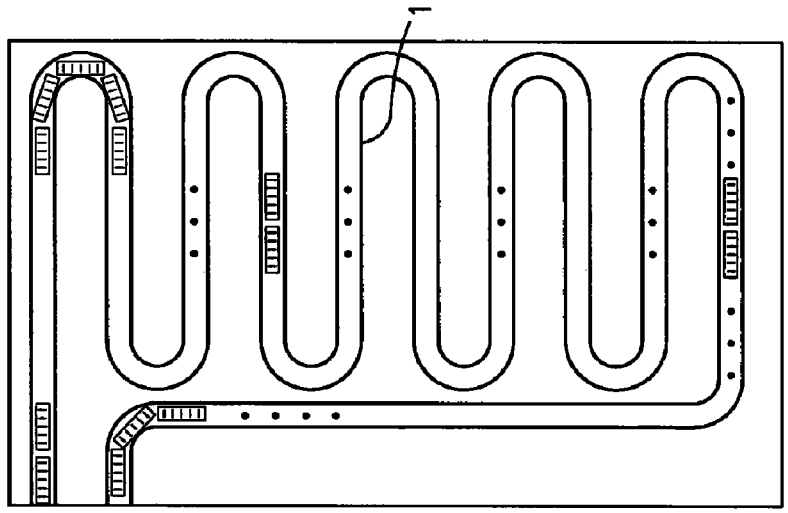
Figure 23:
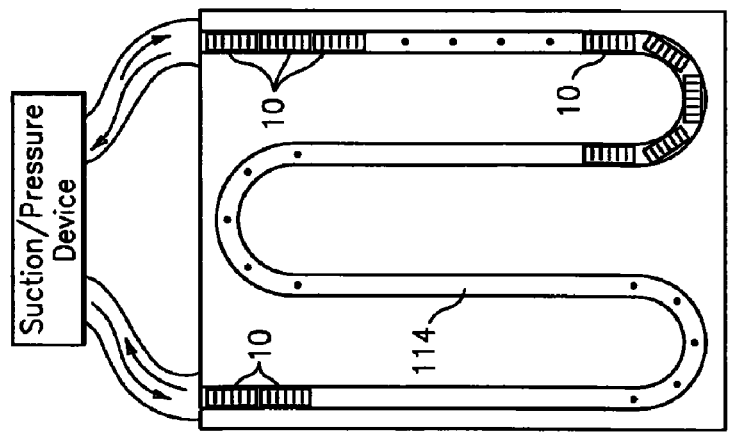

Referring to FIGS. 23 and 24, instead of the tube 114 being a straight tube, any other shape may be used, such as a serpentine or radiator hose shape or other shapes.

The present invention may be used with any known combinatorial chemistry or biochemistry assay process, and are especially adaptable to assays having solid phase immobilization. Among those having a probe immobilized on a support, include U.S. Pat. No. 6,294,327, entitled "Apparatus and Method for Detecting Samples Labeled With Material Having Strong Light Scattering Properties, Using Reflection Mode Light and Diffuse Scattering", issued Sep. 23, 2001 to Walton et al.; U.S. Pat. No. 6,242,180, entitled "Computer Aided Visualization and Analysis System for Sequence Evaluation", issued Jun. 5, 2001, to Chee; U.S. Pat. No. 6,309,823 entitled "Arrays of Nucleic Acid Probes for Analyzing Biotransformation of Genes and Methods of Using the Same", Oct. 30, 2001, to Cronin et al.; U.S. Pat. No. 6,440,667, entitled "Analysis of Target Molecules Using an Encoding System"; U.S. Pat. No. 6,355,432, entitled "Products for Detecting Nucleic Acids"; U.S. Pat. No. 6,197,506, entitled "Method of Detecting Nucleic Acids"; U.S. Pat. No. 6,309,822, entitled "Method for comparing copy number of nucleic acid sequences"; U.S. Pat. No. 5,547,839, entitled "Sequencing of surface immobilized polymers utilizing microflourescence detection", which are all incorporated herein by reference.

Generally, the assay stick of the present invention may be used to carry out any binding assay or screen involving immobilization of one of the binding agents. Such solid-phase assays or screens are well known in the chemical and biochemical arts. For example, such screening may involve specific binding of cells to a molecule (e.g. an antibody or antigen) immobilized on a microbead in the assay stick followed by analysis to detect whether or to what extent binding occurs. Alternatively, the beads may subsequently removed from the assay stick for sorting and analysis via flow cytometry (see e.g. by Needels et al. (1993). Examples of biological compounds that may be assayed or screened using the assay stick of the present invention include, e.g. agonists and antagonists for cell membrane receptors, toxins, venoms, viral epitopes, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles. In addition, the present invention may be used in any of a large number of well-known hybridization assays where nucleic acids are immobilized on a surface of a substrate, e.g. genotyping, polymorphism detection, gene expression analysis, fingerprinting, and other methods of DNA- or RNA-based sample analysis or diagnosis.

Any of the great number of isotopic and non-isotopic labeling and detection methods well-known in the chemical and biochemical assay art may be used to detect binding with the present invention. Alternatively, spectroscopic methods well-known in the art may be used to determine directly whether a molecule is bound to a surface coating in a desired configuration. Spectroscopic methods include e.g., UV-VIS, NMR, EPR, IR, Raman, mass spectrometry and other methods well-known in the art. For example, mass spectrometry also is now widely employed for the analysis of biological macromolecules. The method typically involves immobilization of a protein on a surface of substrate where it is then exposed to a ligand binding interaction. Following ligand binding (or non-binding) the molecule is desorbed from the surface and into a spectrometer using a laser (see, e.g. Merchant and Weinberger, "Recent advancements in surface-enhanced laser desorption/ionization-time of flight-mass spectrometry," Electrophoresis 21: 1164-1177 (2000)). The microbeads in the assay stick of the present invention may be used as substrates in the mass spectrometry detection methods described above.

Various aspects of the present invention may be conducted in an automated or semi-automated manner, generally with the assistance of well-known data processing methods. Computer programs and other data processing methods well known in the art may be used to store information including e.g. microbead identifiers, probe sequence information, sample information, and binding signal intensities. Data processing methods well known in the art may be used to read input data covering the desired characteristics.

As discussed hereinbefore, although a fluorescent label is probably most convenient, other sorts of labels, e.g., radioactive, enzyme linked, optically detectable, or spectroscopic labels may be used. An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemilumnescence would be preferred but is not required. Other detection systems may be adapted to the purpose, e.g., electron microscopy, scanning electron microscopy (SEM), scanning tunneling electron microscopy (STEM), infrared microscopy, atomic force microscopy (AFM), electrical conductance, and image plate transfer.

Figure 25:
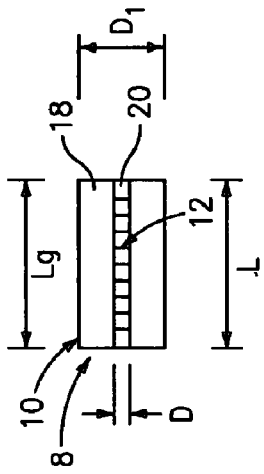
FIG. 25 is a side view of an optical identification element, in accordance with the present invention.

Referring to FIG. 25, a diffraction grating-based optical identification element 8 (or encoded element or coded element) comprises a known optical substrate 10, having an optical diffraction grating 12 disposed (or written, impressed, embedded, imprinted, etched, grown, deposited or otherwise formed) in the volume of or on a surface of a substrate 10. The grating 12 is a periodic or aperiodic variation in the effective refractive index and/or effective optical absorption of at least a portion of the substrate 10.

The optical identification element 8 described herein is the same as that described in Copending patent application Ser. No. 10/661,234, filed 12 Sep. 2003, which is incorporated herein by reference in its entirety.

In particular, the substrate 10 has an inner region 20 where the grating 12 is located. The inner region 20 may be photosensitive to allow the writing or impressing of the grating 12. The substrate 10 has an outer region 18, which does not have the grating 12 therein.

The grating 12 is a combination of one or more individual spatial periodic sinusoidal variations (or components) in the refractive index that are collocated at substantially the same location on the substrate 10 along the length of the grating region 20, each having a spatial period (or pitch) $\Lambda$. The resultant combination of these individual pitches is the grating 12, comprising spatial periods ($\Lambda 1$-$\Lambda n$) each representing a bit in the code. Thus, the grating 12 represents a unique optically readable code, made up of bits, where a bit corresponds to a unique pitch $\Lambda$ within the grating 12. Accordingly, for a digital binary (0-1) code, the code is determined by which spatial periods ($\Lambda 1$-$\Lambda n$) exist (or do not exist) in a given composite grating 12. The code or bits may also be determined by additional parameters (or additional degrees of multiplexing), and other numerical bases for the code may be used, as discussed herein and/or in the aforementioned patent application.

The grating 12 may also be referred to herein as a composite or collocated grating. Also, the grating 12 may be referred to as a "hologram", as the grating 12 transforms, translates, or filters an input optical signal to a predetermined desired optical output pattern or signal.

The substrate 10 has an outer diameter D1 and comprises silica glass ($SiO_2$) having the appropriate chemical composition to allow the grating 12 to be disposed therein or thereon. Other materials for the optical substrate 10 may be used if desired. For example, the substrate 10 may be made of any glass, e.g., silica, phosphate glass, borosilicate glass, or other glasses, or made of glass and plastic, or solely plastic. For high temperature or harsh chemical applications, the optical substrate 10 made of a glass material is desirable. If a flexible substrate is needed, plastic, rubber or polymer-based substrate may be used. The optical substrate 10 may be any material capable of having the grating 12 disposed in the grating region 20 and that allows light to pass through it to allow the code to be optically read.

The optical substrate 10 with the grating 12 has a length L and an outer diameter D1, and the inner region 20 diameter D. The length L can range from very small "microbeads" (or microelements, micro-particles, or encoded particles), about 1-1000 microns or smaller, to larger "macroelements" for larger applications (about 1.0-1000 mm or greater). In addition, the outer dimension D1 can range from small (less than 1000 microns) to large (1.0-1000 mm and greater). Other dimensions and lengths for the substrate 10 and the grating 12 may be used.

The grating 12 may have a length Lg of about the length L of the substrate 10. Alternatively, the length Lg of the grating 12 may be shorter than the total length L of the substrate 10.

The outer region 18 is made of pure silica ($SiO_2$) and has a refractive index n2 of about 1.458 (at a wavelength of about 1553 nm), and the inner grating region 20 of the substrate 10 has dopants, such as germanium and/or boron, to provide a refractive index n1 of about 1.453, which is less than that of outer region 18 by about 0.005. Other indices of refraction n1,n2 for the grating region 20 and the outer region 18, respectively, may be used, if desired, provided the grating 12 can be impressed in the desired grating region 20. For example, the grating region 20 may have an index of refraction that is larger than that of the outer region 18 or grating region 20 may have the same index of refraction as the outer region 18 if desired.

Figure 26:
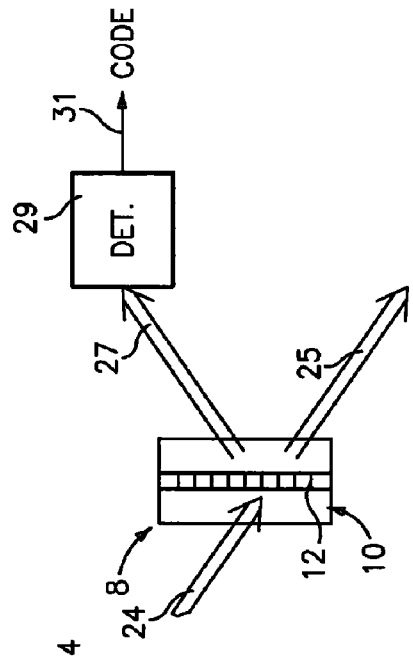
FIG. 26 is a top level optical schematic for reading a code in an optical identification element, in accordance with the present invention.

Referring to FIG. 26, an incident light 24 of a wavelength $\lambda$, e.g., 532 nm from a known frequency doubled Nd:YAG laser or 632 nm from a known Helium-Neon laser, is incident on the grating 12 in the substrate 10. Any other input wavelength $\lambda$ can be used if desired provided $\lambda$ is within the optical transmission range of the substrate (discussed more herein and/or in the aforementioned patent application). A portion of the input light 24 passes straight through the grating 12, as indicated by a line 25. The remainder of the input light 24 is reflected by the grating 12, as indicated by a line 27 and provided to a detector 29. The output light 27 may be a plurality of beams, each having the same wavelength $\lambda$ as the input wavelength $\lambda$ and each having a different output angle indicative of the pitches ($\Lambda 1$-$\Lambda n$) existing in the grating 12. Alternatively, the input light 24 may be a plurality of wavelengths and the output light 27 may have a plurality of wavelengths indicative of the pitches ($\Lambda 1$-$\Lambda n$) existing in the grating 12. Alternatively, the output light may be a combination of wavelengths and output angles. The above techniques are discussed in more detail herein and/or in the aforementioned patent application.

The detector 29 has the necessary optics, electronics, software and/or firmware to perform the functions described herein. In particular, the detector reads the optical signal 27 diffracted or reflected from the grating 12 and determines the code based on the pitches present or the optical pattern, as discussed more herein or in the aforementioned patent application. An output signal indicative of the code is provided on a line 31.

Figure 27:
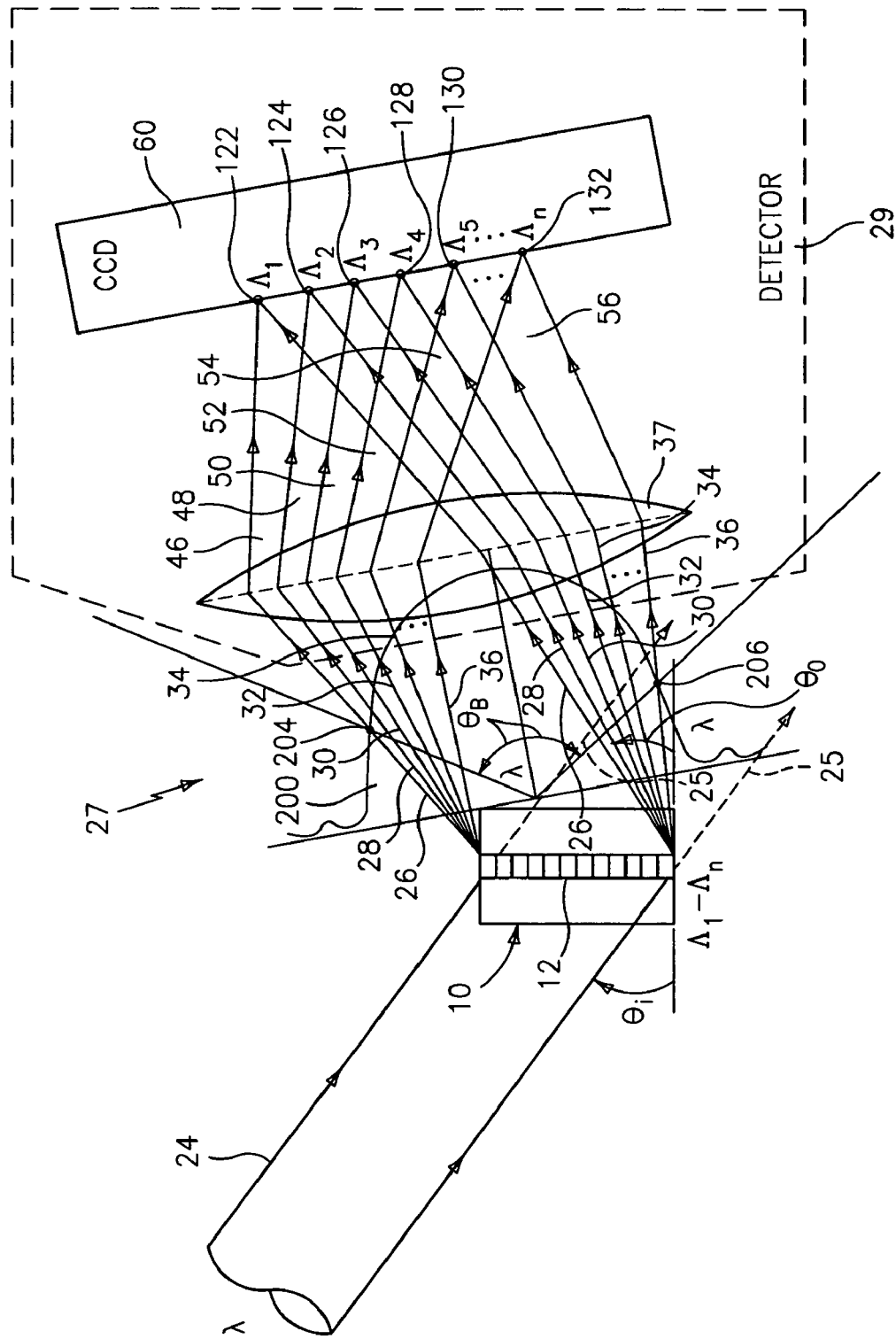
FIG. 27 is an optical schematic for reading a code in an optical identification element, in accordance with the present invention.

Referring to FIG. 27, The reflected light 27, comprises a plurality of beams 26-36 that pass through a lens 37, which provides focused light beams 46-56, respectively, which are imaged onto a CCD camera 60. The lens 37 and the camera 60, and any other necessary electronics or optics for performing the functions described herein, make up the reader 29. Instead of or in addition to the lens 37, other imaging optics may be used to provide the desired characteristics of the optical image/signal onto the camera 60 (e.g., spots, lines, circles, ovals, etc.), depending on the shape of the substrate 10 and input optical signals. Also, instead of a CCD camera other devices may be used to read/capture the output light.

Figure 28:
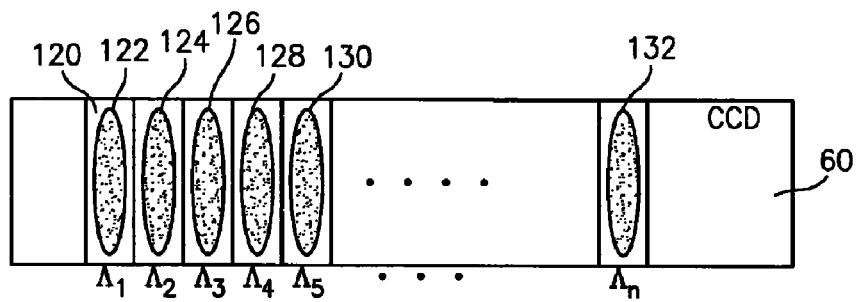
FIG. 28 is an image of a code on a CCD camera from an optical identification element, in accordance with the present invention.
Figure 29:
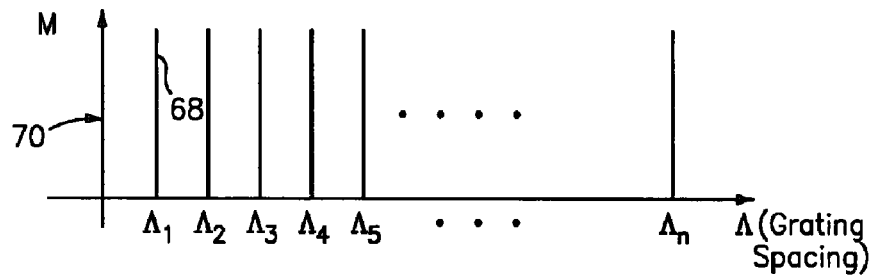
FIG. 29 is a graph showing an digital representation of bits in a code in an optical identification element, in accordance with the present invention.

Referring to FIG. 28, the image on the CCD camera 60 is a series of illuminated stripes indicating ones and zeros of a digital pattern or code of the grating 12 in the element 8. Referring to FIG. 29, lines 68 on a graph 70 are indicative of a digitized version of the image of FIG. 28 as indicated in spatial periods (Λ1-Λn).

Each of the individual spatial periods (Λ1-Λn) in the grating 12 is slightly different, thus producing an array of N unique diffraction conditions (or diffraction angles) discussed more hereinafter. When the element 8 is illuminated from the side, in the region of the grating 12, at an appropriate input angle, e.g., about 30 degrees, with a single input wavelength λ (monochromatic) source, the diffracted (or reflected) beams 26-36 are generated. Other input angles θi may be used if desired, depending on various design parameters as discussed herein and/or in the aforementioned patent application, and provided that a known diffraction equation (Eq. 1 below) is satisfied:

$$\sin(\theta_i) + \sin(\theta_o) = m\lambda/n\Lambda \qquad \text{Eq. 1}$$

where Eq. 1 is diffraction (or reflection or scatter) relationship between input wavelength λ, input incident angle θi, output incident angle θo, and the spatial period Λ of the grating 12. Further, m is the "order" of the reflection being observed, and n is the refractive index of the substrate 10. The value of m=1 or first order reflection is acceptable for illustrative purposes. Eq. 1 applies to light incident on outer surfaces of the substrate 10 which are parallel to the longitudinal axis of the grating (or the $k_B$ vector). Because the angles θi,θo are defined outside the substrate 10 and because the effective refractive index of the substrate 10 is substantially a common value, the value of n in Eq. 1 cancels out of this equation.

Thus, for a given input wavelength λ, grating spacing Λ, and incident angle of the input light θi, the angle θo of the reflected output light may be determined. Solving Eq. 1 for θo and plugging in m=1, gives:

$$\theta o = \sin^{-1}(\lambda/\Lambda - \sin(\theta i)) \qquad \text{Eq. 2}$$

For example, for an input wavelength λ=532 nm, a grating spacing Λ=0.532 microns (or 532 nm), and an input angle of incidence θi=30 degrees, the output angle of reflection will be θo=30 degrees. Alternatively, for an input wavelength λ=632 nm, a grating spacing Λ=0.532 microns (or 532 nm), and an input angle θi of 30 degrees, the output angle of reflection θo will be at 43.47 degrees, or for an input angle θi=37 degrees, the output angle of reflection will be θo=37 degrees. Any input angle that satisfies the design requirements discussed herein and/or in the aforementioned patent application may be used.

In addition, to have sufficient optical output power and signal to noise ratio, the output light 27 should fall within an acceptable portion of the Bragg envelope (or normalized reflection efficiency envelope) curve 200, as indicated by points 204,206, also defined as a Bragg envelope angle θB, as also discussed herein and/or in the aforementioned patent application. The curve 200 may be defined as:

$$I(ki, ko) \approx [KD]^2 \mathrm{sinc}^2\left[\frac{(ki-ko)D}{2}\right] \qquad \text{Eq. 3}$$

where K=2πδn/λ, where, δn is the local refractive index modulation amplitude of the grating and λ is the input wavelength, sin c(x)=sin(x)/x, and the vectors $k_i=2\pi\cos(\theta_i)/\lambda$ and $k_o=2\pi\cos(\theta_o)/\lambda$ are the projections of the incident light and the output (or reflected) light, respectively, onto the line 203 normal to the axial direction of the grating 12 (or the grating vector $k_B$), D is the thickness or depth of the grating 12 as measured along the line 203 (normal to the axial direction of the grating 12). Other substrate shapes than a cylinder may be used and will exhibit a similar peaked characteristic of the Bragg envelope. We have found that a value for δn of about $10^{-4}$ in the grating region of the substrate is acceptable; however, other values may be used if desired.

Rewriting Eq. 3 gives the reflection efficiency profile of the Bragg envelope as:

$$I(ki, ko) \approx \left[\frac{2\pi \cdot \delta n \cdot D}{\lambda}\right]^2 \left[\frac{\mathrm{Sin}(x)}{x}\right]^2 \qquad \text{Eq. 4}$$

where:

$$x = (ki-ko)D/2 = (\pi D/\lambda)*(\cos\theta i - \cos\theta o)$$

Thus, when the input angle θi is equal to the output (or reflected) angle $\theta_o$ (i.e., θi=$\theta_o$), the reflection efficiency I (Eqs. 3 & 4) is maximized, which is at the center or peak of the Bragg envelope. When θi=θo, the input light angle is referred to as the Bragg angle as is known. The efficiency decreases for other input and output angles (i.e., θi≠$\theta_o$), as defined by Eqs. 3 & 4. Thus, for maximum reflection efficiency and thus output light power, for a given grating pitch Λ and input wavelength, the angle θi of the input light 24 should be set so that the angle θo of the reflected output light equals the input angle θi.

Also, as the thickness or diameter D of the grating decreases, the width of the sin(x)/x function (and thus the width of the Bragg envelope) increases and, the coefficient to or amplitude of the sin $c^2$(or (sin(x)/x)$^2$ function (and thus the efficiency level across the Bragg envelope) also increases, and vice versa. Further, as the wavelength λ increases, the half-width of the Bragg envelope as well as the efficiency level across the Bragg envelope both decrease. Thus, there is a trade-off between the brightness of an individual bit and the number of bits available under the Bragg envelope. Ideally, δn should be made as large as possible to maximize the brightness, which allows D to be made smaller.

From Eq. 3 and 4, the half-angle of the Bragg envelope $\theta_B$ is defined as:

$$\theta_B = \frac{\eta\lambda}{\pi D \sin(\theta_i)} \qquad \text{Eq. 5}$$

where η is a reflection efficiency factor which is the value for x in the sin $c^2$(x) function where the value of sin $c^2$(x) has decreased to a predetermined value from the maximum amplitude as indicated by points 204,206 on the curve 200.

We have found that the reflection efficiency is acceptable when $\eta \leq 1.39$. This value for $\eta$ corresponds to when the amplitude of the reflected beam (i.e., from the $\sin c^2(x)$ function of Eqs. 3 & 4) has decayed to about 50% of its peak value. In particular, when $x=1.39=\eta$, $\sin c^2(x)=0.5$. However, other values for efficiency thresholds or factor in the Bragg envelope may be used if desired.

The beams 26-36 are imaged onto the CCD camera 60 to produce the pattern of light and dark regions 120-132 representing a digital (or binary) code, where light=1 and dark=0 (or vice versa). The digital code may be generated by selectively creating individual index variations (or individual gratings) with the desired spatial periods $\Lambda 1$-$\Lambda n$. Other illumination, readout techniques, types of gratings, geometries, materials, etc. may be used as discussed in the aforementioned patent application.

Figure 30:
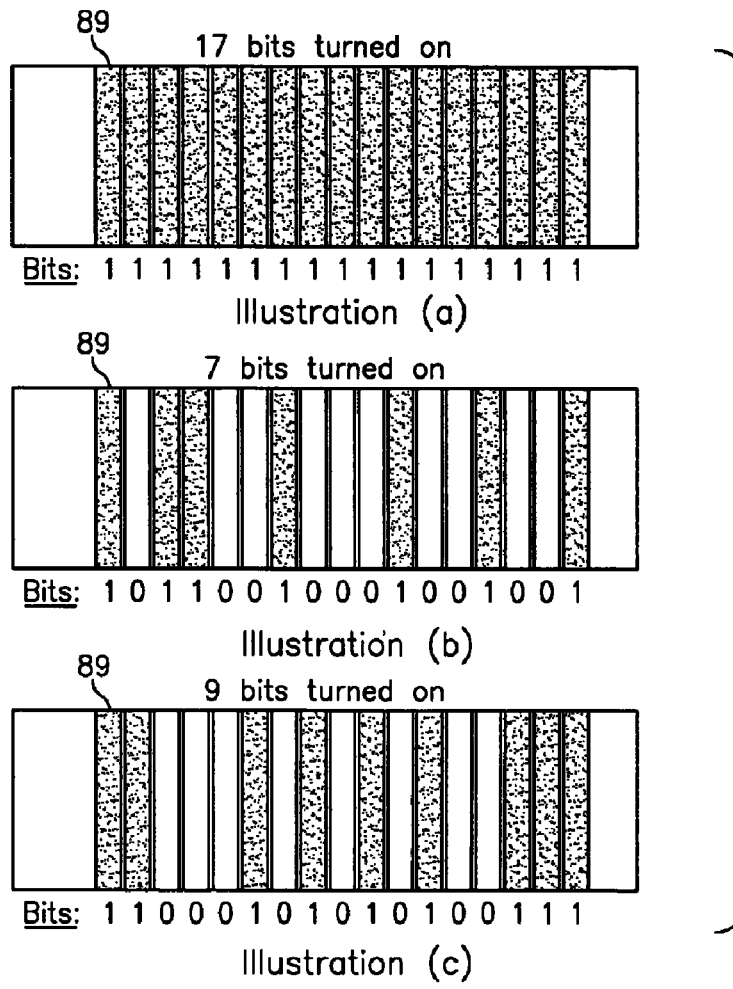
FIG. 30 illustrations (a)-(c) show images of digital codes on a CCD camera, in accordance with the present invention.

Referring to FIG. 30, illustrations (a)-(c), for the grating 12 in a cylindrical substrate 10 having a sample spectral 17 bit code (i.e., 17 different pitches $\Lambda 1$-$\Lambda 17$), the corresponding image on the CCD (Charge Coupled Device) camera 60 is shown for a digital pattern of 7 bits turned on (10110010001001001); 9 bits turned on of (11000101010100111); all 17 bits turned on of (11111111111111111).

For the images in FIG. 30, the length of the substrate 10 was 450 microns, the outer diameter D1 was 65 microns, the inner diameter D was 14 microns, δn for the grating 12 was about $10^{-4}$, n1 in portion 20 was about 1.458 (at a wavelength of about 1550 nm), n2 in portion 18 was about 1.453, the average pitch spacing $\Lambda$ for the grating 12 was about 0.542 microns, and the spacing between pitches $\Delta\Lambda$ was about 0.36% of the adjacent pitches $\Lambda$.

Figure 31:
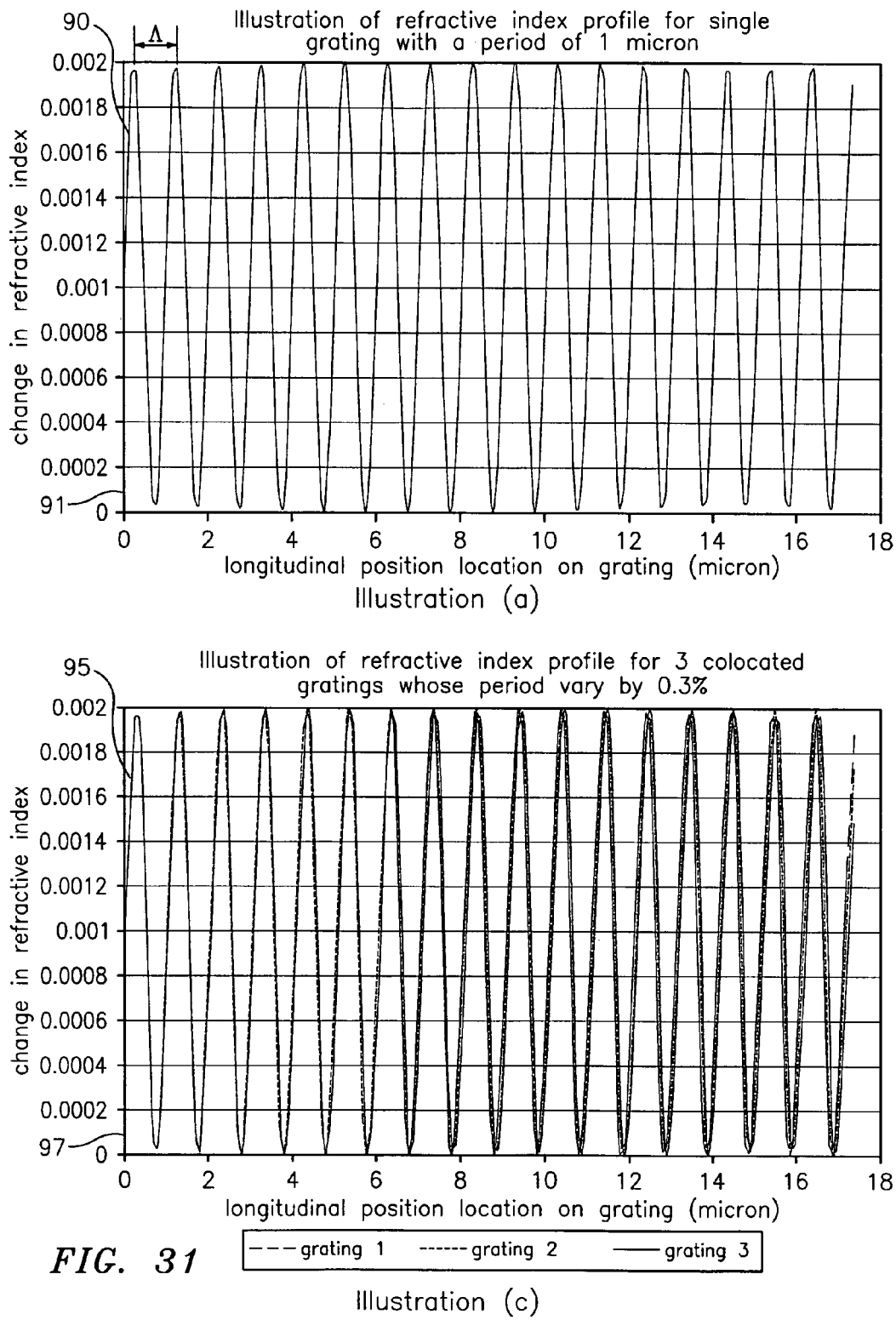
FIG. 31 illustrations (a)-(d) show graphs of different refractive index pitches and a summation graph, in accordance with the present invention.

Referring to FIG. 31, illustration (a), the pitch $\Lambda$ of an individual grating is the axial spatial period of the sinusoidal variation in the refractive index n1 in the region 20 of the substrate 10 along the axial length of the grating 12 as indicated by a curve 90 on a graph 91. Referring to FIG. 31, illustration (b), a sample composite grating 12 comprises three individual gratings that are co-located on the substrate 10, each individual grating having slightly different pitches, $\Lambda 1$, $\Lambda 2$, $\Lambda 3$, respectively, and the difference (or spacing) $\Delta\Lambda$ between each pitch $\Lambda$ being about 3.0% of the period of an adjacent pitch $\Lambda$ as indicated by a series of curves 92 on a graph 94. Referring to FIG. 31, illustration (c), three individual gratings, each having slightly different pitches, $\Lambda 1$, $\Lambda 2$, $\Lambda 3$, respectively, are shown, the difference $\Delta\Lambda$ between each pitch $\Lambda$ being about 0.3% of the pitch $\Lambda$ of the adjacent pitch as shown by a series of curves 95 on a graph 97. The individual gratings in FIG. 31, illustrations (b) and (c) are shown to all start at 0 for illustration purposes; however, it should be understood that, the separate gratings need not all start in phase with each other. Referring to FIG. 31, illustration (d), the overlapping of the individual sinusoidal refractive index variation pitches $\Lambda 1$-$\Lambda n$ in the grating region 20 of the substrate 10, produces a combined resultant refractive index variation in the composite grating 12 shown as a curve 96 on a graph 98 representing the combination of the three pitches shown in FIG. 31, illustration (b). Accordingly, the resultant refractive index variation in the grating region 20 of the substrate 10 may not be sinusoidal and is a combination of the individual pitches $\Lambda$ (or index variation).

The maximum number of resolvable bits N, which is equal to the number of different grating pitches $\Lambda$ (and hence the number of codes), that can be accurately read (or resolved) using side-illumination and side-reading of the grating 12 in the substrate 10, is determined by numerous factors, including: the beam width w incident on the substrate (and the corresponding substrate length L and grating length Lg), the thickness or diameter D of the grating 12, the wavelength $\lambda$ of incident light, the beam divergence angle $\theta_R$, and the width of the Bragg envelope $\theta_B$ (discussed more in the aforementioned patent application), and may be determined by the equation:

$$N \cong \frac{\eta \beta L}{2D\sin(\theta_i)} \qquad \text{Eq. 6}$$

Figure 32:
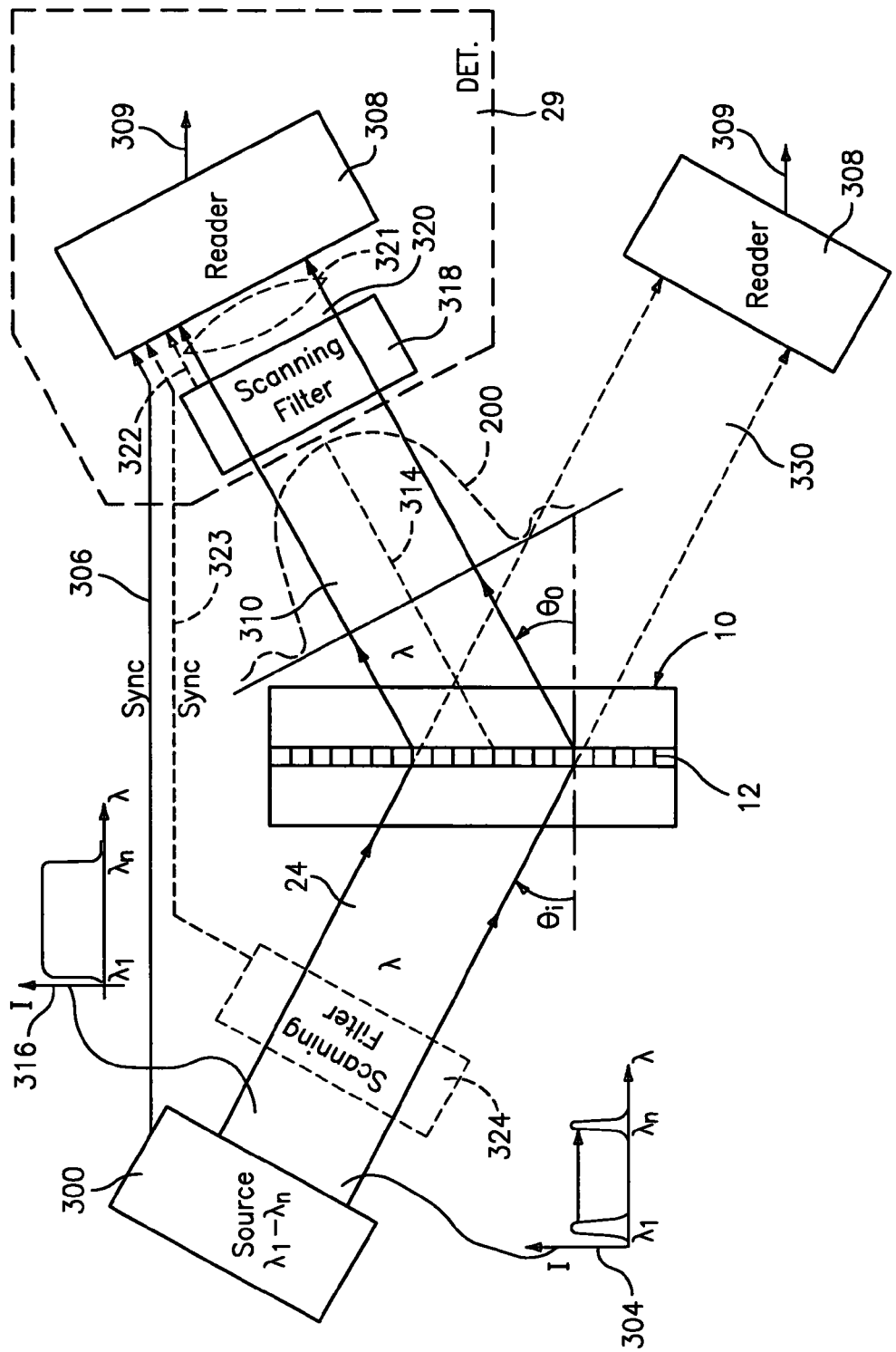
FIG. 32 is an alternative optical schematic for reading a code in an optical identification element, in accordance with the present invention.

Referring to FIG. 32, instead of having the input light 24 at a single wavelength $\lambda$ (monochromatic) and reading the bits by the angle $\theta o$ of the output light, the bits (or grating pitches $\Lambda$) may be read/detected by providing a plurality of wavelengths and reading the wavelength spectrum of the reflected output light signal. In this case, there would be one bit per wavelength, and thus, the code is contained in the wavelength information of the reflected output signal.

In this case, each bit (or $\Lambda$) is defined by whether its corresponding wavelength falls within the Bragg envelope, not by its angular position within the Bragg envelope 200. As a result, it is not limited by the number of angles that can fit in the Bragg envelope 200 for a given composite grating 12, as in the embodiment discussed hereinbefore. Thus, using multiple wavelengths, the only limitation in the number of bits N is the maximum number of grating pitches $\Lambda$ that can be superimposed and optically distinguished in wavelength space for the output beam.

Figure 33:
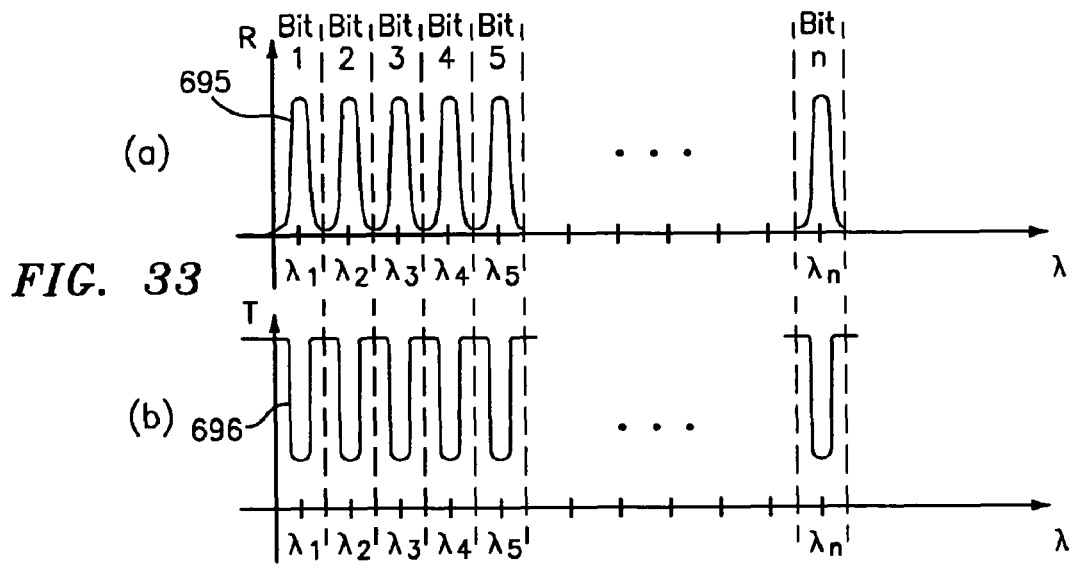
FIG. 33 illustrations (a)-(b) are graphs of reflection and transmission wavelength spectrum for an optical identification element, in accordance with the present invention.

Referring to FIGS. 32 and 33, illustration (a), the reflection wavelength spectrum ($\lambda 1$-$\lambda n$) of the reflected output beam 310 will exhibit a series of reflection peaks 695, each appearing at the same output Bragg angle $\theta o$. Each wavelength peak 695 ($\lambda 1$-$\lambda n$) corresponds to an associated spatial period ($\Lambda 1$-$\Lambda n$), which make up the grating 12.

One way to measure the bits in wavelength space is to have the input light angle $\theta i$ equal to the output light angle $\theta o$, which is kept at a constant value, and to provide an input wavelength $\lambda$ that satisfies the diffraction condition (Eq. 1) for each grating pitch $\Lambda$. This will maximize the optical power of the output signal for each pitch $\Lambda$ detected in the grating 12.

Referring to 33, illustration (b), the transmission wavelength spectrum of the transmitted output beam 330 (which is transmitted straight through the grating 12) will exhibit a series of notches (or dark spots) 696. Alternatively, instead of detecting the reflected output light 310, the transmitted light 330 may be detected at the detector/reader 308. It should be understood that the optical signal levels for the reflection peaks 695 and transmission notches 696 will depend on the "strength" of the grating 12, i.e., the magnitude of the index variation n in the grating 12.

In FIG. 32, the bits may be detected by continuously scanning the input wavelength. A known optical source 300 provides the input light signal 24 of a coherent scanned wavelength input light shown as a graph 304. The source 300 provides a sync signal on a line 306 to a known reader 308. The sync signal may be a timed pulse or a voltage ramped signal, which is indicative of the wavelength being provided as the input light 24 to the substrate 10 at any given time. The reader 308 may be a photodiode, CCD camera, or other optical detection device that detects when an optical signal is present and provides an output signal on a line 309 indicative of the code in the substrate 10 or of the wavelengths present in the output light, which is directly related to the code, as discussed herein. The grating 12 reflects the input light 24 and provides an output light signal 310 to the reader 308. The wavelength of the input signal is set such that the reflected output light 310 will be substantially in the center 314 of the Bragg envelope 200 for the individual grating pitch (or bit) being read.

Alternatively, the source 300 may provide a continuous broadband wavelength input signal such as that shown as a graph 316. In that case, the reflected output beam 310 signal is provided to a narrow band scanning filter 318 which scans across the desired range of wavelengths and provides a filtered output optical signal 320 to the reader 308. The filter 318 provides a sync signal on a line 322 to the reader, which is indicative of which wavelengths are being provided on the output signal 320 to the reader and may be similar to the sync signal discussed hereinbefore on the line 306 from the source 300. In this case, the source 300 does not need to provide a sync signal because the input optical signal 24 is continuous. Alternatively, instead of having the scanning filter being located in the path of the output beam 310, the scanning filter may be located in the path of the input beam 24 as indicated by the dashed box 324, which provides the sync signal on a line 323.

Alternatively, instead of the scanning filters 318,324, the reader 308 may be a known optical spectrometer (such as a known spectrum analyzer), capable of measuring the wavelength of the output light.

The desired values for the input wavelengths λ (or wavelength range) for the input signal 24 from the source 300 may be determined from the Bragg condition of Eq. 1, for a given grating spacing Λ and equal angles for the input light θi and the angle light θo. Solving Eq. 1 for λ and plugging in m=1, gives:

$$\lambda = \Lambda[\sin(\theta o) + \sin(\theta i)] \quad \text{Eq. 7}$$

It is also possible to combine the angular-based code detection with the wavelength-based code detection, both discussed hereinbefore. In this case, each readout wavelength is associated with a predetermined number of bits within the Bragg envelope. Bits (or grating pitches Λ) written for different wavelengths do not show up unless the correct wavelength is used.

Accordingly, the bits (or grating pitches Λ) can be read using one wavelength and many angles, many wavelengths and one angle, or many wavelengths and many angles.

Figure 34:
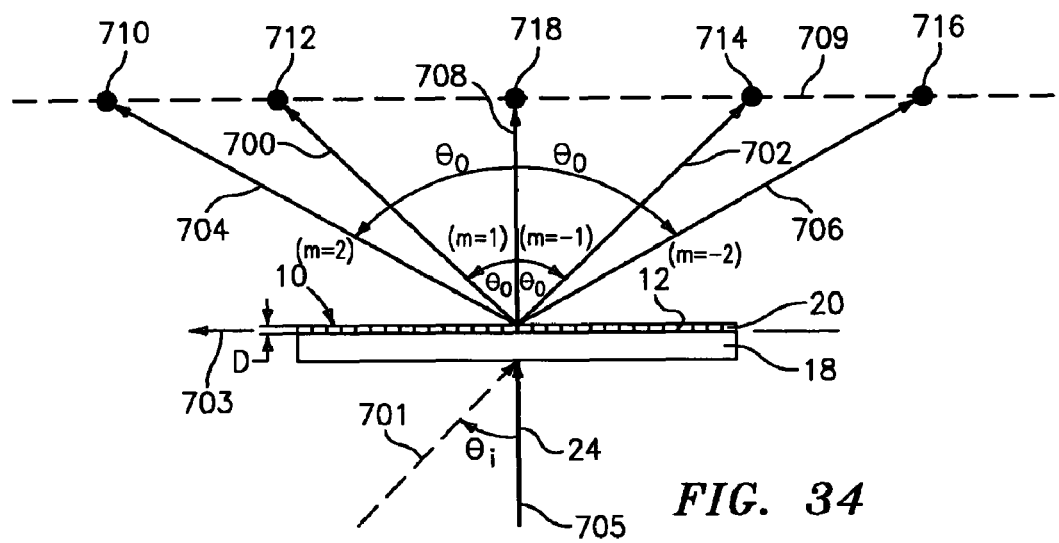
FIGS. 34-35 are side views of a thin grating for an optical identification element, in accordance with the present invention.

Referring to FIG. 34, the grating 12 may have a thickness or depth D which is comparable or smaller than the incident beam wavelength λ. This is known as a "thin" diffraction grating (or the full angle Bragg envelope is 180 degrees). In that case, the half-angle Bragg envelope θB is substantially 90 degrees; however, δn must be made large enough to provide sufficient reflection efficiency, per Eqs. 3 and 4. In particular, for a "thin" grating, D*δn≈λ/2, which corresponds to a π phase shift between adjacent minimum and maximum refractive index values of the grating 12.

It should be understood that there is still a trade-off discussed hereinbefore with beam divergence angle $\theta_R$ and the incident beam width (or length L of the substrate), but the accessible angular space is theoretically now 90 degrees. Also, for maximum efficiency, the phase shift between adjacent minimum and maximum refractive index values of the grating 12 should approach a π phase shift; however, other phase shifts may be used.

In this case, rather than having the input light 24 coming in at the conventional Bragg input angle θi, as discussed hereinbefore and indicated by a dashed line 701, the grating 12 is illuminated with the input light 24 oriented on a line 705 orthogonal to the longitudinal grating vector 705. The input beam 24 will split into two (or more) beams of equal amplitude, where the exit angle $\theta_o$ can be determined from Eq. 1 with the input angle $\theta_i$=0 (normal to the longitudinal axis of the grating 12).

In particular, from Eq. 1, for a given grating pitch Λ1, the +/−1$^{st}$ order beams (m=+1 and m=−1) correspond to output beams 700,702, respectively. The +/−2$^{nd}$ order beams (m=+2 and m=−2) correspond to output beams 704,706, respectively. The 0$^{th}$ order (undiffracted) beam (m=0) corresponds to beam 708 and passes straight through the substrate. The output beams 700-708 project spectral spots or peaks 710-718, respectively, along a common plane, shown from the side by a line 709, which is parallel to the upper surface of the substrate 10.

For example, for a grating pitch Λ=1.0 um, and an input wavelength λ=400 nm, the exit angles $\theta_o$ are ~+/−23.6 degrees (for m=+/−1), and +/−53.1 degrees (from m=+/−2), from Eq. 1. It should be understood that for certain wavelengths, certain orders (e.g., m=+/−2) may be reflected back toward the input side or otherwise not detectable at the output side of the grating 12.

Alternatively, one can use only the +/−1$^{st}$ order (m=+/−1) output beams for the code, in which case there would be only 2 peaks to detect, 712, 714. Alternatively, one can also use any one or more pairs from any order output beam that is capable of being detected. Alternatively, instead of using a pair of output peaks for a given order, an individual peak may be used.

Figure 35:
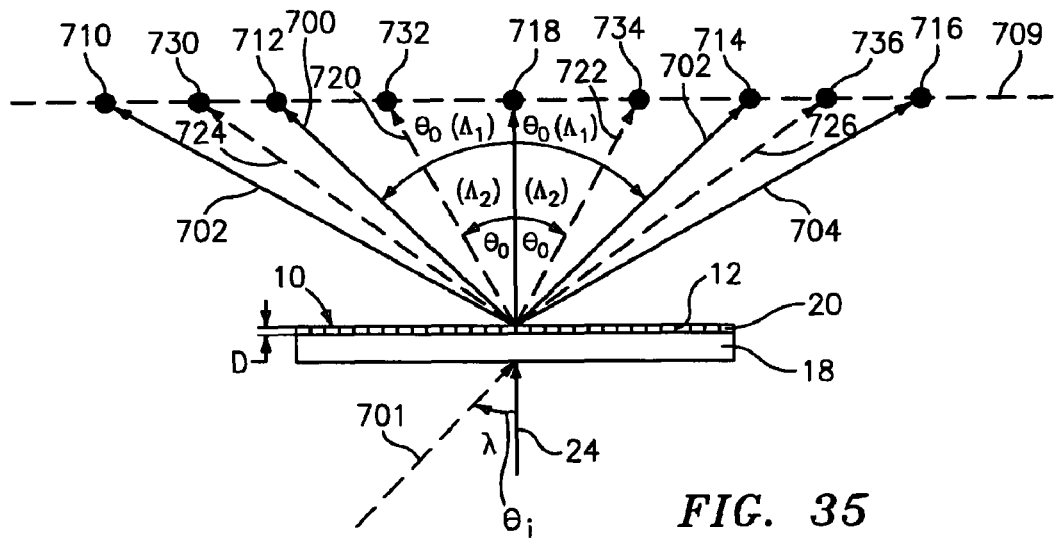

Referring to FIG. 35, if two pitches Λ1,Λ2 exist in the grating 12, two sets of peaks will exist. In particular, for a second grating pitch Λ2, the +/−1$^{st}$ order beams (m=+1 and m=−1) corresponds to output beams 720,722, respectively. For the +/−2$^{nd}$ order beams (m=+2 and m=−2), corresponds to output beams 724,726, respectively. The 0$^{th}$ order (un-diffracted) beam (m=0) corresponds to beam 718 and passes straight through the substrate. The output beams 720-726 corresponding to the second pitch Λ2 project spectral spots or peaks 730-736, respectively, which are at a different location than the point 710-716, but along the same common plane, shown from the side by the line 709.

Thus, for a given pitch Λ (or bit) in a grating, a set of spectral peaks will appear at a specific location in space. Thus, each different pitch corresponds to a different elevation or output angle which corresponds to a predetermined set of spectral peaks. Accordingly, the presence or absence of a particular peak or set of spectral peaks defines the code.

In general, if the angle of the grating 12 is not properly aligned with respect to the mechanical longitudinal axis of the substrate 10, the readout angles may no longer be symmetric, leading to possible difficulties in readout. With a thin grating, the angular sensitivity to the alignment of the longitudinal axis of the substrate 10 to the input angle θi of incident radiation is reduced or eliminated. In particular, the input light can be oriented along substantially any angle θi with respect to the grating 12 without causing output signal degradation, due the large Bragg angle envelope. Also, if the incident beam 24 is normal to the substrate 10, the grating 12 can be oriented at any rotational (or azimuthal) angle without causing output signal degradation. However, in each of these cases, changing the incident angle θi will affect the output angle θo of the reflected light in a predetermined predictable way, thereby allowing for accurate output code signal detection or compensation.

Referring to FIG. 36, for a thin grating, in addition to multiplexing in the elevation or output angle based on grating pitch Λ, the bits can also be multiplexed in an azimuthal (or rotational) angle θa of the substrate. In particular, a plurality of gratings 750,752,754,756 each having the same pitch Λ are disposed in a surface 701 of the substrate 10 and located in the plane of the substrate surface 701. The input light 24 is incident on all the gratings 750,752,754,756 simultaneously. Each of the gratings provides output beams oriented based on the grating orientation. For example, the grating 750 provides the output beams 764,762, the grating 752 provides the output beams 766,768, the grating 754 provides the output beams 770,772, and the grating 756 provides the output beams 774, 776. Each of the output beams provides spectral peaks or spots (similar to that discussed hereinbefore), which are located in a plane 760 that is parallel to the substrate surface plane 701. In this case, a single grating pitch Λ can produce many bits depending on the number of gratings that can be placed at different azimuthal (rotational) angles on the surface of the substrate 10 and the number of output beam spectral peaks that can be spatially and optically resolved/detected. Each bit may be viewed as the presence or absence of a pair of peaks located at a predetermined location in space in the plane 760. Note that this example uses only the m=+/−1$^{st}$ order for each reflected output beam. Alternatively, the detection may also use the m=+/−2$^{nd}$ order. In that case, there would be two additional output beams and peaks (not shown) for each grating (as discussed hereinbefore) that may lie in the same plane as the plane 760 and may be on a concentric circle outside the circle 760.

In addition, the azimuthal multiplexing can be combined with the elevation or output angle multiplexing discussed hereinbefore to provide two levels of multiplexing. Accordingly, for a thin grating, the number of bits can be multiplexed based on the number of grating pitches Λ and/or geometrically by the orientation of the grating pitches.

Furthermore, if the input light angle θi is normal to the substrate 10, the edges of the substrate 10 no longer scatter light from the incident angle into the "code angular space", as discussed herein and/or in the aforementioned patent application.

Also, in the thin grating geometry, a continuous broadband wavelength source may be used as the optical source if desired.

Referring to FIG. 37, instead of or in addition to the pitches Λ in the grating 12 being oriented normal to the longitudinal axis, the pitches may be created at a angle θg. In that case, when the input light 24 is incident normal to the surface 792, will produce a reflected output beam 790 having an angle θo determined by Eq. 1 as adjusted for the blaze angle θg. This can provide another level of multiplexing bits in the code.

Figure 38:
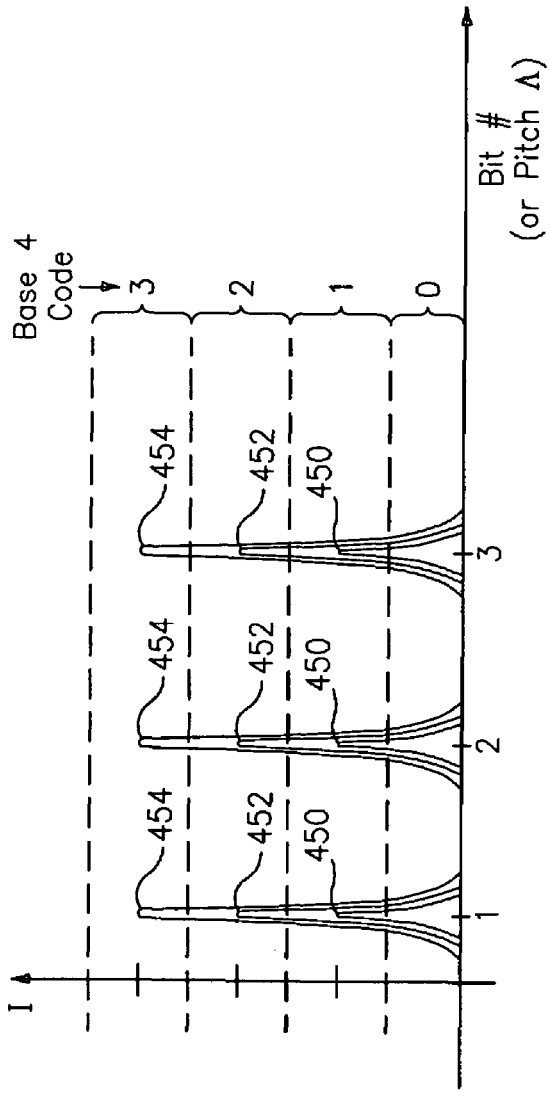
FIG. 38 is a graph of a plurality of states for each bit in a code for an optical identification element, in accordance with the present invention.

Referring to FIG. 38, instead of using an optical binary (0-1) code, an additional level of multiplexing may be provided by having the optical code use other numerical bases, if intensity levels of each bit are used to indicate code information. This could be achieved by having a corresponding magnitude (or strength) of the refractive index change (δn) for each grating pitch Λ. Four intensity ranges are shown for each bit number or pitch Λ, providing for a Base-4 code (where each bit corresponds to 0,1,2, or 3). The lowest intensity level, corresponding to a 0, would exist when this pitch Λ is not present in the grating 12. The next intensity level 450 would occur when a first low level δn1 exists in the grating that provides an output signal within the intensity range corresponding to a 1. The next intensity level 452 would occur when a second higher level δn2 exists in the grating 12 that provides an output signal within the intensity range corresponding to a 2. The next intensity level 452, would occur when a third higher level δn3 exists in the grating 12 that provides an output signal within the intensity range corresponding to a 3.

Figure 39:
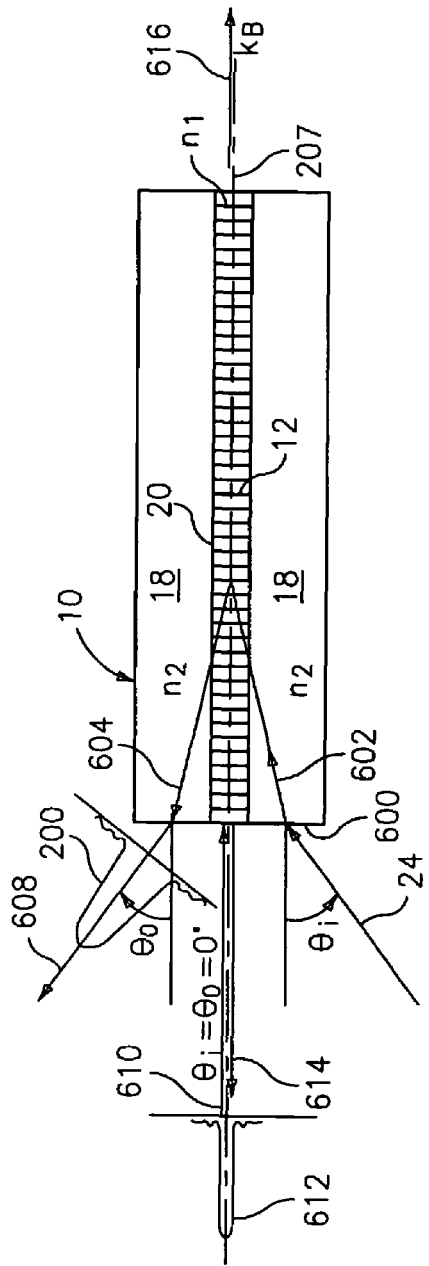
FIG. 39 is a side view of an optical identification element where light is incident on an end face, in accordance with the present invention.

Referring to FIG. 39, the input light 24 may be incident on the substrate 10 on an end face 600 of the substrate 10. In that case, the input light 24 will be incident on the grating 12 having a more significant component of the light (as compared to side illumination discussed hereinbefore) along the longitudinal grating axis 207 of the grating (along the grating vector k$_B$), as shown by a line 602. The light 602 reflects off the grating 12 as indicated by a line 604 and exits the substrate as output light 608. Accordingly, it should be understood by one skilled in the art that the diffraction equations discussed hereinbefore regarding output diffraction angle θo also apply in this case except that the reference axis would now be the grating axis 207. Thus, in this case, the input and output light angles θi,θo, would be measured from the grating axis 207 and length Lg of the grating 12 would become the thickness or depth D of the grating 12. As a result, a grating 12 that is 400 microns long, would result in the Bragg envelope 200 being narrow. It should be understood that because the values of n1 and n2 are close to the same value, the slight angle changes of the light between the regions 18,20 are not shown herein.

In the case where incident light 610 is incident along the same direction as the grating vector (Kb) 207, i.e., θi=0 degrees, the incident light sees the whole length Lg of the grating 12 and the grating provides a reflected output light angle θo=0 degrees, and the Bragg envelope 612 becomes extremely narrow, as the narrowing effect discussed above reaches a limit. In that case, the relationship between a given pitch Λ in the grating 12 and the wavelength of reflection λ is governed by a known "Bragg grating" relation:

$$\lambda = 2n_{eff}\Lambda \qquad \text{Eq. 8}$$

where n$_{eff}$ is the effective index of refraction of the substrate, λ is the input (and output wavelength) and Λ is the pitch. This relation, as is known, may be derived from Eq. 1 where θi=θo=90 degrees.

In that case, the code information is readable only in the spectral wavelength of the reflected beam, similar to that discussed hereinbefore for wavelength based code reading. Accordingly, the input signal in this case may be a scanned wavelength source or a broadband wavelength source. In addition, as discussed hereinbefore for wavelength based code reading, the code information may be obtained in reflection from the reflected beam 614 or in transmission by the transmitted beam 616 that passes through the grating 12.

It should be understood that for shapes of the substrate 10 or element 8 other than a cylinder, the effect of various different shapes on the propagation of input light through the element 8, substrate 10, and/or grating 12, and the associated reflection angles, can be determined using known optical physics including Snell's Law, shown below:

$$n_{in} \sin \theta in = n_{out} \sin \theta out \qquad \text{Eq. 9}$$

where n$_{in}$ is the refractive index of the first (input) medium, and n$_{out}$ is the refractive index of the second (output) medium, and θin and θout are measured from a line 620 normal to an incident surface 622.

Referring to FIG. 40, if the value of n1 in the grating region 20 is greater than the value of n2 in the non-grating region 18, the grating region 20 of the substrate 10 will act as a known optical waveguide for certain wavelengths. In that case, the grating region 20 acts as a "core" along which light is guided and the outer region 18 acts as a "cladding" which helps confine or guide the light. Also, such a waveguide will have a known "numerical aperture" (θna) that will allow light that is within the aperture θna to be directed or guided along the grating axis 207 and reflected axially off the grating 12 and returned and guided along the waveguide. In that case, the grating 12 will reflect light having the appropriate wavelengths equal to the pitches Λ present in the grating 12 back along the region 20 (or core) of the waveguide, and pass the remaining wavelengths of light as the light 632. Thus, having the grating region 20 act as an optical waveguide for wavelengths reflected by the grating 12 allows incident light that is not aligned exactly with the grating axis 207 to be guided along and aligned with the grating 12 axis 207 for optimal grating reflection.

If an optical waveguide is used any standard waveguide may be used, e.g., a standard telecommunication single mode optical fiber (125 micron diameter or 80 micron diameter fiber with about a 8-10 micron diameter), or a larger diameter waveguide (greater than 0.5 mm diameter), such as is describe in U.S. patent application, Ser. No. 09/455,868, filed Dec. 6, 1999, entitled "Large Diameter Waveguide, Grating". Further, any type of optical waveguide may be used for the optical substrate 10, such as, a multi-mode, birefringent, polarization maintaining, polarizing, multi-core, multi-cladding, or microsturctured optical waveguide, or a flat or planar waveguide (where the waveguide is rectangular shaped), or other waveguides.

Referring to FIG. 41, if the grating 12 extends across the entire dimension D of the substrate, the substrate 10 does not behave as a waveguide for the incident or reflected light and the incident light 24 will be diffracted (or reflected) as indicated by lines 642, and the codes detected as discussed hereinbefore for the end-incidence condition discussed hereinbefore with FIG. 45, and the remaining light 640 passes straight through.

Referring to FIG. 42, illustrations (a)-(c), in illustration (a), for the end illumination condition, if a blazed or angled grating is used, as discussed hereinbefore, the input light 24 is coupled out of the substrate 10 at a known angle as shown by a line 650. Referring to FIG. 42, illustration (b), alternatively, the input light 24 may be incident from the side and, if the grating 12 has the appropriate blaze angle, the reflected light will exit from the end face 652 as indicated by a line 654. Referring to FIG. 42, illustration (c), the grating 12 may have a plurality of different pitch angles 660,662, which reflect the input light 24 to different output angles as indicated by lines 664, 666. This provides another level of multiplexing (spatially) additional codes, if desired.

The grating 12 may be impressed in the substrate 10 by any technique for writing, impressed, embedded, imprinted, or otherwise forming a diffraction grating in the volume of or on a surface of a substrate 10. Examples of some known techniques are described in U.S. Pat. Nos. 4,725,110 and 4,807,950, entitled "Method for Impressing Gratings Within Fiber Optics", to Glenn et al; and U.S. Pat. No. 5,388,173, entitled "Method and Apparatus for Forming Aperiodic Gratings in Optical Fibers", to Glenn, respectively, and U.S. Pat. No. 5,367,588, entitled "Method of Fabricating Bragg Gratings Using a Silica Glass Phase Grating Mask and Mask Used by Same", to Hill, and U.S. Pat. No. 3,916,182, entitled "Periodic Dielectric Waveguide Filter", Dabby et al, and U.S. Pat. No. 3,891,302, entitled "Method of Filtering Modes in Optical Waveguides", to Dabby et al, which are all incorporated herein by reference to the extent necessary to understand the present invention.

Alternatively, instead of the grating 12 being impressed within the substrate material, the grating 12 may be partially or totally created by etching or otherwise altering the outer surface geometry of the substrate to create a corrugated or varying surface geometry of the substrate, such as is described in U.S. Pat. No. 3,891,302, entitled "Method of Filtering Modes in Optical Waveguides", to Dabby et al, which is incorporated herein by reference to the extent necessary to understand the present invention, provided the resultant optical refractive profile for the desired code is created.

Further, alternatively, the grating 12 may be made by depositing dielectric layers onto the substrate, similar to the way a known thin film filter is created, so as to create the desired resultant optical refractive profile for the desired code.

The substrate 10 (and/or the element 8) may have end-view cross-sectional shapes other than circular, such as square, rectangular, elliptical, clam-shell, D-shaped, or other shapes, and may have side-view sectional shapes other than rectangular, such as circular, square, elliptical, clam-shell, D-shaped, or other shapes. Also, 3D geometries other than a cylinder may be used, such as a sphere, a cube, a pyramid or any other 3D shape. Alternatively, the substrate 10 may have a geometry that is a combination of one or more of the foregoing shapes.

The shape of the element 8 and the size of the incident beam may be made to minimize any end scatter off the end face(s) of the element 8, as is discussed herein and/or in the aforementioned patent application. Accordingly, to minimize such scatter, the incident beam 24 may be oval shaped where the narrow portion of the oval is smaller than the diameter D1, and the long portion of the oval is smaller than the length L of the element 8. Alternatively, the shape of the end faces may be rounded or other shapes or may be coated with an antireflective coating.

It should be understood that the size of any given dimension for the region 20 of the grating 12 may be less than any corresponding dimension of the substrate 10. For example, if the grating 12 has dimensions of length Lg, depth Dg, and width Wg, and the substrate 12 has different dimensions of length L, depth D, and width W, the dimensions of the grating 12 may be less than that of the substrate 12. Thus, the grating 12, may be embedded within or part of a much larger substrate 12. Also, the element 8 may be embedded or formed in or on a larger object for identification of the object.

The dimensions, geometries, materials, and material properties of the substrate 10 are selected such that the desired optical and material properties are met for a given application. The resolution and range for the optical codes are scalable by controlling these parameters as discussed herein and/or in the aforementioned patent application.

Referring to FIG. 43, the substrate 10 may have an outer coating 799, such as a polymer or other material that may be dissimilar to the material of the substrate 10, provided that the coating 799 on at least a portion of the substrate, allows sufficient light to pass through the substrate for adequate optical detection of the code. The coating 799 may be on any one or more sides of the substrate 10. Also, the coating 799 may be a material that causes the element 8 to float or sink in certain fluids (liquid and/or gas) solutions.

Also, the substrate 10 may be made of a material that is less dense than certain fluid (liquids and/or gas) solutions, thereby allowing the elements 8 to float or be buoyant or partially buoyant. Also, the substrate may be made of a porous material, such as controlled pore glass (CPG) or other porous material, which may also reduce the density of the element 8 and may make the element 8 buoyant or partially-buoyant in certain fluids.

Referring to FIG. 44, the grating 12 is axially spatially invariant. As a result, the substrate 10 with the grating 12 (shown as a long substrate 21) may be axially subdivided or cut into many separate smaller substrates 30-36 and each substrate 30-36 will contain the same code as the longer substrate 21 had before it was cut. The limit on the size of the smaller substrates 30-36 is based on design and performance factors discussed herein and/or in the aforementioned patent application.

Referring to FIG. 45, one purpose of the outer region 18 (or region without the grating 12) of the substrate 10 is to provide mechanical or structural support for the inner grating region 20. Accordingly, the entire substrate 10 may comprise the grating 12, if desired. Alternatively, the support portion may be completely or partially beneath, above, or along one or more sides of the grating region 20, such as in a planar geometry, or a D-shaped geometry, or other geometries, as described herein and/or in the aforementioned patent application. The non-grating portion 18 of the substrate 10 may be used for other purposes as well, such as optical lensing effects or other effects (discussed herein or in the aforementioned patent application). Also, the end faces of the substrate 10 need not be perpendicular to the sides or parallel to each other. However, for applications where the elements 8 are stacked end-to-end, the packing density may be optimized if the end faces are perpendicular to the sides.

Referring to FIG. 46, illustrations (a)-(c), two or more substrates 10,250, each having at least one grating therein, may be attached together to form the element 8, e.g., by an adhesive, fusing or other attachment techniques. In that case, the gratings 12,252 may have the same or different codes.

Referring to FIG. 47, illustrations (a) and (b), the substrate 10 may have multiple regions 80,90 and one or more of these regions may have gratings in them. For example, there may be gratings 12,252 side-by-side (illustration (a)), or there may be gratings 82-88, spaced end-to-end (illustration (b)) in the substrate 10.

Referring to FIG. 48, the length L of the element 8 may be shorter than its diameter D, thus, having a geometry such as a plug, puck, wafer, disc or plate.

Referring to FIG. 49, to facilitate proper alignment of the grating axis with the angle θi of the input beam 24, the substrate 10 may have a plurality of the gratings 12 having the same codes written therein at numerous different angular or rotational (or azimuthal) positions of the substrate 10. In particular, two gratings 550, 552, having axial grating axes 551, 553, respectively may have a common central (or pivot or rotational) point where the two axes 551,553 intersect. The angle θi of the incident light 24 is aligned properly with the grating 550 and is not aligned with the grating 552, such that output light 555 is reflected off the grating 550 and light 557 passes through the grating 550 as discussed herein. If the element 8 is rotated as shown by the arrows 559, the angle θi of incident light 24 will become aligned properly with the grating 552 and not aligned with the grating 550 such that output light 555 is reflected off the grating 552 and light 557 passes through the grating 552. When multiple gratings are located in this rotational orientation, the bead may be rotated as indicated by a line 559 and there may be many angular positions that will provide correct (or optimal) incident input angles θi to the grating. While this example shows a circular cross-section, this technique may be used with any shape cross-section.

Figure 50:
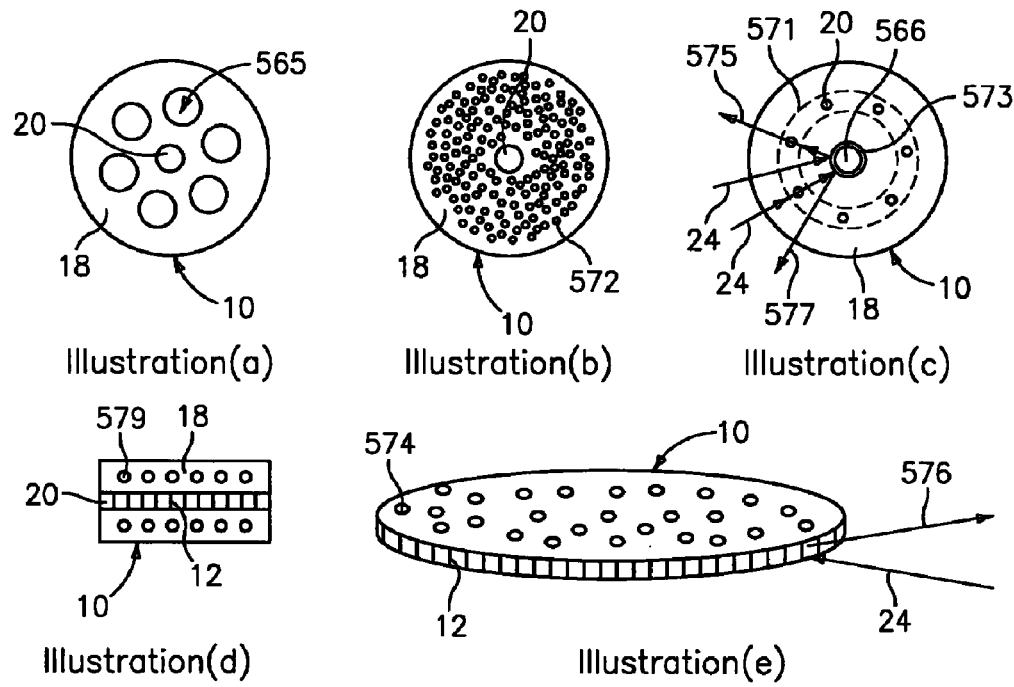
FIG. 50 illustrations (a)-(e) show various geometries of an optical identification element that may have holes therein, in accordance with the present invention.

Referring to FIG. 50, illustrations (a), (b), (c), (d), and (e) the substrate 10 may have one or more holes located within the substrate 10. In illustration (a), holes 560 may be located at various points along all or a portion of the length of the substrate 10. The holes need not pass all the way through the substrate 10. Any number, size and spacing for the holes 560 may be used if desired. In illustration (b), holes 572 may be located very close together to form a honeycomb-like area of all or a portion of the cross-section. In illustration (c), one (or more) inner hole 566 may be located in the center of the substrate 10 or anywhere inside of where the grating region(s) 20 are located. The inner hole 566 may be coated with a reflective coating 573 to reflect light to facilitate reading of one or more of the gratings 12 and/or to reflect light diffracted off one or more of the gratings 12. The incident light 24 may reflect off the grating 12 in the region 20 and then reflect off the surface 573 to provide output light 577. Alternatively, the incident light 24 may reflect off the surface 573, then reflect off the grating 12 and provide the output light 575. In that case the grating region 20 may run axially or circumferentially 571 around the substrate 10. In illustration (d), the holes 579 may be located circumferentially around the grating region 20 or transversely across the substrate 10. In illustration (e), the grating 12 may be located circumferentially around the outside of the substrate 10, and there may be holes 574 inside the substrate 10.

Figure 51:
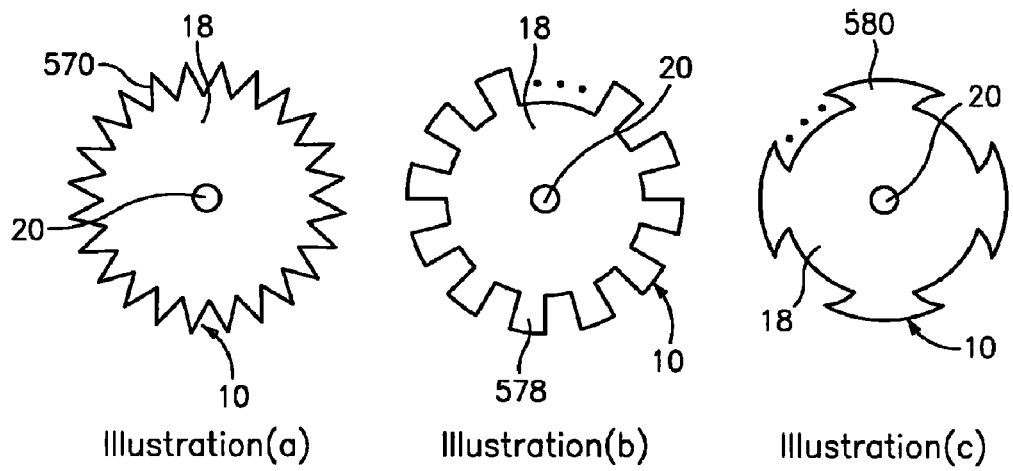
FIG. 51 illustrations (a)-(c) show various geometries of an optical identification element that may have teeth thereon, in accordance with the present invention.

Referring to FIG. 51, illustrations (a), (b), and (c), the substrate 10 may have one or more protruding portions or teeth 570, 578,580 extending radially and/or circumferentially from the substrate 10. Alternatively, the teeth 570, 578, 580 may have any other desired shape.

Figure 52:
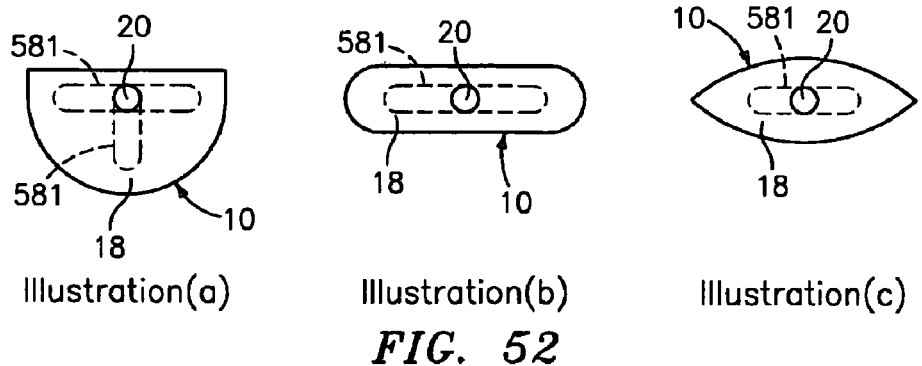
FIG. 52 illustrations (a)-(c) show various geometries of an optical identification element, in accordance with the present invention.

Referring to FIG. 52, illustrations (a), (b), (c) a D-shaped substrate, a flat-sided substrate and an eye-shaped (or clamshell or teardrop shaped) substrate 10, respectively, are shown. Also, the grating region 20 may have end cross-sectional shapes other than circular and may have side cross-sectional shapes other than rectangular, such as any of the geometries described herein for the substrate 10. For example, the grating region 20 may have a oval cross-sectional shape as shown by dashed lines 581, which may be oriented in a desired direction, consistent with the teachings herein. Any other geometries for the substrate 10 or the grating region 20 may be used if desired, as described herein.

Referring to FIG. 53, at least a portion of a side of the substrate 10 may be coated with a reflective coating to allow incident light 510 to be reflected back to the same side from which the incident light came, as indicated by reflected light 512. Referring to FIG. 54, illustrations (a) and (b), alternatively, the substrate 10 can be electrically and/or magnetically polarized, by a dopant or coating, which may be used to ease handling and/or alignment or orientation of the substrate 10 and/or the grating 12, or used for other purposes. Alternatively, the bead may be coated with conductive material, e.g., metal coating on the inside of a holy substrate, or metallic dopant inside the substrate. In these cases, such materials can cause the substrate 10 to align in an electric or magnetic field. Alternatively, the substrate can be doped with an element or compound that fluoresces or glows under appropriate illumination, e.g., a rare earth dopant, such as Erbium, or other rare earth dopant or fluorescent or luminescent molecule. In that case, such fluorescence or luminescence may aid in locating and/or aligning substrates.

Referring to FIG. 56, an embodiment having a plurality of tubes or fluidic channels with the beads 8 therein, are connected by a single input and output port to allow for parallel reaction, thereby allowing the stick to be shorter in length or a different geometry or different kinetics if desired.

Referring to FIG. 55, the assay stick of the present invention also allows for traceability of each bead in the assay stick. Accordingly, each bead 8 can have a batch code, lot number, date code, functionalization date, location, vendor code, and/or any other information desired or required for traceability, identification, and/or authenticity. In addition this information may be encrypted for covert applications to avoid counterfeiting of assay sticks.

In particular, referring to FIG. 55, the code may be a simple code or may be a more complex code having many pieces of information located in the code. In addition, the code may have checks within the code to ensure the code is read correctly. It can be viewed as a serial digital message, word, or frame consisting of N bits.

In particular, there may be start and stop bits 869, 871, respectively. The start and stop bits may each take up more than one bit location if desired. In addition there may be an error check portion of the message, such as a check sum or CRC (cyclic redundancy check), having a predetermined number of bits, and a code section 873 having a predetermined number of bits. The error check portion ensures that the code which is obtained from the bead is accurate. Accordingly, having a large number of bits in the element 8 allows for greater statistical accuracy in the code readout and decreases the likelihood of providing an erroneous code. Accordingly, if a code cannot be read without an error, no code will be provided, avoiding an erroneous result. Any known techniques for digital error checking for single or multi-bit errors may be used.

The code section 873 may be broken up into one or more groups of bits, for example, three bit groups 863,865,867, each bit group containing information about the bead itself or the item attached to the bead or how the bead is to be used, or other information. For example, the first bit group 863 may contain information regarding "identifying numbers", such as: lot number, quality control number, model number, serial number, inventory control number; the second bit group 865 may contain "type" information, such as: probe, chemical or cell type, experiment type, item type, animal type; and the third bit group 867 may contain "date" information, such as: manufactured date, experiment date, creation date, initial tracking date. Any other bit groups, number of bit groups, or size of bit groups may be used if desired. Also, additional error or fault checking can be used if desired.

In particular, for an assay application, the code may have the serial number, the lot number, date of manufacture, information about the chemical attached to the bead, the date and/or time of creation of the chemical or experiment, or other information of interest. The bead code may have any other information that identifies the item and/or information about the bead/assay.

Referring to FIG. 57, the beads 8 need not fill the entire tube. For example, a predetermined number of beads 1010 fills a portion of the tube and the remainder of the tube 1012 may be empty. This may allow the beads 8 to move back and forth within the tube 7 by the fluid passing by the beads 8. This allows the beads 8 to be read by a stationary reader and a stationary tube 7, and have the beads 8 move by the excitation/detector devices in the reader, or a combination of bead movement and tube or reader head movement may be used.

In addition, the tube allows the measurement of the chemical reaction with a first fluid and then, after the initial binding/chemical reaction with the beads is complete, a second fluid may be washed across the beads, e.g., cleaning fluid or water, which removes the chemical reaction from the beads. This allows for the measurement of actual kinetic constants of the reaction, i.e., the attachment and then removal of the chemicals from the beads, for a dynamical measurement of the reaction. The second fluid process can also can be done at a different temperature or other different parameters from the original reaction, if desired.

Alternatively, referring to FIG. 58, the beads 8 may be attached to a planar surface material or test strip, which is then dipped into the desired chemical solution. Alternatively, the beads may be sandwiched between two planar surfaces to minimize reaction volume.

Figure 59:
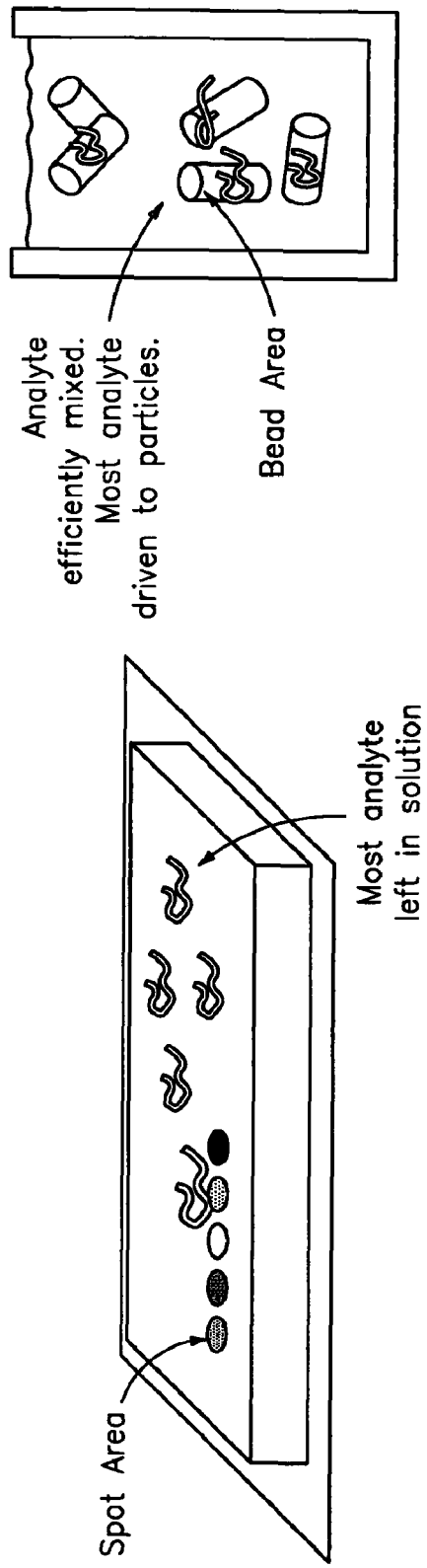
FIG. 59 shows a diagram of a planar microarray and a bead array in solution, in accordance with the present invention.

Referring to FIG. 59, a comparison of a microarray and beads in solution are shown. For a microarray, a typical volume is about 100 microliters, and a typical spot area is about 10,000 microns$^2$; so the volume/area=about 10 meters. For the beads 8 having a size of about 28 microns diameter, and length of about 250 microns, a typical volume is about 3 microliters and a typical area is about 100,000 microns$^2$; so the volume/area=about 0.03 meters. This small volume over large area makes the reaction occur much faster than a planar microarray format. In particular, it drives the reaction time and degree of completion, dramatically improves sensitivity and quantitation over microarrays, and allows near complete collection of analyte, thereby providing an indication of molecule counting.

Figure 60:
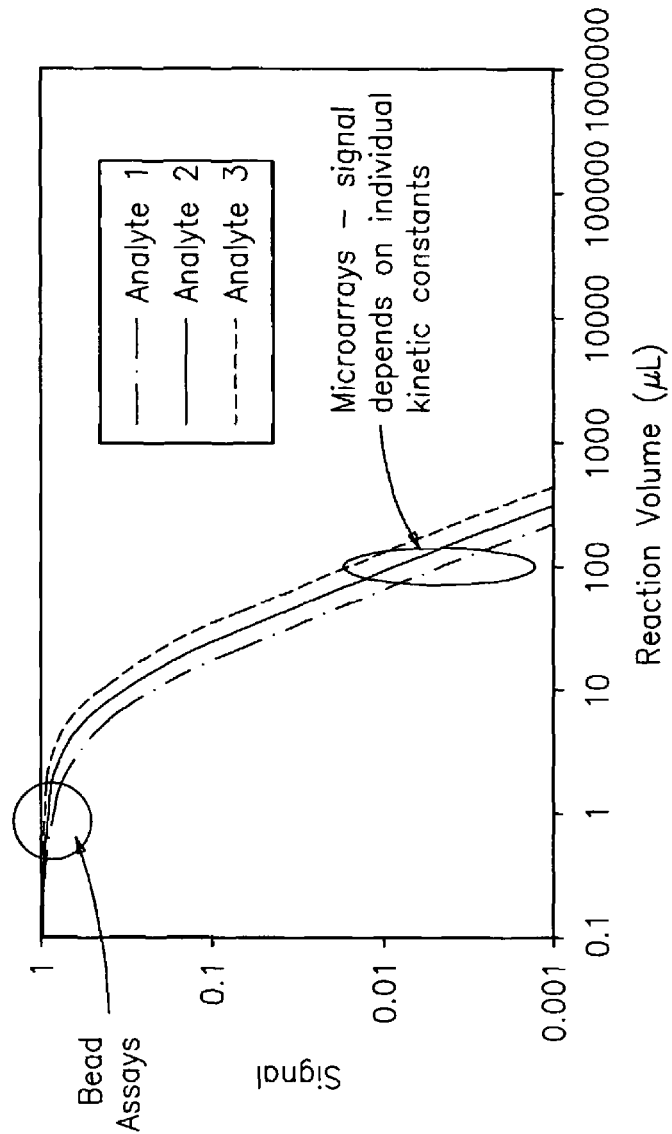
FIG. 60 shows a graph of signal to reaction volume for 3 different analytes, in accordance with the present invention.

Referring to FIG. 60, a graph illustrates a comparison between microarrays and bead assays for 3 analytes showing signal vs. reaction volume, where the overall rate of reaction is proportional to area/volume; where small volumes over a large area makes the reaction fast and allows complete collection of the analyte.

DESCRIPTION OF INVENTION

As discussed hereinbefore, the microbeads are pre-package into arrays of particles in a fused silica capillary. FIG. 1 shows an example format for pre-assembling and decoding particles arranged in a capillary microfluidic channel.

Figure 61:
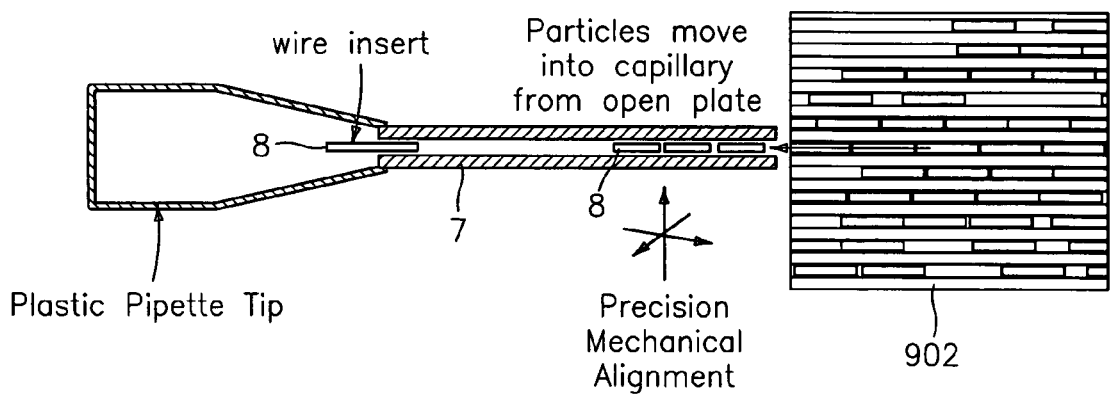
FIG. 61 shows a diagram of a proposed process for assembling particles into a capillary.

One proposed process for loading microbead particles into the capillary is illustrated in FIG. 61. Particles are first randomly self-assembled onto a 2-dimensional groove plate as in a groove plate 902. Then the capillary tube 7 is brought to the end of one of the grooves and carefully aligned. The particles 8 will then be flowed into the capillary 7 by drawing on the distal end.

Note that a similar format has already been demonstrated using spherical particles [6A-8A]. See [6A] Kohara Y., Hybridization reaction kinetics of DNA probes on beads arrayed in a capillary enhanced by turbulent flow. Anal Chem. 2003 Jul. 1; 75(13):3079-85; [7A] Kohara Y, Noda H, Okano K, Kambara H., DNA hybridization using "bead-array": probe-attached beads arrayed in a capillary in a predetermined order. Nucleic Acids Res Suppl. (2001) 1:83-4; and [8A] Noda H, Kohara Y, Okano K, Kambara H., Automated bead alignment apparatus using a single bead capturing technique for fabrication of a miniaturized bead-based DNA probe array. Anal Chem. (2003) July 1; 75(13):3250-5. A key limitation of this format is the necessity of individually picking and placing particles in the capillary in a pre-defined order [8A]. If a mistake is made there is no easy way to identify the particles, leading potentially to misidentification of an analyte specific particle. The optical digital code technology of the present technology eliminates this issue entirely because the particles 8 are positively identified at the time of assay. Further, because the optical encoding mechanism packs a large amount of information, the particles can be batch traceable back to date and time of manufacture, allowing standards curves to be automatically updated for each batch of processed particles, as discussed hereinbefore.

There are also other reasons why the capillary format is desirable. Since the CyVera particles are cylindrically shaped, they fill the space within the capillary more efficiently than any other shape. In principle the reaction volumes (the amount of fluid necessary to cover the particle surface) can be made much smaller than when using spherical particles, and will increase the reaction kinetics by maximizing the surface/volume ratio. In addition, fused silica capillary is material readily available, inexpensive, and exhibits extremely low background fluorescence.

Figure 62:
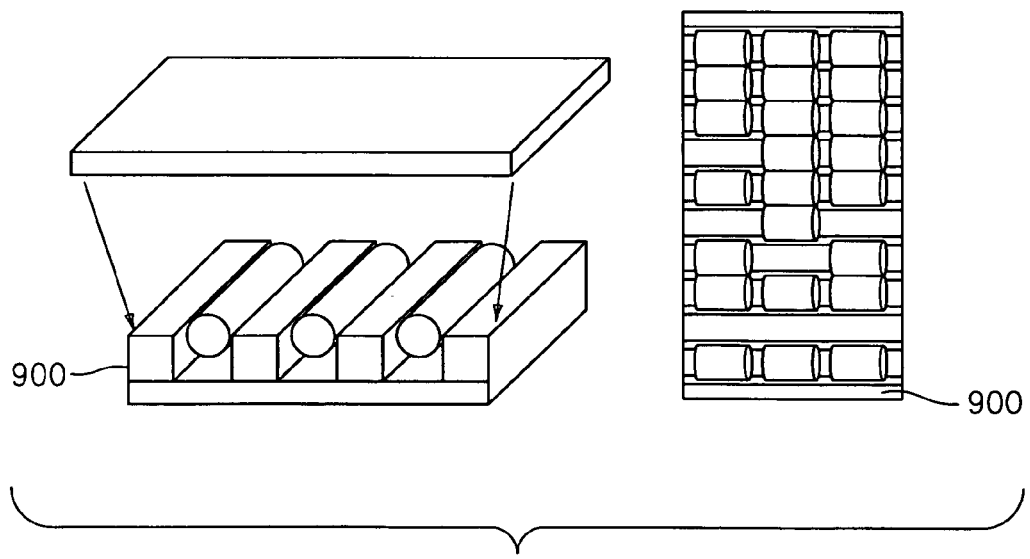
FIG. 62 shows an illustation of capturing particles that are self-assembled into fluidic channels defined by a photoresist.

Referring to FIG. 62, rather than assembling particles onto a groove plate and flowing them into a separate capillary, the particles 8 assemble into flow channels defined in a planar substrate. In that case, grooves are/or channels are etched into a substrate 900 surface, e.g., by microlithography or another approach. The particles 8, once assembled, never leave their positions and are captured by a transparent top plate.

Figure 63:
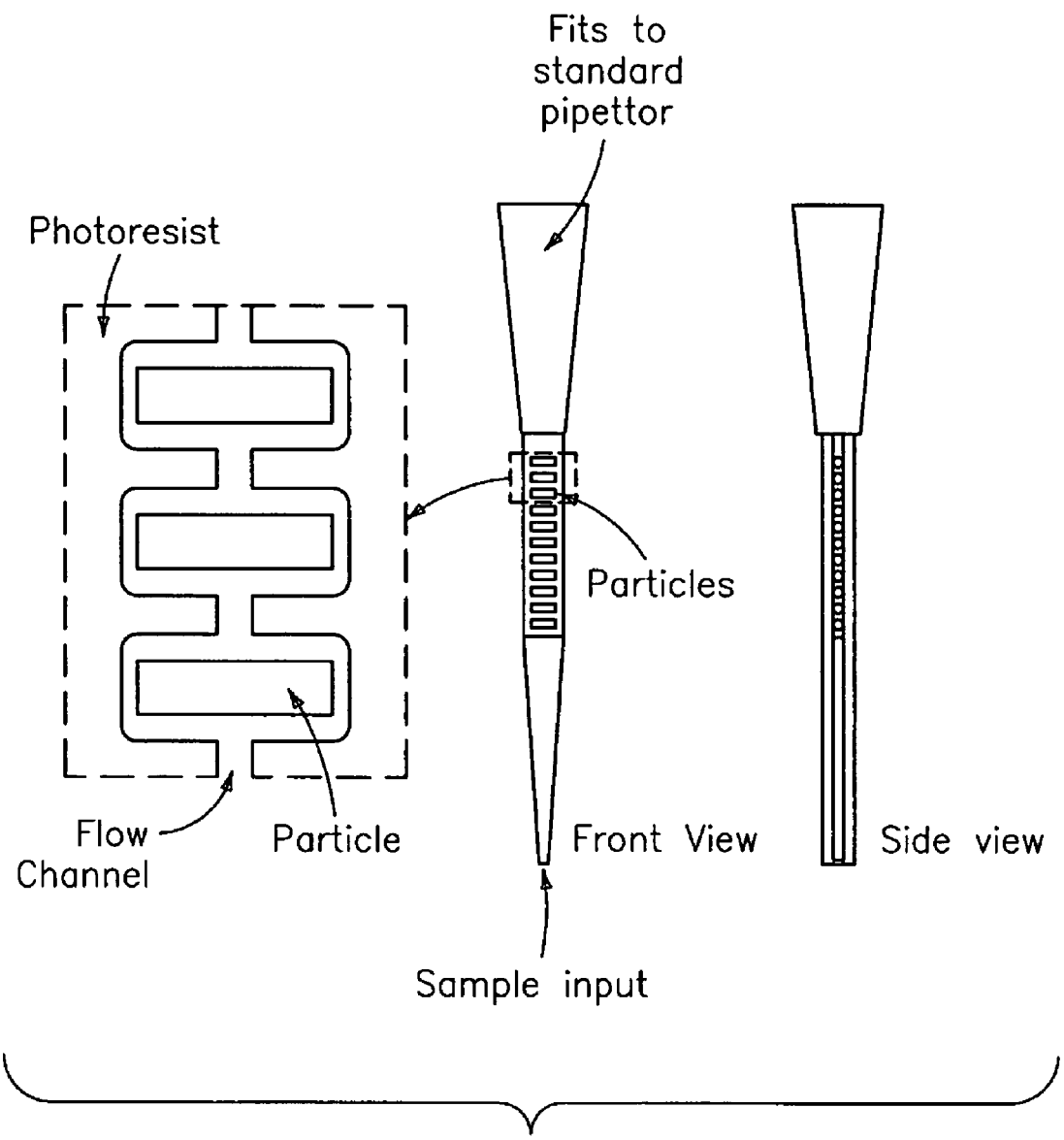
FIG. 63 shows details of a microfluidic particle assay assembly.

FIG. 63 also shows a photomicrograph (right) of a similar structure used to singulate beads. The substrate 900 was patterned in thick photoresist SU-8 (Microchem, Newton Mass.). The photoresist SU-8 can be used to develop a similar structure, but one with fluidic channels connecting the beads as illustrated in FIG. 63. While SU-8 exhibits high background fluorescence, it does allow rapid prototyping and helps prove feasibility. Other methods may be to define channels, such as patterned thick metal coatings or embossed low fluorescence plastic or other techniques, to circumvent any residual fluorescence issues if they exist.

FIG. 63 (inset at left) illustrates a possible configuration of the flow channels. The top side of the flow channels are connected to an adapter than can be directly attached to a standard pipettor. The bottom side resembles a standard pipette tip. Once assembled the holographic codes embedded in the particles are read to determine the identity of the probes in the channels.

Figure 64:
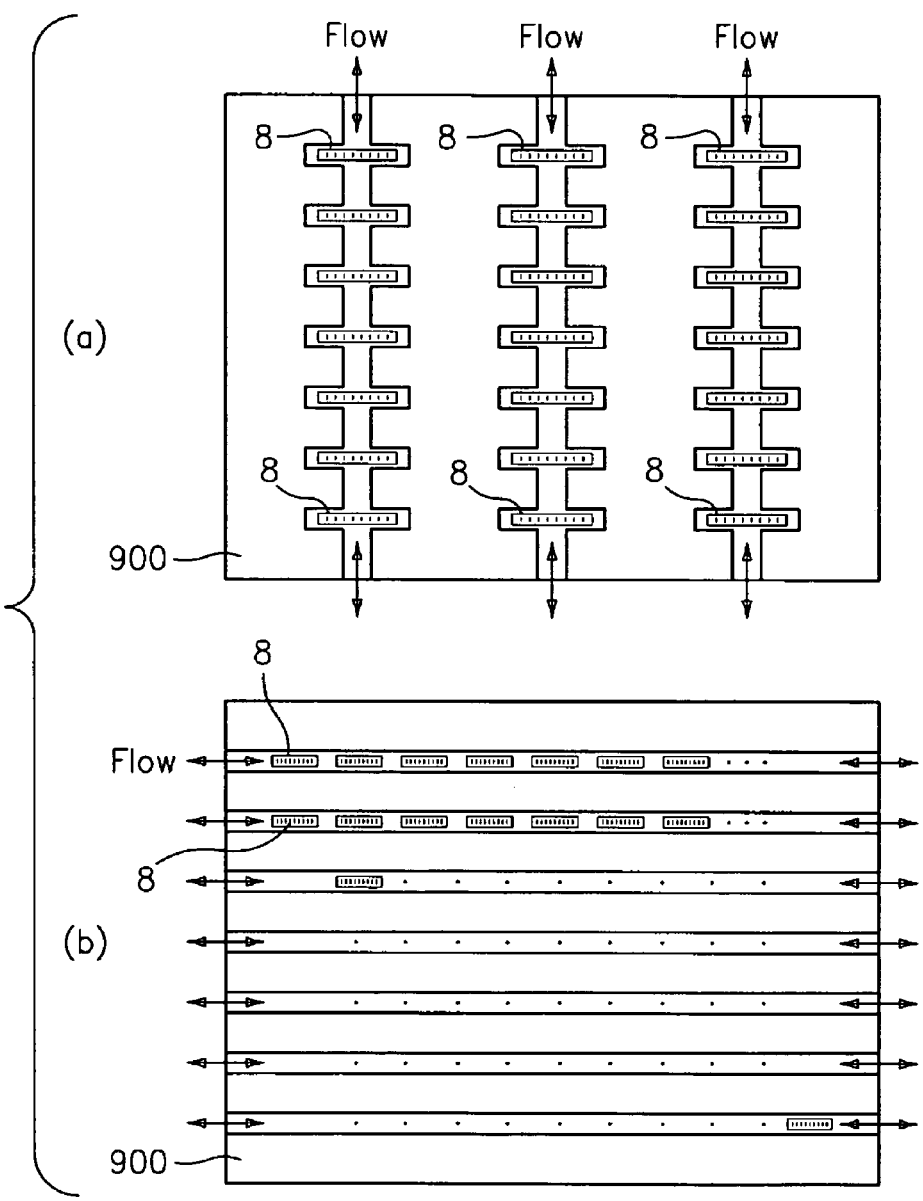
FIG. 64 shows a diagram of a substrate having channels.

Referring to FIG. 64, illustrations (a) and (b), the channels may be formed on the substrate 900 such that the beads have their longitudinal axis in the direction of flow (b) or normal to the direction of flow (as shown in (a)), or any other desired orientation.

SCOPE OF THE INVENTION

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An assay device comprising:
a plurality of microbeads, each microbead having at least one diffraction grating disposed therein, the grating providing an output optical signal indicative of a code when illuminated by an incident light signal; and
a reaction vessel having a cavity extending a length therein, the reaction vessel being configured to hold the microbeads within the cavity.

2. The assay device of claim 1 wherein the cavity has a cross-sectional shape and the microbeads have a common cross-sectional shape with respect to each other, the cross-sectional shape of the cavity being similar in shape to the cross-sectional shape of the microbeads.

3. The assay device of claim 1 wherein the cavity has a cross-sectional shape and the microbeads have a common cross-sectional shape with respect to each other, the cross-sectional shape of the cavity being slightly larger than the cross-sectional shape of the microbeads.

4. The assay device of claim 1 wherein the microbeads have a total length when arranged end-to-end or side-to-side within the cavity, the length of the cavity being substantially equal to the total length of the microbeads.

5. The assay device of claim 1 wherein the reaction vessel has two opposing ends with the cavity extending therebetween, the ends of the reaction vessel being configured to prevent the microbeads from falling out of the reaction vessel.

6. The assay device of claim 5 wherein at least one of the ends has an end cap coupled thereto to prevent the microbeads from falling out of the reaction vessel.

7. The assay device of claim 5 wherein at least one of the ends is at least partially collapsed into the cavity to prevent the microbeads from falling out of the reaction vessel.

8. The assay device of claim 1 wherein the microbeads are stacked end-to-end or side-to-side within the reaction vessel.

9. The assay device of claim 1 wherein the microbeads comprise a substantially single material.

10. The assay device of claim 1 wherein the microbeads have a cylindrical shape.

11. The assay device of claim 1 wherein the microbeads have a reflective coating disposed thereon.

12. The assay device of claim 1 wherein the microbeads include a magnetic or electric charge polarization.

13. The assay device of claim 1 wherein the cavity includes a plurality of cavities, each cavity extending a corresponding length within the reaction vessel.

14. The assay device of claim 1 wherein the reaction vessel has a cylindrical shape.

15. The assay device of claim 1 wherein the reaction vessel comprises a material that is transparent to an incident light signal.

16. A method of performing an assay, the method comprising:
obtaining a reaction vessel having a cavity extending a length therein, the reaction vessel including a plurality of microbeads held within the cavity, each microbead having at least one diffraction grating disposed therein;
illuminating the microbeads with an incident light signal, the grating of each microbead providing an output light signal indicative of a code; and
reading said output light signal and detecting the code therefrom.

17. The method of claim 16 further comprising conveying fluid through the cavity using a fluidic control device, the microbeads being held within the reaction vessel while the fluid is flowing therethrough.

18. The method of claim 16 wherein the cavity of the reaction vessel has a cross-sectional shape and the microbeads have a common cross-sectional shape with respect to each other, the cross-sectional shape of the cavity being similar in shape to the cross-sectional shape of the microbeads.

19. The method of claim 16 wherein the cavity of the reaction vessel has a cross-sectional shape and the microbeads have a common cross-sectional shape with respect to each other, the cross-sectional shape of the cavity being slightly larger than the cross-sectional shape of the microbeads.

20. The method of claim 16 wherein the microbeads have a total length when arranged end-to-end or side-to-side within the cavity, the length of the cavity being substantially equal to the total length of the microbeads.

* * * * *